(12) United States Patent
Selnick et al.

(10) Patent No.: US 9,938,299 B2
(45) Date of Patent: Apr. 10, 2018

(54) GLYCOSIDASE INHIBITORS AND USES THEREOF

(71) Applicants: MERCK SHARP & DOHME CORP., Rahway, NJ (US); ALECTOS THERAPEUTICS, INC., Burnaby (CA)

(72) Inventors: Harold G. Selnick, Ambler, PA (US); Kun Liu, Needham, MA (US); Ernest J. McEachern, Burnaby (CA); Ramesh Kaul, Burnaby (CA); Zhongyong Wei, Beijing (CN); Yaode Wang, Beijing (CN); Jiang Chang, Beijing (CN)

(73) Assignees: ALECTOS THERAPEUTICS, INC., Burnaby, British Colombia (CA); MERCK SHARP & DOHME CORP., Rahway, NJ (US)

( * ) Notice: Subject to any disclaimer, the term of this patent is extended or adjusted under 35 U.S.C. 154(b) by 21 days.

(21) Appl. No.: 14/655,222

(22) PCT Filed: Dec. 20, 2013

(86) PCT No.: PCT/US2013/076768
§ 371 (c)(1),
(2) Date: Jun. 24, 2015

(87) PCT Pub. No.: WO2014/105662
PCT Pub. Date: Jul. 3, 2014

(65) Prior Publication Data
US 2016/0194337 A1    Jul. 7, 2016

(30) Foreign Application Priority Data
Dec. 24, 2012    (WO) ................ PCT/CN2012/087286

(51) Int. Cl.
| C07D 513/04 | (2006.01) |
| B65D 71/14 | (2006.01) |
| B65D 71/16 | (2006.01) |
| B65D 5/00 | (2006.01) |
| B65D 5/20 | (2006.01) |

(52) U.S. Cl.
CPC ........... *C07D 513/04* (2013.01); *B65D 5/005* (2013.01); *B65D 5/2057* (2013.01); *B65D 71/14* (2013.01); *B65D 71/16* (2013.01); *B65D 2571/0016* (2013.01); *B65D 2571/0029* (2013.01); *B65D 2571/0066* (2013.01); *B65D 2571/00716* (2013.01)

(58) Field of Classification Search
CPC .................................................. C07D 513/04
See application file for complete search history.

(56) References Cited

U.S. PATENT DOCUMENTS

| 8,884,023 B2 | 11/2014 | Donnely et al. |
| 8,901,087 B2 | 12/2014 | Chang et al. |
| 9,120,781 B2 | 9/2015 | Li et al. |
| 9,126,957 B2 | 9/2015 | Selnick et al. |
| 9,199,949 B2 | 12/2015 | Li et al. |
| 9,243,020 B2 | 1/2016 | Kaul et al. |
| 9,409,924 B2 | 8/2016 | Li et al. |
| 9,469,657 B2 * | 10/2016 | Donnelly ............. C07D 513/04 |
| 2008/0287375 A1 | 11/2008 | Vocadlo et al. |
| 2012/0276108 A1 | 11/2012 | Priebe |
| 2012/0316207 A1 | 12/2012 | Vocadlo et al. |
| 2014/0005191 A1 | 1/2014 | Coburn et al. |
| 2014/0107044 A1 | 4/2014 | McEachern et al. |
| 2014/0213584 A9 | 7/2014 | Coburn et al. |
| 2014/0275022 A1 | 9/2014 | Li et al. |
| 2015/0152127 A1 | 6/2015 | Selnick et al. |
| 2015/0218097 A1 | 8/2015 | McEachern et al. |
| 2015/0218147 A1 | 8/2015 | McEachern et al. |
| 2015/0274656 A1 | 10/2015 | McEachern et al. |
| 2015/0291620 A1 | 10/2015 | Kaul et al. |
| 2015/0299122 A1 | 10/2015 | McEachern et al. |

FOREIGN PATENT DOCUMENTS

| EP | 2748171 | 7/2014 |
| WO | WO02094796 | 11/2002 |
| WO | WO03039523 | 5/2003 |
| WO | WO2005072371 | 8/2005 |
| WO | WO2006092049 | 9/2006 |
| WO | WO2012126091 | 3/2011 |
| WO | WO201140640 | 11/2011 |
| WO | WO2012061927 | 11/2011 |
| WO | WO2012061971 | 5/2012 |
| WO | WO2012061972 | 5/2012 |
| WO | WO2012062157 | 5/2012 |
| WO | WO2012064680 A1 | 5/2012 |
| WO | WO2012083435 | 6/2012 |
| WO | WO2012129651 | 10/2012 |
| WO | 2012159262 | 11/2012 |
| WO | 2013025452 | 2/2013 |
| WO | WO2013028715 | 2/2013 |

OTHER PUBLICATIONS

Chemical Abstracts Registry No. 1374662-02-8, indexed in the Registry file on STN CAS online on May 29, 2012.*
International Search Report and Written Opinion for PCT/US2013/076768, dated Apr. 23, 2014, 13 pages.
International Search Report and Written Opinion of PCT/CN2012/087286, dated May 23, 2013, 17 pages.
Supplementary European Search Report for EP 13868947.6, dated May 17, 2016, 6 pages.

* cited by examiner

*Primary Examiner* — Laura L Stockton
(74) *Attorney, Agent, or Firm* — J. Eric Thies; John C. Todaro

(57) ABSTRACT

The invention provides compounds with enhanced permeability for selectively inhibiting glycosidases, prodrugs of the compounds, and pharmaceutical compositions including the compounds or prodrugs of the compounds. The invention also provides methods of treating diseases and disorders related to deficiency or overexpression of O-GlcNAcase, accumulation or deficiency of O-GlcNAc.

15 Claims, No Drawings

GLYCOSIDASE INHIBITORS AND USES THEREOF

CROSS REFERENCE TO RELATED APPLICATIONS

This application is a U.S. National Phase application under 35 U.S.C. § 371 of PCT Application No. PCT/US2013/076768, filed Dec. 20, 2013, which claims priority from International Application PCT/CN2012/087286, filed Dec. 24, 2012.

FIELD OF THE INVENTION

This application relates to compounds which inhibit glycosidases and uses thereof.

BACKGROUND OF THE INVENTION

A wide range of cellular proteins, both nuclear and cytoplasmic, are post-translationally modified by the addition of the monosaccharide 2-acetamido-2-deoxy-β-D-glucopyranoside (β-N-acetylglucosamine) which is attached via an O-glycosidic linkage.[1] This modification is generally referred to as O-linked N-acetylglucosamine or O-GlcNAc. The enzyme responsible for post-translationally linking β-N-acetylglucosamine (GlcNAc) to specific serine and threonine residues of numerous nucleocytoplasmic proteins is O-GlcNAc transferase (OGT).[2-5] A second enzyme, known as glycoprotein 2-acetamido-2-deoxy-β-D-glucopyranosidase (O-GlcNAcase)[6,7] removes this post-translational modification to liberate proteins making the O-GlcNAc-modification a dynamic cycle occurring several times during the lifetime of a protein.

O-GlcNAc-modified proteins regulate a wide range of vital cellular functions including, for example, transcription,[9-12] proteasomal degradation,[13] and cellular signaling.[14] O-GlcNAc is also found on many structural proteins.[15-17] For example, it has been found on a number of cytoskeletal proteins, including neurofilament proteins,[18,19] synapsins,[6,20] synapsin-specific clathrin assembly protein AP-3,[7] and ankyrinG.[14] O-GlcNAc modification has been found to be abundant in the brain.[21,22] It has also been found on proteins clearly implicated in the etiology of several diseases including Alzheimer's disease (AD) and cancer.

For example, it is well established that AD and a number of related tauopathies including Downs' syndrome, Pick's disease, Niemann-Pick Type C disease, and amyotrophic lateral sclerosis (ALS) are characterized, in part, by the development of neurofibrillary tangles (NFTs). These NFTs are aggregates of paired helical filaments (PHFs) and are composed of an abnormal form of the cytoskeletal protein "tau". Normally tau stabilizes a key cellular network of microtubules that is essential for distributing proteins and nutrients within neurons. In AD patients, however, tau becomes hyperphosphorylated, disrupting its normal functions, forming PHFs and ultimately aggregating to form NFTs. Six isoforms of tau are found in the human brain. In AD patients, all six isoforms of tau are found in NFTs, and all are markedly hyperphosphorylated.[23,24] Tau in healthy brain tissue bears only 2 or 3 phosphate groups, whereas those found in the brains of AD patients bear, on average, 8 phosphate groups.[25,26] A clear parallel between NFT levels in the brains of AD patients and the severity of dementia strongly supports a key role for tau dysfunction in AD.[27-29] The precise causes of this hyperphosphorylation of tau remain elusive. Accordingly, considerable effort has been dedicated toward: a) elucidating the molecular physiological basis of tau hyperphosphorylation;[30] and b) identifying strategies that could limit tau hyperphosphorylation in the hope that these might halt, or even reverse, the progression of Alzheimer's disease.[31-34] Thus far, several lines of evidence suggest that up-regulation of a number of kinases may be involved in hyperphosphorylation of tau,[21,35,36] although an alternative basis for this hyperphosphorylation has been advanced.[21]

In particular, it has emerged that phosphate levels of tau are regulated by the levels of O-GlcNAc on tau. The presence of O-GlcNAc on tau has stimulated studies that correlate O-GlcNAc levels with tau phosphorylation levels. The interest in this field stems from the observation that O-GlcNAc modification has been found to occur on many proteins at amino acid residues that are also known to be phosphorylated.[37-39] Consistent with this observation, it has been found that increases in phosphorylation levels result in decreased O-GlcNAc levels and conversely, increased O-GlcNAc levels correlate with decreased phosphorylation levels.[40] This reciprocal relationship between O-GlcNAc and phosphorylation has been termed the "Yin-Yang hypothesis"[41] and has gained strong biochemical support by the discovery that the enzyme OGT[4] forms a functional complex with phosphatases that act to remove phosphate groups from proteins.[42] Like phosphorylation, O-GlcNAc is a dynamic modification that can be removed and reinstalled several times during the lifespan of a protein. Suggestively, the gene encoding O-GlcNAcase has been mapped to a chromosomal locus that is linked to AD.[7,43] Hyperphosphorylated tau in human AD brains has markedly lower levels of O-GlcNAc than are found in healthy human brains.[21] It has been shown that O-GlcNAc levels of soluble tau protein from human brains affected with AD are markedly lower than those from healthy brain.[21] Furthermore, PHF from diseased brain was suggested to lack completely any O-GlcNAc modification whatsoever.[21] The molecular basis of this hypoglycosylation of tau is not known, although it may stem from increased activity of kinases and/or dysfunction of one of the enzymes involved in processing O-GlcNAc. Supporting this latter view, in both PC-12 neuronal cells and in brain tissue sections from mice, a nonselective N-acetylglucosamindase inhibitor was used to increase tau O-GlcNAc levels, whereupon it was observed that phosphorylation levels decreased.[21] The implication of these collective results is that by maintaining healthy O-GlcNAc levels in AD patients, such as by inhibiting the action of O-GlcNAcase, one should be able to block hyperphosphorylation of tau and all of the associated effects of tau hyperphosphorylation, including the formation of NFTs and downstream effects. However, because the proper functioning of the β-hexosaminidases is critical, any potential therapeutic intervention for the treatment of AD that blocks the action of O-GlcNAcase would have to avoid the concomitant inhibition of both hexosaminidases A and B.

Neurons do not store glucose and therefore the brain relies on glucose supplied by blood to maintain its essential metabolic functions. Notably, it has been shown that within brain, glucose uptake and metabolism decreases with aging.[44] Within the brains of AD patients marked decreases in glucose utilization occur and are thought to be a potential cause of neurodegeneration.[45] The basis for this decreased glucose supply in AD brain[46-48] is thought to stem from any of decreased glucose transport,[49,50] impaired insulin signaling,[51,52] and decreased blood flow.[53]

In light of this impaired glucose metabolism, it is worth noting that of all glucose entering into cells, 2-5% is shunted into the hexosamine biosynthetic pathway, thereby regulating cellular concentrations of the end product of this pathway, uridine diphosphate-N-acetylglucosamine (UDP-GlcNAc).[54] UDP-GlcNAc is a substrate of the nucleocytoplasmic enzyme O-GlcNAc transferase (OGT),[2-5] which acts to post-translationally add GlcNAc to specific serine and threonine residues of numerous nucleocytoplasmic proteins. OGT recognizes many of its substrates[55,59] and binding partners[42,57] through its tetratricopeptide repeat (TPR) domains.[58,59] As described above, O-GlcNAcase[6,7] removes this post-translational modification to liberate proteins making the O-GlcNAc-modification a dynamic cycle occurring several times during the lifetime of a protein.[8] O-GlcNAc has been found in several proteins on known phosphorylation sites,[10,38,39,60] including tau and neurofilaments.[61] Additionally, OGT shows unusual kinetic behaviour making it exquisitely sensitive to intracellular UDP-GlcNAc substrate concentrations and therefore glucose supply.[42] Consistent with the known properties of the hexosamine biosynthetic pathway, the enzymatic properties of OGT, and the reciprocal relationship between O-GlcNAc and phosphorylation, it has been shown that decreased glucose availability in brain leads to tau hyperphosphorylation.[45] Therefore the gradual impairment of glucose transport and metabolism, whatever its causes, leads to decreased O-GlcNAc and hyperphosphorylation of tau (and other proteins). Accordingly, the inhibition of O-GlcNAcase should compensate for the age related impairment of glucose metabolism within the brains of health individuals as well as patients suffering from AD or related neurodegenerative diseases.

These results suggest that a malfunction in the mechanisms regulating tau O-GlcNAc levels may be vitally important in the formation of NFTs and associated neurodegeneration. Good support for blocking tau hyperphosphorylation as a therapeutically useful intervention[62] comes from recent studies showing that when transgenic mice harbouring human tau are treated with kinase inhibitors, they do not develop typical motor defects[34] and, in another case,[33] show decreased levels of insoluble tau. These studies provide a clear link between lowering tau phosphorylation levels and alleviating AD-like behavioural symptoms in a murine model of this disease. Indeed, pharmacological modulation of tau hyperphosphorylation is widely recognized as a valid therapeutic strategy for treating AD and other neurodegenerative disorders.[63]

Small-molecule O-GlcNAcase inhibitors, to limit tau hyperphosphorylation, have been considered for treatment of AD and related tauopathies.[64] Specifically, the O-GlcNAcase inhibitor thiamet-G has been implicated in the reduction of tau phosphorylation in cultured PC-12 cells at pathologically relevant sites.[64] Moreover, oral administration of thiamet-G to healthy Sprague-Dawley rats has been implicated in reduced phosphorylation of tau at Thr231, Ser396 and Ser422 in both rat cortex and hippocampus.[64]

There is also a large body of evidence indicating that increased levels of O-GlcNAc protein modification provides protection against pathogenic effects of stress in cardiac tissue, including stress caused by ischemia, hemorrhage, hypervolemic shock, and calcium paradox. For example, activation of the hexosamine biosynthetic pathway (HBP) by administration of glucosamine has been demonstrated to exert a protective effect in animals models of ischemia/reperfusion,[65-71] trauma hemorrhage,[72-74] hypervolemic shock,[75] and calcium paradox.[65,76] Moreover, strong evidence indicates that these cardioprotective effects are mediated by elevated levels of protein O-GlcNAc modification.[65,66,68,71,73,76-79] There is also evidence that the O-GlcNAc modification plays a role in a variety of neurodegenerative diseases, including Parkinson's disease and Huntington's disease.[80]

Humans have three genes encoding enzymes that cleave terminal β-N-acetyl-glucosamine residues from glycoconjugates. The first of these encodes O-GlcNAcase. O-GlcNAcase is a member of family 84 of glycoside hydrolases that includes enzymes from organisms as diverse as prokaryotic pathogens to humans.[81,82] O-GlcNAcase acts to hydrolyse O-GlcNAc off of serine and threonine residues of post-translationally modified proteins.[1,67,83,84] Consistent with the presence of O-GlcNAc on many intracellular proteins, the enzyme O-GlcNAcase appears to have a role in the etiology of several diseases including type II diabetes,[14,85] AD,[16,21,86] and cancer.[22,87] Although O-GlcNAcase was likely isolated earlier on,[18,19] about 20 years elapsed before its biochemical role in acting to cleave O-GlcNAc from serine and threonine residues of proteins was understood.[6] More recently O-GlcNAcase has been cloned,[7] partially characterized,[20] and suggested to have additional activity as a histone acetyltransferase.[20] However, little was known about the catalytic mechanism of this enzyme.

The other two genes, HEXA and HEXB, encode enzymes catalyzing the hydrolytic cleavage of terminal β-N-acetyl-glucosamine residues from glycoconjugates. The gene products of HEXA and HEXB predominantly yield two dimeric isozymes, hexosaminidase A and hexosaminidase B, respectively. Hexosaminidase A (αβ), a heterodimeric isozyme, is composed of an α- and a β-subunit. Hexosaminidase B (ββ), a homodimeric isozyme, is composed of two β-subunits. The two subunits, α- and β-, bear a high level of sequence identity. Both of these enzymes are classified as members of family 20 of glycoside hydrolases and are normally localized within lysosomes. The proper functioning of these lysosomal β-hexosaminidases is critical for human development, a fact that is underscored by the tragic genetic illnesses, Tay-Sach's and Sandhoff diseases which stem from a dysfunction in, respectively, hexosaminidase A and hexosaminidase B.[88] These enzymatic deficiencies cause an accumulation of glycolipids and glycoconjugates in the lysosomes resulting in neurological impairment and deformation. The deleterious effects of accumulation of gangliosides at the organismal level are still being uncovered.[89]

As a result of the biological importance of these 3-N-acetyl-glucosaminidases, small molecule inhibitors of glycosidases[90-93] have received a great deal of attention,[94] both as tools for elucidating the role of these enzymes in biological processes and in developing potential therapeutic applications. The control of glycosidase function using small molecules offers several advantages over genetic knockout studies including the ability to rapidly vary doses or to entirely withdraw treatment.

However, a major challenge in developing inhibitors for blocking the function of mammalian glycosidases, including O-GlcNAcase, is the large number of functionally related enzymes present in tissues of higher eukaryotes. Accordingly, the use of non-selective inhibitors in studying the cellular and organismal physiological role of one particular enzyme is complicated because complex phenotypes arise from the concomitant inhibition of such functionally related enzymes. In the case of β-N-acetylglucosaminidases, many compounds that act to block O-GlcNAcase function are non-specific and act potently to inhibit the lysosomal β-hexosaminidases.

A few of the better characterized inhibitors of β-N-acetyl-glucosaminidases which have been used in studies of O-GlcNAc post-translational modification within both cells and tissues are streptozotocin (STZ), 2'-methyl-α-D-glucopyrano-[2,1-d]-Δ2'-thiazoline (NAG-thiazoline) and O-(2-acetamido-2-deoxy-D-glucopyranosylidene)amino N-phenyl-carbamate (PUGNAc).[14,95-98]

STZ has long been used as a diabetogenic compound because it has a particularly detrimental effect on β-islet cells.[99] STZ exerts its cytotoxic effects through both the alkylation of cellular DNA[99,100] as well as the generation of radical species including nitric oxide.[101] The resulting DNA strand breakage promotes the activation of poly(ADP-ribose) polymerase (PARP)[102] with the net effect of depleting cellular NAD+ levels and, ultimately, leading to cell death.[103,104] Other investigators have proposed instead that STZ toxicity is a consequence of the irreversible inhibition of O-GlcNAcase, which is highly expressed within β-islet cells.[95,105] This hypothesis has, however, been brought into question by two independent research groups.[106,107] Because cellular O-GlcNAc levels on proteins increase in response to many forms of cellular stress[108] it seems possible that STZ results in increased O-GlcNAc-modification levels on proteins by inducing cellular stress rather than through any specific and direct action on O-GlcNAcase. Indeed, Hanover and coworkers have shown that STZ functions as a poor and somewhat selective inhibitor of O-GlcNAcase[109] and although it has been proposed by others that STZ acts to irreversibly inhibit O-GlcNAcase,[110] there has been no clear demonstration of this mode of action. More recently, it has been shown that STZ does not irreversibly inhibit O-GlcNAcase.[111]

NAG-thiazoline has been found to be a potent inhibitor of family 20 hexosaminidases,[93,112] and more recently, the family 84 O-GlcNAcases.[111] Despite its potency, a downside to using NAG-thiazoline in a complex biological context is that it lacks selectivity and therefore perturbs multiple cellular processes.

PUGNAc is another compound that suffers from the same problem of lack of selectivity, yet has enjoyed use as an inhibitor of both human O-GlcNAcase[6,113] and the family 20 human β-hexosaminidases.[114] This molecule, developed by Vasella and coworkers, was found to be a potent competitive inhibitor of the β-N-acetyl-glucosaminidases from *Canavalia ensiformis, Mucor rouxii*, and the β-hexosaminidase from bovine kidney.[91] It has been demonstrated that administration of PUGNAc in a rat model of trauma hemorrhage decreases circulating levels of the pro-inflammatory cytokines TNF-α and IL-6.[115] It has also been shown that administration of PUGNAc in a cell-based model of lymphocyte activation decreases production of the cytokine IL-2.[116] Subsequent studies have indicated that PUGNAc can be used in an animal model to reduce myocardial infarct size after left coronary artery occlusions.[117] Of particular significance is the fact that elevation of O-GlcNAc levels by administration of PUGNAc, an inhibitor of O-GlcNAcase, in a rat model of trauma hemorrhage improves cardiac function.[115,118] In addition, elevation of O-GlcNAc levels by treatment with PUGNAc in a cellular model of ischemia/reperfusion injury using neonatal rat ventricular myocytes improved cell viability and reduced necrosis and apoptosis compared to untreated cells.[119]

More recently, it has been suggested that the selective O-GlcNAcase inhibitor NButGT exhibits protective activity in cell-based models of ischemia/reperfusion and cellular stresses, including oxidative stress.[120] This study suggests the use of O-GlcNAcase inhibitors to elevate protein O-GlcNAc levels and thereby prevent the pathogenic effects of stress in cardiac tissue.

International patent applications PCT/CA2006/000300, filed 1 Mar. 2006, published under No. WO 2006/092049 on 8 Sep. 2006; PCT/CA2007/001554, filed 31 Aug. 2007, published under No. WO 2008/025170 on 6 Mar. 2008; PCT/CA2009/001087, filed 31 Jul. 2009, published under No. WO 2010/012106 on 4 Feb. 2010; PCT/CA2009/001088, filed 31 Jul. 2009, published under WO 2010/012107 on 4 Feb. 2010; PCT/CA2009/001302, filed 16 Sep. 2009, published under WO 2010/037207 on 8 Apr. 2010; PCT/CA2011/000548, filed 10 May 2011, published under No. WO 2011/140640 on 17 Nov. 2011; PCT/CA/2011/001241, filed 8 Nov. 2011, published under WO 2012/061927 on 18 May 2012; PCT/US2011/059668, filed 8 Nov. 2011, published under WO 2012/064680 on 18 May 2012; and PCT/CA2011/001397, filed 21 Dec. 2011, published under WO 2012/083435 on 28 Jun. 2012, describe selective inhibitors of O-GlcNAcase.

SUMMARY OF THE INVENTION

The invention provides, in part, compounds for inhibiting glycosidases, prodrugs of the compounds, uses of the compounds and the prodrugs, pharmaceutical compositions including the compounds or prodrugs of the compounds, and methods of treating diseases and disorders related to deficiency or overexpression of O-GlcNAcase, and/or accumulation or deficiency of O-GlcNAc.

In one aspect, the invention provides a compound of Formula (I)

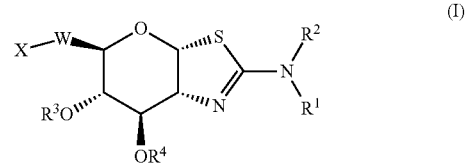

and pharmaceutically acceptable salts, prodrugs, solvates and enantiomeric forms thereof:
wherein,
$R^1$ and $R^2$ are each independently hydrogen, C1-6alkyl, C2-6alkenyl or C2-6alkynyl wherein the alkyl, alkenyl or alkynyl are optionally substituted with one up to the maximum number of substituents with one or more of fluoro, OH, or methyl;
$R^3$ and $R^4$ are each independently hydrogen, or C1-6acyl;
W is (1) —$(CH_2)_m$—$C(R^5R^6)$—* wherein m is 1-3, $R^5$ and $R^6$ are each independently hydrogen, C1-3alkyl, —OH, halo, or —$CF_3$, and the * represents the point of attachment to the tetrahydropyran ring;
(2) —$(CH_2)_n$—CH=$C(R^7)$—* wherein n is 0-3, $R^7$ is hydrogen or —$CF_3$, and the * represents the point of attachment to the tetrahydropyran ring;
(3) —$(CH_2)_p$—$S(O)_2$—$CH_2$—* wherein p is 0-1, and the * represents the point of attachment to the tetrahydropyran ring; or
(4) —$(CH_2)_q$—S—$CH_2$—* wherein q is 0-1 and the * represents the point of attachment to the tetrahydropyran ring; and
X is (1)

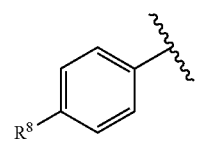

wherein $R^8$ is hydrogen or C1-3alkoxy;
(2) —C(O)—O—$R^9$ wherein $R^9$ is hydrogen, C1-3alkyl, C1-3alkenyl or C1-3alkynyl; or (3) —C(O)—NR$^{10}$R$^{11}$ wherein R$^{10}$ and R$^{11}$ are each independently hydrogen, C1-3alkyl, C1-3alkenyl or C1-3alkynyl.

In another aspect, the invention provides a compound of the Formula (II)

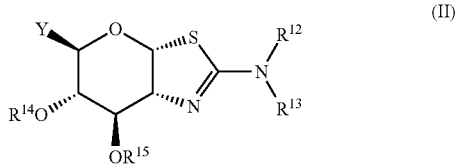

(II)

and pharmaceutically acceptable salts, prodrugs, solvates and enantiomeric forms thereof: wherein
R$^{12}$ and R$^{13}$ are each independently hydrogen, C1-6alkyl, C2-6alkenyl, C2-6alkynyl, wherein the alkyl, alkenyl and alkynyl are optionally substituted from one up to the maximum number of substituents with one or more of fluoro, OH, or methyl;
R$^{14}$ and R$^{15}$ are each hydrogen;
Y is —CN, —CH$_2$—CN, —C≡CH, —CH$_2$Cl, —C(CH$_3$)=CH$_2$, —C(CF$_3$)=CH$_2$, or —(CH$_2$)$_2$NR$^{16}$R$^{17}$ wherein R$^{16}$ and R$^{17}$ are each independently hydrogen or C1-3alkyl, —C(C1-3alkyl)$_2$-Cl, or —C(=CH$_2$)—C1-3alkyl, and wherein the C1-3alkyl, —C(C1-3alkyl)$_2$-Cl, or —C(=CH$_2$)—C1-3alkyl are optionally substituted from one up to the maximum number of substituents with fluoro.

In another aspect, the invention provides a compound of the Formula (III)

(III)

and pharmaceutically acceptable salts, prodrugs, solvates and enantiomeric forms thereof: wherein,
R$^{18}$ and R$^{19}$ are each independently hydrogen, C1-6alkyl, C2-6alkenyl, or C2-6alkynyl, wherein the alkyl, alkenyl and alkynyl are optionally substituted from one up to the maximum number of substituents with one or more of fluoro, OH, or methyl.
R$^{20}$ and R$^{21}$ are each hydrogen;
R$^{22}$ is
(1) C1-3alkyl, —OH, C1-3alkoxy, wherein the alkyl and alkoxy are optionally substituted from one up to the maximum number of substituents with one or more of fluoro, —OH, or methyl; or
(2) NR$^{23}$R$^{24}$, wherein R$^{23}$ is hydrogen or C1-C3alkyl wherein the alkyl is optionally substituted from one up to the maximum number of substituents with one or more of fluoro, OH, or methyl, and R$^{24}$ is C1-3alkyl, C1-3alkoxy, or cyclopropyl, wherein the alkyl, alkoxy and cyclopropyl are optionally substituted from one up to the maximum number of substituents with one or more of fluoro, OH, or methyl.

In alternative embodiments, the compound may be a prodrug; the compound may selectively inhibit an O-glycoprotein 2-acetamido-2-deoxy-β-D-glucopyranosidase (O-GlcNAcase); the compound may selectively bind an O-GlcNAcase (e.g., a mammalian O-GlcNAcase); the compound may selectively inhibit the cleavage of a 2-acetamido-2-deoxy-β-D-glucopyranoside (O-GlcNAc); the compound may not substantially inhibit a mammalian β-hexosaminidase.

In alternative embodiments, a compound according to Formula (I), Formula (II), Formula (III) may have enhanced permeability.

In another aspect, the invention provides a pharmaceutical composition including a compound according to the invention, and pharmaceutically acceptable salts, prodrugs, and enantiomeric forms thereof in combination with a pharmaceutically acceptable carrier.

In another aspect, the invention provides methods of selectively inhibiting an O-GlcNAcase, or of inhibiting an O-GlcNAcase in a subject in need thereof, or of increasing the level of O-GlcNAc, or of potentially treating Alzheimer's disease and related tauopathies, amyotrophic lateral sclerosis, glaucoma, schizophrenia, Huntington's disease, Parkinson's disease, mild cognitive impairment (MCI), neuropathy and cancer or stress, in a subject in need thereof, by administering to the subject an effective amount of a compound of Formulas (I), (II), or (III) and pharmaceutically acceptable salts, prodrugs, and enantiomeric forms thereof.

In another aspect, the invention provides a method for screening for a selective inhibitor of an O-GlcNAcase, by
a) contacting a first sample with a test compound;
b) contacting a second sample with a compound of Formulas (I), (II) or (III) or a pharmaceutically acceptable salt thereof;
c) determining the level of inhibition of the O-GlcNAcase in the first and second samples, where the test compound is a selective inhibitor of a O-GlcNAcase if the test compound exhibits the same or greater inhibition of the O-GlcNAcase when compared to the compound of Formulas (I), (II) or (III).

In alternative aspects, the invention provides methods of synthesis to prepare a compound as described herein, or a pharmaceutically acceptable salt thereof.

This summary of the invention does not necessarily describe all features of the invention.

DETAILED DESCRIPTION OF THE INVENTION

The invention provides, in part, novel compounds that are capable of inhibiting an O-glycoprotein 2-acetamido-2-deoxy-β-D-glucopyranosidase (O-GlcNAcase). In some embodiments, the O-GlcNAcase may be a mammalian O-GlcNAcase, such as a rat, mouse or human O-GlcNAcase.

In some embodiments, one or more of the compounds according to the invention may exhibit enhanced permeability. Permeability can be assessed using a variety of standard experimental techniques, including without limitation in situ perfusion, ex vivo tissue diffusion, in vitro cell monolayers (e.g. Caco-2 cells, MDCK cells, LLC-PK1 cells), and artificial cell membranes (e.g. PAMPA assay); suitable techniques for measuring effective permeability ($P_{eff}$) or apparent peameability ($P_{app}$) are reviewed for example by Volpe in *The AAPS Journal*, 2010, 12(4), 670-678. In some embodiments, one or more of the compounds according to the invention may show enhanced permeability when tested in one or more of these assays for determining Pear or $P_{app}$. In some embodiments, a compound that exhibits enhanced permeability may exhibit greater oral absorption. In some embodiments, a compound that exhibits enhanced permeability may exhibit greater brain penetrance when administered in vivo. In some embodiments, a compound that exhibits enhanced permeability may achieve higher brain concentrations when administered in vivo. In some embodiments, a compound that exhibits enhanced permeability may exhibit a higher brain/plasma concentration ratio when administered in vivo. In some embodiments, "enhanced permeability" means an increase in measured $P_{eff}$ or $P_{app}$ by any value between 10% and 100%, or of any integer value between 10% and 100%, for example, 10%, 20%, 30%, 40%, 50%, 60%, 70%, 80%, 90%, 100%, or over 100%, or an increase by 1-fold, 2-fold, or 3-fold, or more, as compared to a suitable reference compound disclosed in for example WO 2006/092049 or WO 2008/025170. A suitable reference compound may be, for example, (3aR,5R,6S,7R,7aR)-5-(hydroxymethyl)-2-propyl-5,6,7,7a-tetrahydro-3aH-pyrano[3,2-d]thiazole-6,7-diol, or (3aR,5R,6S,7R,7aR)-2-(ethylamino)-5-(hydroxymethyl)-5,6,7,7a-tetrahydro-3aH-pyrano[3,2-d]thiazole-6,7-diol, or (3aR,5R,6S,7R,7aR)-2-(dimethylamino)-5-(hydroxymethyl)-5,6,7,7a-tetrahydro-3aH-pyrano[3,2-d]thiazole-6,7-diol. In some embodiments, "enhanced permeability" means a measurable $P_{app}$ value (i.e. a value greater than zero) in the assay described below for determination of $P_{app}$ in LLC-PK1 cells. In some embodiments, "enhanced permeability" means a $P_{app}$ value greater than $2\times10^{-6}$ cm/s in the assay described below for determination of $P_{app}$ in LLC-PK1 cells. In alternative embodiments, "enhanced permeability" means a $P_{app}$ value in the range $2\times10^{-6}$ cm/s to $35\times10^{-6}$ cm/s in the assay described below for determination of $P_{app}$ in LLC-PK1 cells.

In some embodiments, a compound according to the invention may exhibit superior selectivity in inhibiting an O-GlcNAcase. In some embodiments, one or more of the compounds according to the invention may be more selective for an O-GlcNAcase over a β-hexosaminidase. In some embodiments, one or more of the compounds may selectively inhibit the activity of a mammalian O-GlcNAcase over a mammalian β-hexosaminidase. In some embodiments, a selective inhibitor of an O-GlcNAcase may not substantially inhibit a β-hexosaminidase. In some embodiments, the β-hexosaminidase may be a mammalian β-hexosaminidase, such as a rat, mouse or human β-hexosaminidase. A compound that "selectively" inhibits an O-GlcNAcase is a compound that may inhibit the activity or biological function of an O-GlcNAcase, but may not substantially inhibit the activity or biological function of a β-hexosaminidase. For example, in some embodiments, a selective inhibitor of an O-GlcNAcase may selectively inhibit the cleavage of 2-acetamido-2-deoxy-β-D-glucopyranoside (O-GlcNAc) from polypeptides. In some embodiments, a selective inhibitor of an O-GlcNAcase may selectively bind to an O-GlcNAcase. In some embodiments, a selective inhibitor of an O-GlcNAcase may inhibit hyperphosphorylation of a tau protein and/or inhibit formations of NFTs. By "inhibit," "inhibition" or "inhibiting" means a decrease by any value between 10% and 90%, or of any integer value between 30% and 60%, or over 100%, or a decrease by 1-fold, 2-fold, 5-fold, 10-fold or more. It is to be understood that the inhibiting does not require full inhibition. In some embodiments, a selective inhibitor of an O-GlcNAcase may elevate or enhance O-GlcNAc levels e.g., O-GlcNAc-modified polypeptide or protein levels, in cells, tissues, or organs (e.g., in brain, muscle, or heart (cardiac) tissue) and in animals. By "elevating" or "enhancing" is meant an increase by any value between 10% and 90%, or of any integer value between 30% and 60%, or over 100%, or an increase by 1-fold, 2-fold, 5-fold, 10-fold, 15-fold, 25-fold, 50-fold, 100-fold or more. In some embodiments, a selective inhibitor of an O-GlcNAcase may exhibit a selectivity ratio, as described herein, in the range 10 to 100000, or in the range 100 to 100000, or in the range 1000 to 100000, or at least 10, 20, 50, 100, 200, 500, 1000, 1500, 2000, 2500, 3000, 3500, 4000, 4500, 5000, 6000, 7000, 10,000, 25,000, 50,000, 75,000, or any value within or about the described range.

One or more of the compounds of the present invention may elevate O-GlcNAc levels on O-GlcNAc-modified polypeptides or proteins in vive specifically via interaction with an O-GlcNAcase enzyme, and may be effective in treating conditions which require or respond to inhibition of O-GlcNAcase activity.

In some embodiments, one or more of the compounds of the present invention may be useful as agents that produce a decrease in tau phosphorylation and NFT formation. In some embodiments, one or more of the compounds may therefore be useful to treat Alzheimer's disease and related tauopathies. In some embodiments, one or more of the compounds may thus be capable of treating Alzheimer's disease and related tauopathies by lowering tau phosphorylation and reducing NFT formation as a result of increasing tau O-GlcNAc levels. In some embodiments, one or more of the compounds may produce an increase in levels of O-GlcNAc modification on O-GlcNAc-modified polypeptides or proteins, and may therefore be useful for treatment of disorders responsive to such increases in O-GlcNAc modification; these disorders may include, without limitation, neurodegenerative, inflammatory, cardiovascular, and immunoregulatory diseases. In some embodiments, a compound may also be useful as a result of other biological activities related to its ability to inhibit the activity of glycosidase enzymes. In alternative embodiments, one or more of the compounds of the invention may be valuable tools in studying the physiological role of O-GlcNAc at the cellular and organismal level.

In alternative embodiments, the invention provides methods of enhancing or elevating levels of protein O-GlcNAc modification in animal subjects, such as, veterinary and human subjects. In alternative embodiments, the invention provides methods of selectively inhibiting an O-GlcNAcase enzyme in animal subjects, such as, veterinary and human subjects. In alternative embodiments, the invention provides methods of inhibiting phosphorylation of tau polypeptides, or inhibiting formation of NFTs, in animal subjects, such as, veterinary and human subjects.

In one aspect, the invention provides compounds of the Formula (I) and pharmaceutically acceptable salts, prodrugs, solvates and enantiomeric forms thereof:

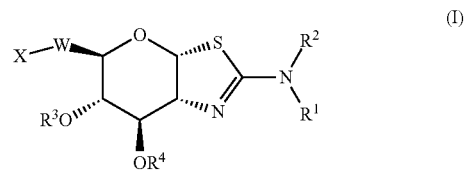

(I)

wherein,
$R^1$ and $R^2$ are each independently hydrogen, C1-6alkyl, C2-6alkenyl or C2-6alkynyl wherein the alkyl, alkenyl or alkynyl are optionally substituted with one up to the maximum number of substituents with one or more of fluoro, OH, or methyl; $R^3$ and $R^4$ are each independently hydrogen, or C1-6acyl;

W is (1) —(CH$_2$)$_m$—C(R$^5$R$^6$)—* wherein m is 1-3, R$^5$ and R$^6$ are each independently hydrogen, C1-3alkyl, —OH, halo (e.g., fluoro, bromo or chloro), or —CF$_3$, and the * represents the point of attachment to the tetrahydropyran ring;
(2) —(CH$_2$)$_n$—CH=C(R$^7$)—* wherein n is 0-3, R$^7$ is hydrogen or —CF$_3$, and the * represents the point of attachment to the tetrahydropyran ring;
(3) —(CH$_2$)$_p$—S(O)$_2$—CH$_2$—* wherein p is 0-1, and the * represents the point of attachment to the tetrahydropyran ring; or
(4) —(CH$_2$)$_q$—S—CH$_2$—* wherein q is 0-1 and the * represents the point of attachment to the tetrahydropyran ring; and
X is
(1)

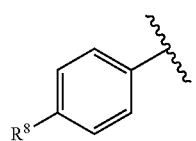

wherein R$^8$ is hydrogen or C1-3alkoxy,
(2) —C(O)—O—R$^9$ wherein R$^9$ is hydrogen, C1-3alkyl, C1-3alkenyl or C1-3alkynyl; or
(3) —C(O)—NR$^{10}$R$^{11}$ wherein R$^{10}$ and R$^{11}$ are each independently hydrogen, C1-3alkyl, C1-3alkenyl or C1-3alkynyl.

In an embodiment of the compounds of Formula (I), when W is (1) —(CH$_2$)$_m$—C(R$^5$R$^6$)—* wherein m is 1-3, R$^5$ and R$^6$ are each independently hydrogen, C1-3alkyl, —OH, halo, the halo is fluoro.

In an embodiment of the compounds of Formula (I), R$^1$ and R$^2$ are each hydrogen or methyl.

In another embodiment of the compounds of Formula (I), R$^3$ and R$^4$ are hydrogen.

In another embodiment of the compounds of Formula (I), wherein W is —(CH$_2$)$_m$—C(R$^5$R$^6$)—*, m is 1-3, R$^5$ and R$^6$ are each independently hydrogen, C1-3alkyl, —OH, halo, or —CF$_3$, and the * represents the point of attachment to the tetrahydropyran ring.

In another embodiment of the compounds of Formula (I) or a pharmaceutically acceptable salt thereof, wherein W is —(CH$_2$)$_n$—CH=C(R$^7$)—*, n is 0-3, R$^7$ is hydrogen or —CF$_3$, and the * represents the point of attachment to the tetrahydropyran ring.

In another embodiment of the compounds of Formula (I) wherein W is —(CH$_2$)$_p$—S(O)$_2$—CH$_2$-*, p is 0-1 and the * represents the point of attachment to the tetrahydropyran ring, or W is —S—(CH$_2$)$_q$—S—CH$_2$—*, wherein q is 0-1 and the * represents the point of attachment to the tetrahydropyran ring.

In another embodiment of the compounds of Formula (I), X is

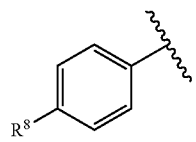

wherein R$^8$ is hydrogen or C1-3alkoxy.
In another embodiment of the compounds of Formula (I), X is —C(O)—O—R$^9$ wherein R$^9$ is hydrogen or C1-3alkyl.

In another embodiment of the compounds of Formula (I), wherein X is —C(O)—NR$^{10}$R$^{11}$R$^{10}$ and R$^{11}$ are each independently hydrogen or C1-3alkyl.

In another embodiment of the compounds of Formula (I), R$^1$ is hydrogen and R$^2$ is methyl, or R$^1$ is methyl and R$^2$ is hydrogen or R$^1$ and R$^2$ are methyl; R$^3$ and R$^4$ are hydrogen; W is —(CH$_2$)$_m$—C(R$^5$R$^6$)—* wherein m is 1-2, R$^5$ and R$^6$ are each independently hydrogen, —OH, fluoro, or —CF$_3$, the * represents the point of attachment to the tetrahydropyran ring; and
X is

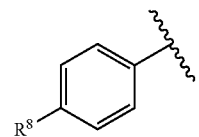

wherein R$^8$ is hydrogen or —OCH$_3$.

In another embodiment of the compounds of Formula (I), R$^1$ is hydrogen and R$^2$ is methyl, or R$^1$ is methyl and R$^2$ is hydrogen, or R$^1$ and R$^2$ are both methyl; R$^3$ and R$^4$ are hydrogen; W is —(CH$_2$)$_m$—C(R$^5$R$^6$)—* wherein m is 1-2, R$^5$ and R$^6$ are each independently hydrogen, —OH, fluoro, or —CF$_3$, the * represents the point of attachment to the tetrahydropyran ring; and X is —C(O)—O—R$^9$ wherein R$^9$ is hydrogen or C1-3alkyl.

In another embodiment of the compounds of Formula (I), R$^1$ is hydrogen and R$^2$ is methyl, or R$^1$ is methyl and R$^2$ is hydrogen, or R$^1$ and R$^2$ are both methyl; R$^3$ and R$^4$ are hydrogen; W is —(CH$_2$)$_m$—C(R$^5$R$^6$)—* wherein m is 0-3, R$^5$ and R$^6$ are each independently hydrogen, —OH, fluoro, or —CF$_3$, and the * represents the point of attachment to the tetrahydropyran ring; and X is —C(O)—NR$^{10}$R$^{11}$ wherein R$^{10}$ and R$^{11}$ are each independently hydrogen or C1-3alkyl.

In another embodiment of the compounds of Formula (I), R$^1$ is hydrogen and R$^2$ is methyl, or R$^1$ is methyl and R$^2$ is hydrogen, or R$^1$ and R$^2$ are both methyl; W is —(CH$_2$)$_n$—CH=C(R$^7$)—* wherein n is 0-1, R$^7$ is hydrogen or —CF$_3$, and the * represents the point of attachment to the tetrahydropyran ring; and
X is
(1)

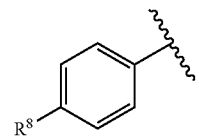

wherein R$^8$ is hydrogen or C1-3alkoxy, or
(2) —(O)—O—R$^9$ wherein R$^9$ is hydrogen or C1-3alkyl.

In another embodiment of the compounds of Formula (I), the compound is selected from the group consisting of compounds 1-10, 12, 13, 17-30, 33, 34 and 59-62.

As will be appreciated by a person skilled in the art, Formula (I) above may also be represented alternatively as follows:

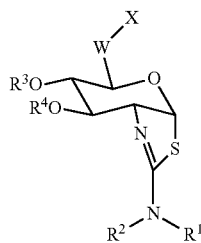

In another aspect, the invention provides compounds of the Formula (II) and pharmaceutically acceptable salts, prodrugs, solvates and enantiomeric forms thereof:

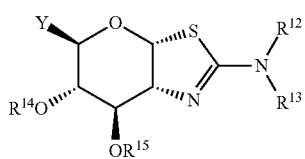

wherein $R^{12}$ and $R^{13}$ are each independently hydrogen, C1-6alkyl, C2-6alkenyl, C2-6alkynyl, wherein the alkyl, alkenyl and alkynyl are optionally substituted from one up to the maximum number of substituents with one or more of fluoro, OH, or methyl;

$R^{14}$ and $R^{15}$ are each hydrogen;

Y is —CN, —CH$_2$—CN, —C≡CH, —CH$_2$Cl, —C(CH$_3$)=CH$_2$, —C(CF$_3$)=CH$_2$, or —(CH$_2$)$_2$NR$^{16}$R$^{17}$ wherein $R^{16}$ and $R^{17}$ are each independently hydrogen or C1-3alkyl, —C(C1-3alkyl)$_2$-Cl, or —C(=CH$_2$)—C1-3alkyl, and wherein the C1-3alkyl, —C(C1-3alkyl)$_2$-Cl, or —C(=CH$_2$)—C1-3alkyl are optionally substituted from one up to the maximum number of substituents with fluoro.

In another embodiment of the compounds of Formula (II), $R^{12}$ is hydrogen and $R^{13}$ is methyl or allyl, or $R^{12}$ is methyl or allyl and $R^{13}$ is hydrogen, or $R^{12}$ and $R^{13}$ are both methyl.

In another embodiment of the compounds of Formula (II), the compound is selected from the group consisting of compounds (example nos.) 11, 13-16, 31, 32, 39-40, and 54-58.

As will be appreciated by a person skilled in the art, Formula (II) above may also be represented alternatively as follows:

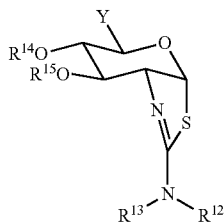

In another aspect, the invention provides compounds of the Formula (III) and pharmaceutically acceptable salts, prodrugs, solvates and enantiomeric forms thereof:

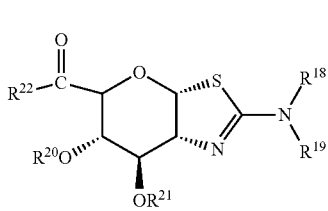

wherein, $R^{18}$ and $R^{19}$ are each independently hydrogen, C1-6alkyl, C2-6alkenyl, or C2-6alkynyl, wherein the alkyl, alkenyl and alkynyl are optionally substituted from one up to the maximum number of substituents with one or more of fluoro, OH, or methyl.

$R^{20}$ and $R^{21}$ are each hydrogen;

$R^{22}$ is (1) C1-3alkyl, —OH, C1-3alkoxy, wherein the alkyl and alkoxy are optionally substituted from one up to the maximum number of substituents with one or more of fluoro, —OH, or methyl; or (2) NR$^{23}$R$^{24}$, wherein R is hydrogen or C1-C3alkyl wherein the alkyl is optionally substituted from one up to the maximum number of substituents with one or more of fluoro, OH, or methyl, and $R^{24}$ is C1-3alkyl, C1-3alkoxy, or cyclopropyl, wherein the alkyl, alkoxy and cyclopropyl are optionally substituted from one up to the maximum number of substituents with one or more of fluoro, OH, or methyl.

In an embodiment of the compounds of Formula (III), the compound is selected from the group consisting of compounds (Example Nos.) 35-38, and 42-53.

As will be appreciated by a person skilled in the art, Formula (III) above may also be represented alternatively as follows:

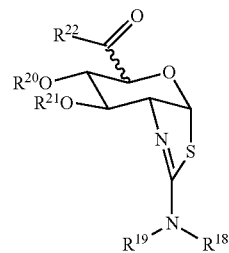

As used herein the singular forms "a", "and", and "the" include plural referents unless the context clearly dictates otherwise. For example, "a compound" refers to one or more of such compounds, while "the enzyme" includes a particular enzyme as well as other family members and equivalents thereof as known to those skilled in the art.

Throughout this application, it is contemplated that the term "compound" or "compounds" refers to the compounds discussed herein and includes precursors and derivatives of the compounds, including acyl-protected derivatives, and pharmaceutically acceptable salts of the compounds, precursors, and derivatives. The invention also includes prodrugs of the compounds, pharmaceutical compositions including the compounds and a pharmaceutically acceptable carrier, and pharmaceutical compositions including prodrugs of the compounds and a pharmaceutically acceptable carrier.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

"Alkyl" refers to a straight or branched hydrocarbon chain group consisting solely of carbon and hydrogen atoms, containing no unsaturation and including, for example, from one to ten carbon atoms, such as 1, 2, 3, 4, 5, 6, 7, 8, 9, or 10 carbon atoms, and which is attached to the rest of the molecule by a single bond. In alternative embodiments, the alkyl group may contain from one to eight carbon atoms, such as 1, 2, 3, 4, 5, 6, 7, or 8 carbon atoms. In alternative embodiments, the alkyl group may contain from one to six carbon atoms, such as 1, 2, 3, 4, 5, or 6 carbon atoms. In alternative embodiments, the alkyl group may contain from one to three carbon atoms, such as 1, 2, or 3 carbon atoms. Unless stated otherwise specifically in the specification, the alkyl group may be optionally substituted by one or more substituents as described herein. Unless stated otherwise specifically herein, it is understood that the substitution can occur on any carbon of the alkyl group.

"Alkenyl" refers to a straight or branched hydrocarbon chain group consisting solely of carbon and hydrogen atoms, containing at least one double bond and including, for example, from two to ten carbon atoms, such as 2, 3, 4, 5, 6, 7, 8, 9, or 10 carbon atoms, and which is attached to the rest of the molecule by a single bond or a double bond. In alternative embodiments, the alkenyl group may contain from two to eight carbon atoms, such as 2, 3, 4, 5, 6, 7, or 8 carbon atoms. In alternative embodiments, the alkenyl group may contain from three to six carbon atoms, such as 3, 4, 5, or 6 carbon atoms. In alternative embodiments, the alkenyl group may contain from one to three carbon atoms, such as 1, 2, or 3 carbon atoms. Unless stated otherwise specifically in the specification, the alkenyl group may be optionally substituted by one or more substituents as described herein. Unless stated otherwise specifically herein, it is understood that the substitution can occur on any carbon of the alkenyl group.

"Alkynyl" refers to a straight or branched hydrocarbon chain group consisting solely of carbon and hydrogen atoms, containing at least one triple bond and including, for example, from two to ten carbon atoms. In alternative embodiments, the alkynyl group may contain from two to eight carbon atoms, such as 2, 3, 4, 5, 6, 7, or 8 carbon atoms. In alternative embodiments, the alkynyl group may contain from three to six carbon atoms, such as 3, 4, 5, or 6 carbon atoms. In alternative embodiments, the alkynyl group may contain from one to three carbon atoms, such as 1, 2, or 3 carbon atoms. Unless stated otherwise specifically in the specification, the alkynyl group may be optionally substituted by one or more substituents as described herein.

"Alkoxy" refers to a group of the formula —$OR_a$, where $R_a$ is a $C_{1-10}$ alkyl, a $C_{1-6}$ alkyl group, or a $C_{1-3}$ alkyl group as described herein. The alkyl group(s) may be optionally substituted as described herein.

"Acyl" refers to a group of the formula —C(=O)$R_b$, where $R_b$ is a C1-10alkyl, or a C1-6alkyl group.

"Optional" or "optionally" means that the subsequently described event of circumstances may or may not occur, and that the description includes instances where said event or circumstance occurs one or more times and instances in which it does not. For example, "optionally substituted alkyl" means that the alkyl group may or may not be substituted and that the description includes both substituted alkyl groups and alkyl groups having no substitution, and that said alkyl groups may be substituted one or more times. Examples of optionally substituted alkyl groups include, without limitation, methyl, ethyl, propyl, etc. and also include cyclopropyl, etc.; examples of optionally substituted alkenyl groups include allyl, crotyl, 2-pentenyl, 3-hexenyl, 2-cyclopropyl, etc. In some embodiments, optionally substituted alkyl and alkenyl groups include $C_{1-6}$ alkyls, $C_{2-6}$ alkenyls or $C_{2-6}$ alkynyls.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like.

Therapeutic Indications

The invention provides methods of treating conditions that are modulated, directly or indirectly, by an O-GlcNAcase enzyme or by O-GlcNAc-modified protein levels, for example, a condition that is benefited by inhibition of an O-GlcNAcase enzyme or by an elevation of O-GlcNAc-modified protein levels. Such conditions may include, without limitation, glaucoma, schizophrenia, tauopathies, such as Alzheimer's disease, neurodegenerative diseases, cardiovascular diseases, diseases associated with inflammation, diseases associated with immunosuppression and cancers. One or more of the compounds of the invention may also be useful in the treatment of diseases or disorders related to deficiency or over-expression of O-GlcNAcase or accumulation or depletion of O-GlcNAc, or any disease or disorder responsive to glycosidase inhibition therapy. Such diseases and disorders may include, but are not limited to, glaucoma, schizophrenia, Huntington's disease, Parkinson's disease, Amyotrophic lateral sclerosis, mild cognitive impairment (MCI), neuropathy, neurodegenerative disorders, such as Alzheimer's disease (AD), or cancer. Such diseases and disorders may also include diseases or disorders related to the accumulation or deficiency in the enzyme OGT. Also included is a method of protecting or treating target cells expressing proteins that are modified by O-GlcNAc residues, the dysregulation of which modification may result in disease or pathology. The term "treating" as used herein includes treatment, prevention, and amelioration.

In alternative embodiments, the invention provides methods of enhancing or elevating levels of protein O-GlcNAc modification in animal subjects, such as, veterinary and human subjects. This elevation of O-GlcNAc levels may be useful for the prevention or treatment of Alzheimer's disease; prevention or treatment of other neurodegenerative diseases (e.g. Parkinson's disease, Huntington's disease); providing neuroprotective effects; preventing damage to cardiac tissue; and treating diseases associated with inflammation or immunosuppression.

In alternative embodiments, the invention provides methods of selectively inhibiting an O-GlcNAcase enzyme in animal subjects, such as veterinary and human subjects.

In alternative embodiments, the invention provides methods of inhibiting phosphorylation of tau polypeptides, or inhibiting formation of NFTs, in animal subjects, such as, veterinary and human subjects. Accordingly, a compound of the invention may be used to study and treat AD and other tauopathies.

In general, the methods of the invention may be effected by administering a compound according to the invention to a subject in need thereof, or by contacting a cell or a sample with a compound according to the invention, for example, a pharmaceutical composition comprising a therapeutically effective amount of the compound according to Formula (I). More particularly, they may be useful in the treatment of a disorder in which the regulation of O-GlcNAc protein modification is implicated, or any condition as described herein. Disease states of interest may include Alzheimer's disease (AD) and related neurodegenerative tauopathies, in which abnormal hyperphosphorylation of the microtubule-associated protein tau is involved in disease pathogenesis. In some embodiments, a compound may be used to block hyperphosphorylation of tau by maintaining elevated levels of O-GlcNAc on tau, thereby providing therapeutic benefit.

The effectiveness of a compound in treating pathology associated with the accumulation of toxic tau species (for example, Alzheimer's disease and other tauopathies) may be confirmed by testing the ability of a compound to block the formation of toxic tau species in established cellular[121-123] and/or transgenic animal models of disease.[33,34]

Tauopathies that may be treated with a compound of the invention may include, without limitation: Alzheimer's disease, Amyotrophic lateral sclerosis with cognitive impairment (ALSci), Argyrophilic grain dementia, Bluit disease, Corticobasal degeneration (CBD), Dementia pugilistica, Diffuse neurofibrillary tangles with calcification, Down's syndrome, Familial British dementia, Familial Danish dementia, Frontotemporal dementia with parkinsonism linked to chromosome 17 (FTDP-17), Gerstmann-Straussler-Scheinker disease, Guadeloupean parkinsonism, Hallevorden-Spatz disease (neurodegeneration with brain iron accumulation type 1), Multiple system atrophy, Myotonic dystrophy, Niemann-Pick disease (type C), Pallido-ponto-nigral degeneration, Parkinsonism-dementia complex of Guam, Pick's disease (PiD), Post-encephalitic parkinsonism (PEP), Prion diseases (including Creutzfeldt-Jakob Disease (CJD), Variant Creutzfeldt-Jakob Disease (vCJD), Fatal Familial Insomnia, and Kuru), Progressive supercortical gliosis, Progressive supranuclear palsy (PSP), Richardson's syndrome, Subacute sclerosing panencephalitis, Tangle-only dementia, and Glaucoma.

One or more of the compounds of this invention may also be useful in the treatment of conditions associate with tissue damage or stress, stimulating cells, or promoting differentiation of cells. Accordingly, in some embodiments, a compound of this invention may be used to provide therapeutic benefit in a variety of conditions or medical procedures involving stress in cardiac tissue; such conditions may include, without limitation: ischemia; hemorrhage; hypovolemic shock; myocardial infarction; an interventional cardiology procedure; cardiac bypass surgery; fibrinolytic therapy; angioplasty; and stent placement.

The effectiveness of a compound in treating pathology associated with cellular stress (including ischemia, hemorrhage, hypovolemic shock, myocardial infarction, and other cardiovascular disorders) may be confirmed by testing the ability of a compound to prevent cellular damage in established cellular stress assays,[108,119,120] and to prevent tissue damage and promote functional recovery in animal models of ischemia-reperfusion,[71,117] and trauma-hemorrhage.[73,115,118]

Compounds that selectively inhibit O-GlcNAcase activity may be used for the treatment of diseases that are associated with inflammation; such conditions may include, without limitation: inflammatory or allergic diseases such as asthma, allergic rhinitis, hypersensitivity lung diseases, hypersensitivity pneumonitis, eosinophilic pneumonias, delayed-type hypersensitivity, atherosclerosis, interstitial lung disease (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies, insect sting allergies; autoimmune diseases, such as rheumatoid arthritis, psoriatic arthritis, multiple sclerosis, Guillain-Barré syndrome, systemic lupus erythematosus, myastenia gravis, glomerulonephritis, autoimmune thyroiditis, graft rejection, including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as dermatitis, eczema, atopic dermatitis, allergic contact dermatitis, urticaria; vasculitis (e.g., necrotizing, cutaneous, and hypersensitivity vasculitis); eosinphilic myotis, eosiniphilic fasciitis; and cancers.

In addition, compounds that affect levels of protein O-GlcNAc modification may be used for the treatment of diseases associated with immunosuppression, such as, for example, in individuals undergoing chemotherapy, radiation therapy, enhanced wound healing and burn treatment, therapy for autoimmune disease or other drug therapy (e.g., corticosteroid therapy) or combination of conventional drugs used in the treatment of autoimmune diseases and graft/transplantation rejection, which causes immunosuppression; or immunosuppression due to congenital deficiency in receptor function or other causes.

One or more of the compounds of the invention may be useful for treatment of neurodegenerative diseases; such conditions may include, without limitation, Parkinson's disease and Huntington's disease. Other conditions that may be treated are those triggered, affected, or in any other way correlated with levels of O-GlcNAc post-translational protein modification. It is expected that one or more of the compounds of this invention may be useful for the treatment of such conditions and in particular, but not limited to, the following for which a association with O-GlcNAc levels on proteins has been established: graft rejection, in particular but not limited to solid organ transplants, such as heart, lung, liver, kidney, and pancreas transplants (e.g. kidney and lung allografts); cancer, in particular but not limited to cancer of the breast, lung, prostate, pancreas, colon, rectum, bladder, kidney, ovary; as well as non-Hodgkin's lymphoma and melanoma; epilepsy, pain, fibromyalgia, or stroke, e.g., for neuroprotection following a stroke.

Pharmaceutical & Veterinary Compositions, Dosages, and Administration

Pharmaceutical compositions including compounds according to the invention, or for use according to the invention, are contemplated as being within the scope of the invention. In some embodiments, pharmaceutical compositions including an effective amount of a compound of Formulas (I), (II) or (III), pharmaceutically acceptable salts, prodrugs, and enantiomeric forms thereof in combination with a pharmaceutically acceptable carrier (as defined below) are provided.

The compounds of Formulas (I), (II) and (III) and their pharmaceutically acceptable salts, enantiomers, solvates, and derivatives may be useful because they may have pharmacological activity in animals, including humans. In some embodiments, one or more of the compounds according to the invention may be stable in plasma, when administered to a subject.

In some embodiments, a compound according to the invention, or for use according to the invention, may be provided in combination with any other active agents or pharmaceutical compositions where such combined therapy may be useful to modulate O-GlcNAcase activity, for example, to treat neurodegenerative, inflammatory, cardiovascular, or immunoregulatory diseases, or any condition described herein. In some embodiments, a compound according to the invention, or for use according to the invention, may be provided in combination with one or more agents useful in the prevention or treatment of Alzheimer's disease. Examples of such agents may include, without limitation, acetylcholine esterase inhibitors (AChEIs) such as Aricept@ (Donepezil), Exelon® (Rivastigmine), Razadyne® (Razadyne ER®, Reminyl®, Nivalin®, Galantamine), Cognex® (Tacrine), Dimebon, Huperzine A, Phenserine, Debio-9902 SR (ZT-1 SR), Zanapezil (TAK0147), ganstigmine, NP7557, etc.;

NMDA receptor antagonists such as Namenda@ (Axura@, Akatinol®, Ebixa®, Memantine), Dimebon, SGS-742, Neramexane, Debio-9902 SR (ZT-1 SR), etc.;

gamma-secretase inhibitors and/or modulators such as Flurizan™ (Tarenflurbil, MPC-7869, R-flurbiprofen), LY450139, MK 0752, E2101, BMS-289948, BMS-299897, BMS-433796, LY-411575, GSI-136, etc.;

beta-secretase inhibitors such as ATG-ZI, CTS-21166, MK-8931, etc.;

alpha-secretase activators, such as NGX267, etc;

amyloid-β aggregation and/or fibrillization inhibitors such as Alzhemed™ (3APS, Tramiprosate, 3-amino-1-propanesulfonic acid), AL-108, AL-208, AZD-103, PBT2, Cereact, ONO-2506PO, PPI-558, etc.;

tau aggregation inhibitors such as methylene blue, etc.;

microtubule stabilizers such as AL-108, AL-208, paclitaxel, etc.;

RAGE inhibitors, such as TTP488, etc.;

5-HT1a receptor antagonists, such as Xaliproden, Lecozotan, etc.;

5-HT4 receptor antagonists, such as PRX-03410, etc.;

kinase inhibitors such as SRN-003-556, amfurindamide, LiCI, AZDIO80, NPO31112, SAR-502250, etc.

humanized monoclonal anti-Aβ antibodies such as Bapineuzumab (AAB-001), LY2062430, RN1219, ACU-5A5, etc.;

amyloid vaccines such as AN-1792, ACC-001, etc.;

neuroprotective agents such as Cerebrolysin, AL-108, AL-208, Huperzine A, etc.;

L-type calcium channel antagonists such as MEM-1003, etc.;

nicotinic receptor antagonists, such as AZD3480, GTS-21, etc.;

nicotinic receptor agonists, such as MEM 3454, Nefiracetam, etc.;

peroxisome proliferator-activated receptor (PPAR) gamma agonists such as Avandia® (Rosglitazone), etc.;

phosphodiesterase IV (PDE4) inhibitors, such as MK-0952, etc.;

hormone replacement therapy such as estrogen (Premarin), etc.;

monoamine oxidase (MAO) inhibitors such as NS2330, Rasagiline (Azilect®), TVP-1012, etc.;

AMPA receptor modulators such as Ampalex (CX 516), etc.;

nerve growth factors or NGF potentiators, such as CERE-110 (AAV-NGF), T-588, T-817MA, etc.;

agents that prevent the release of luteinizing hormone (LH) by the pituitary gland, such as leuoprolide (VP-4896), etc.;

GABA receptor modulators such as AC-3933, NGD 97-1, CP-457920, etc.;

benzodiazepine receptor inverse agonists such as SB-737552 (S-8510), AC-3933, etc.;

noradrenaline-releasing agents such as T-588, T-817MA, etc.

It is to be understood that combination of compounds according to the invention, or for use according to the invention, with Alzheimer's agents is not limited to the examples described herein, but may include combination with any agent useful for the treatment of Alzheimer's disease. Combination of compounds according to the invention, or for use according to the invention, and other Alzheimer's agents may be administered separately or in conjunction. The administration of one agent may be prior to, concurrent to, or subsequent to the administration of other agent(s).

In alternative embodiments, a compound may be supplied as a "prodrug" or protected forms, which release the compound after administration to a subject. For example, a compound may carry a protective group which is split off by hydrolysis in body fluids, e.g., in the bloodstream, thus releasing the active compound or is oxidized or reduced in body fluids to release the compound. Accordingly, a "prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but may be converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a subject.

The term "prodrug" is also meant to include any covalently bonded carriers which release the active compound of the invention in vivo when such prodrug is administered to a subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention where a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol and acetamide, formamide, and benzamide derivatives of amine functional groups in one or more of the compounds of the invention and the like.

A discussion of prodrugs may be found in "Smith and Williams' Introduction to the Principles of Drug Design," H. J. Smith, Wright, Second Edition, London (1988); Bundgard, H., *Design of Prodrugs* (1985), pp. 7-9, 21-24 (Elsevier, Amsterdam); The Practice of Medicinal Chemistry, Camille G. Wermuth et al., Ch 31, (Academic Press, 1996); A Textbook of Drug Design and Development, P. Krogsgaard-Larson and H. Bundgaard, eds. Ch 5, pgs 113 191 (Harwood Academic Publishers, 1991); Higuchi, T., et al., "Pro-drugs as Novel Delivery Systems," A.C.S. Symposium Series, Vol. 14; or in Bioreversible Carriers in Drug Design, ed. Edward B. Roche, American Pharmaceutical Association and Pergamon Press, 1987.

Suitable prodrug forms of one or more of the compounds of the invention may include embodiments in which one or more OH groups as set forth in Formula (I) may be protected as OC(O)R, where R may be optionally substituted alkyl, alkenyl, or alkynyl. In these cases the ester groups may be hydrolyzed in vivo (e.g. in bodily fluids), liberating the OH groups and releasing the active compounds. Preferred prodrug embodiments of the invention may include compounds of Formula (I) where one or more OH groups may be protected with acetate, for example as $OC(O)CH_3$.

Compounds according to the invention, or for use according to the invention, may be provided alone or in combination with other compounds in the presence of a liposome, an adjuvant, or any pharmaceutically acceptable carrier, diluent or excipient, in a form suitable for administration to a subject such as a mammal, for example, humans, cattle, sheep, etc. If desired, treatment with a compound according to the invention may be combined with more traditional and existing therapies for the therapeutic indications described herein. Compounds according to the invention may be provided chronically or intermittently. "Chronic" administration refers to administration of the compound(s) in a continuous mode as opposed to an acute mode, so as to maintain the initial therapeutic effect (activity) for an extended period of time. "Intermittent" administration is treatment that is not consecutively done without interruption, but rather is cyclic in nature. The terms "administration," "administrable," or "administering" as used herein should be understood to mean providing a compound of the invention to the subject in need of treatment.

"Pharmaceutically acceptable carrier, diluent or excipient" may include, without limitation, any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier that has been approved, for example, by the United States Food and Drug Administration or other governmental agency as being acceptable for use in humans or domestic animals.

A compound of the present invention may be administered in the form of a pharmaceutically acceptable salt. In such cases, pharmaceutical compositions in accordance with this invention may comprise a salt of such a compound, preferably a physiologically acceptable salt, which are known in the art. In some embodiments, the term "pharmaceutically acceptable salt" as used herein means an active ingredient comprising compounds of Formula I used in the form of a salt thereof, particularly where the salt form confers on the active ingredient improved pharmacokinetic properties as compared to the free form of the active ingredient or other previously disclosed salt form.

A "pharmaceutically acceptable salt" may include both acid and base addition salts. A "pharmaceutically acceptable acid addition salt" refers to those salts which retain the biological effectiveness and properties of the free bases, which are not biologically or otherwise undesirable, and which may be formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

A "pharmaceutically acceptable base addition salt" refers to those salts which may retain the biological effectiveness and properties of the free acids, which may not be biologically or otherwise undesirable. These salts may be prepared from addition of an inorganic base or an organic base to the free acid. Salts derived from inorganic bases may include, but are not limited to, the sodium, potassium, lithium, ammonium, calcium, magnesium, iron, zinc, copper, manganese, aluminum salts and the like. Preferred inorganic salts may be the ammonium, sodium, potassium, calcium, and magnesium salts. Salts derived from organic bases may include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine,methylglucamine, theobromine, purines, piperazine, piperidine, N-ethylpiperidine, polyamine resins and the like. Particularly preferred organic bases may be isopropylamine, diethylamine, ethanolamine, trimethylamine, dicyclohexylamine, choline and caffeine.

Thus, the term "pharmaceutically acceptable salt" encompasses all acceptable salts including but not limited to acetate, lactobionate, benzenesulfonate, laurate, benzoate, malate, bicarbonate, maleate, bisulfate, mandelate, bitartarate, mesylate, borate, methylbromide, bromide, methylnitrite, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutame, stearate, glycollylarsanilate, sulfate, hexylresorcinate, subacetate, hydradamine, succinate, hydrobromide, tannate, hydrochloride, tartrate, hydroxynaphthoate, teoclate, iodide, tosylate, isothionate, triethiodide, lactate, panoate, valerate, and the like.

Pharmaceutically acceptable salts of a compound of the present invention may be used as a dosage for modifying solubility or hydrolysis characteristics, or may be used in sustained release or prodrug formulations. Also, pharmaceutically acceptable salts of a compound of this invention may include those formed from cations such as sodium, potassium, aluminum, calcium, lithium, magnesium, zinc, and from bases such as ammonia, ethylenediamine, N-methylglutamine, lysine, arginine, ornithine, choline, N,N'-dibenzylethylene-diamine, chloroprocaine, diethanolamine, procaine, N-benzylphenethyl-amine, diethylamine, piperazine, tris(hydroxymethyl)aminomethane, and tetramethylammonium hydroxide.

Pharmaceutical formulations may typically include one or more carriers acceptable for the mode of administration of the preparation, be it by injection, inhalation, topical administration, lavage, or other modes suitable for the selected treatment. Suitable carriers may be those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non-water soluble compounds such as those used for vitamin K. For enteral administration, the compound may be administered in a tablet, capsule or dissolved in liquid form. The table or capsule may be enteric coated, or in a formulation for sustained release. Many suitable formulations are known, including, polymeric or protein microparticles encapsulating a compound to be released, ointments, gels, hydrogels, or solutions which can be used topically or locally to administer a compound. A sustained release patch or implant may be employed to provide release over a prolonged period of time. Many techniques known to skilled practitioners are described in *Remington: the Science & Practice of Pharmacy* by Alfonso Gennaro, 20$^{th}$ ed., Williams & Wilkins, (2000). Formulations for parenteral administration may, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of a compound. Other potentially useful parenteral delivery systems for modulatory compounds may include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

A compound or a pharmaceutical composition according to the present invention may be administered by oral or non-oral, e.g., intramuscular, intraperitoneal, intravenous, intracisternal injection or infusion, subcutaneous injection, transdermal or transmucosal routes. In some embodiments, a compound or pharmaceutical composition in accordance with this invention or for use in this invention may be administered by means of a medical device or appliance such as an implant, graft, prosthesis, stent, etc. Implants may be devised which are intended to contain and release such compounds or compositions. An example would be an implant made of a polymeric material adapted to release the compound over a period of time. A compound may be administered alone or as a mixture with a pharmaceutically acceptable carrier e.g., as solid formulations such as tablets, capsules, granules, powders, etc.; liquid formulations such as syrups, injections, etc.; injections, drops, suppositories, pessaryies. In some embodiments, compounds or pharmaceutical compositions in accordance with this invention or for use in this invention may be administered by inhalation spray, nasal, vaginal, rectal, sublingual, or topical routes and may be formulated, alone or together, in suitable dosage unit formulations containing conventional non-toxic pharmaceutically acceptable carriers, adjuvants and vehicles appropriate for each route of administration.

A compound of the invention may be used to treat animals, including mice, rats, horses, cattle, sheep, dogs, cats, and monkeys. However, a compound of the invention may also be used in other organisms, such as avian species (e.g., chickens). One or more of the compounds of the invention may also be effective for use in humans. The term "subject" or alternatively referred to herein as "patient" is intended to be referred to an animal, preferably a mammal, most preferably a human, who has been the object of treatment, observation or experiment. However, one or more of the compounds, methods and pharmaceutical compositions of the present invention may be used in the treatment of animals. Accordingly, as used herein, a "subject" may be a human, non-human primate, rat, mouse, cow, horse, pig, sheep, goat, dog, cat, etc. The subject may be suspected of having or at risk for having a condition that may require modulation of O-GlcNAcase activity.

An "effective amount" of a compound according to the invention may include a therapeutically effective amount or a prophylactically effective amount. A "therapeutically effective amount" refers to an amount effective, at dosages and for periods of time necessary, to achieve the desired therapeutic result, such as inhibition of an O-GlcNAcase, elevation of O-GlcNAc levels, inhibition of tau phosphorylation, or any condition described herein. A therapeutically effective amount of a compound may vary according to factors such as the disease state, age, sex, and weight of the individual, and the ability of the compound to elicit a desired response in the individual. Dosage regimens may be adjusted to provide the optimum therapeutic response. A therapeutically effective amount may also be one in which any toxic or detrimental effects of the compound are outweighed by the therapeutically beneficial effects. A "prophylactically effective amount" may refer to an amount effective, at dosages and for periods of time necessary, to achieve the desired prophylactic result, such as inhibition of an O-GlcNAcase, elevation of O-GlcNAc levels, inhibition of tau phosphorylation, or any condition described herein. Typically, a prophylactic dose may be used in subjects prior to or at an earlier stage of disease, so that a prophylactically effective amount may be less than a therapeutically effective amount. A suitable range for therapeutically or prophylactically effective amounts of a compound may be any integer from 0.1 nM-0.1 M, 0.1 nM-0.05 M, 0.05 nM-15 µM or 0.01 nM-10 µM.

In alternative embodiments, in the treatment or prevention of conditions which may require modulation of O-GlcNAcase activity, an appropriate dosage level may generally be about 0.01 to 500 mg per kg subject body weight per day, and may be administered in singe or multiple doses. In some embodiments, the dosage level may be about 0.1 to about 250 mg/kg per day. It will be understood that the specific dose level and frequency of dosage for any particular patient may be varied and may depend upon a variety of factors including the activity of the specific compound used, the metabolic stability and length of action of that compound, the age, body weight, general health, sex, diet, mode and time of administration, rate of excretion, drug combination, the severity of the particular condition, and the patient undergoing therapy.

It is to be noted that dosage values may vary with the severity of the condition to be alleviated. For any particular subject, specific dosage regimens may be adjusted over time according to the individual need and the professional judgement of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the subject. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage. In general, compounds of the invention should be used without causing substantial toxicity, and as described herein, one or more of the compounds may exhibit a suitable safety profile for therapeutic use. Toxicity of a compound of the invention may be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances however, such as in severe disease conditions, it may be necessary to administer substantial excesses of the compositions.

In the compounds of generic Formulas (I), (II) and (Ill) the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula (I). For example, different isotopic forms of hydrogen (H) include protium ($^1$H), deuterium ($^2$H) and tritium ($^3$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formulas (I), (II) or (III) may be prepared without undue experimentation by conventional techniques well known to those skilled in the art or by processes analogous to those described in the Schemes and Examples herein using appropriate isotopically-enriched reagents and/or intermediates.

Other Uses and Assays

A compound of Formulas (I), (II) or (III) may be used in screening assays for compounds which modulate the activity of glycosidase enzymes, preferably the O-GlcNAcase enzyme. The ability of a test compound to inhibit O-GlcNAcase-dependent cleavage of O-GlcNAc from a model substrate may be measured using any assays, as described herein or known to one of ordinary skill in the art. For example, a fluoresence or UV-based assay known in the art may be used. A "test compound" may be any naturally-occurring or artificially-derived chemical compound. Test compounds may include, without limitation, peptides, polypeptides, synthesised organic molecules, naturally occurring organic molecules, and nucleic acid molecules. A test compound may "compete" with a known compound such as a compound of Formulas (I), (II) or (III) by, for example, interfering with inhibition of O-GlcNAcase-dependent cleavage of O-GlcNAc or by interfering with any biological response induced by a compound of Formula (I).

Generally, a test compound may exhibit any value between 10% and 200%, or over 500%, modulation when compared to a compound of Formula (I) or other reference compound. For example, a test compound may exhibit at least any positive or negative integer from 10% to 200% modulation, or at least any positive or negative integer from 30% to 150% modulation, or at least any positive or negative integer from 60% to 100% modulation, or any positive or negative integer over 100% modulation. A compound that is a negative modulator may in general decrease modulation relative to a known compound, while a compound that is a positive modulator may in general increase modulation relative to a known compound.

In general, test compounds may be identified from large libraries of both natural products or synthetic (or semi-synthetic) extracts or chemical libraries according to methods known in the art. Those skilled in the field of drug discovery and development will understand that the precise source of test extracts or compounds is not critical to the method(s) of the invention. Accordingly, virtually any number of chemical extracts or compounds may be screened using the exemplary methods described herein. Examples of such extracts or compounds may include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, that may include, without limitation, saccharide-, lipid-, peptide-, and nucleic acid-based compounds. Synthetic compound libraries are commercially available. Alternatively, libraries of natural compounds in the form of bacterial, fungal, plant, and animal extracts are commercially available from a number of sources, including Biotics (Sussex, UK), Xenova (Slough, UK), Harbor Branch Oceanographic Institute (Ft. Pierce, Fla., USA), and PharmaMar, MA, USA. In addition, natural and synthetically produced libraries may be produced, if desired, according to methods known in the art, e.g., by standard extraction and fractionation methods. Furthermore, if desired, any library or compound may be readily modified using standard chemical, physical, or biochemical methods.

When a crude extract is found to modulate inhibition of O-GlcNAcase-dependent cleavage of O-GlcNAc, or any biological response induced by a compound of Formula (I), further fractionation of the positive lead extract may be necessary to isolate chemical constituents responsible for the observed effect. Thus, the goal of the extraction, fractionation, and purification process is the careful characterization and identification of a chemical entity within the crude extract having O-GlcNAcase-inhibitory activities. The same assays described herein for the detection of activities in mixtures of compounds may be used to purify the active component and to test derivatives thereof. Methods of fractionation and purification of such heterogeneous extracts are known in the art. If desired, compounds shown to be useful agents for treatment may be chemically modified according to methods known in the art. Compounds identified as being of therapeutic, prophylactic, diagnostic, or other value may be subsequently analyzed using a suitable animal model, as described herein on known in the art.

In some embodiments, one or more of the compounds may be useful in the development of animal models for studying diseases or disorders that may be related to deficiencies in O-GlcNAcase, over-expression of O-GlcNAcase, accumulation of O-GlcNAc, depletion of O-GlcNAc, and for studying treatment of diseases and disorders that may be related to deficiency or over-expression of O-GlcNAcase, or accumulation or depletion of O-GlcNAc. Such diseases and disorders may include neurodegenerative diseases, including Alzheimer's disease, and cancer.

Various alternative embodiments and examples of the invention are described herein. These embodiments and examples are illustrative and should not be construed as limiting the scope of the invention.

EXAMPLES

The following examples are intended to illustrate embodiments of the invention and are not intended to be construed in a limiting manner.

Abbreviations

AIBN (2,2'-Azobisisobutyronitrile)
BCl₃ (Boron Trichloride)
Bu₃SnH (Tributyltin hydride)
CDCl₃ (Deuterochloroform)
DAST (Diethylamino)sulfur trifluoride)
DCM (Dichloromethane)
DMP (Dess-Martin Periodinane)
EDC (1-Ethyl-3(3-Dimethiaminopropyl carbodiimide HCl)
NBS (N-Bromosuccinimide)
Pd(PPh₃)₄(Tretrakis(Trhphenylphosphine) palladium (0))
PMB (Para-methoxybenzyl)
TBAB (Tetrabutyl ammonium bromide)
TBAF (Tetra-n-butyl ammonium fluoride)
TEMPO ((2,2,6,6-Tetramiethylpiperidin-1-yl)oxyl)
THF (tetrahydrofuran)
TMS (Trimethylsilyl)

Examples 1 and 2

(3aR,5R,6S,7R,7aR)-2-(dimethylamino)-5-((R)-1,1,1-trifluoro-4-(4-methoxyphenyl)butan-2-yl)-5,6,7,7a-tetrahydro-3aH-pyrano[3,2-d]thiazole-6,7-diol & (3aR,5R,6S,7R,7aR)-2-(dimethylamino)-5-((S)-1,1,1-trifluoro-4-(4-methoxyphenyl)butan-2-yl)-5,6,7,7a-tetrahydro-3aH-pyrano[3,2-d]thiazole-6,7-diol)

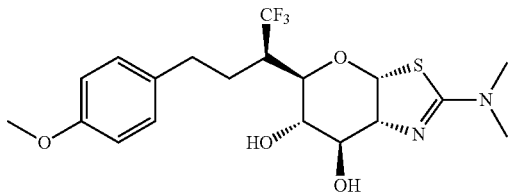

Example 1

&

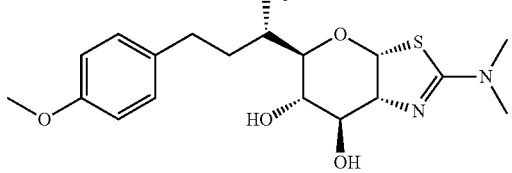

Example 2

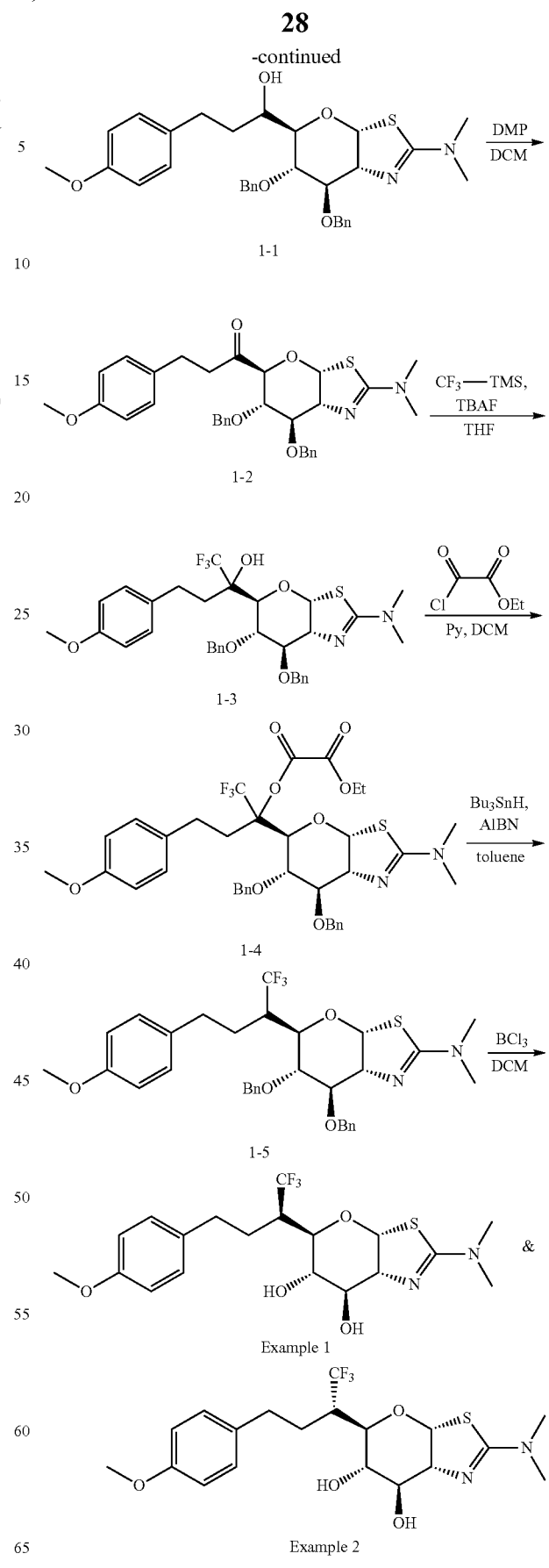

Step 1

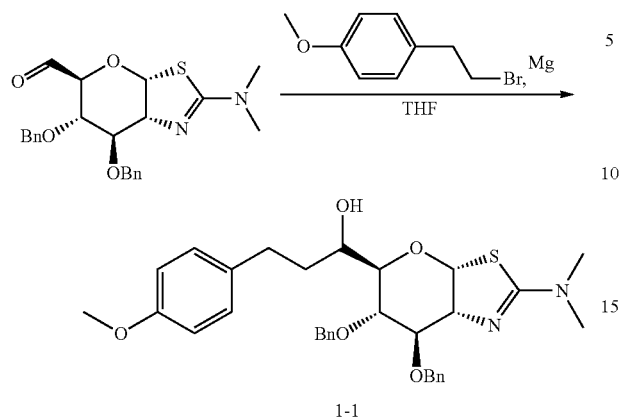

1-1

(S)-1-((3aR,5R,6S,7R,7aR)-6,7-bis(benzyloxy)-2-(dimethylamino)-5,6,7,7a-tetrahydro-3aH-pyrano[3,2-d]thiazol-5-yl)-3-(4-methoxyphenyl)propan-1-ol (1-1)

A solution of (4-methoxyphenethyl)magnesium bromide in anhydrous THF (20 mL) was prepared from magnesium (144 mg, 6 mmol) and 1-(2-bromoethyl)-4-methoxybenzene (1.28 g, 6 mmol) using standard conditions. After cooling the solution to −10° C., a solution of (3aR,5S,6S,7R,7aR)-6,7-bis(benzyloxy)-2-(dimethylamino)-5,6,7,7a-tetrahydro-3aH-pyrano[3,2-d]thiazole-5-carbaldehyde (WO2012/061972 A1), (850 mg, 2 mmol) in anhydrous THF (10 mL) was added dropwise over a period of 20 min. The reaction mixture was then allowed to warm to 0° C. and was stirred for additional 2 hours. Then the reaction was quenched by saturated aqueous ammonium chloride (10 mL), extracted with dichloromethane (3×20 mL). The combined organic layer was washed with brine (20 mL), dried over anhydrous magnesium sulfate and concentrated under reduced pressure to give a residue, which was purified by a silica gel column, eluted with 5%~40% ethyl acetate in petroleum ether to afford the title compound 736 mg, 65%, two epimers' ratio is 6:1 by $^1$H NMR) as a yellow syrup; (ES, m/z)[M+H]$^+$ 563.1; $^1$H NMR (300 MHz, CDCl$_3$) δ 7.42-7.27 (m, 10H), 7.12-7.10 (m, 2H), 6.84-6.81 (m, 2H), 6.34-6.32 (m, 1H), 4.78-4.59 (m, 4H), 4.49-4.42 (m, 1H), 4.27-4.25 (m, 1H), 3.87-3.85 (m, 1H), 3.84 (s, 3H), 3.77-3.68 (m, 1H), 3.48-3.45 (m, 1H), 3.01 (s, 6H), 2.79-2.56 (m, 2H), 1.84-1.61 (m, 2H).

Step 2

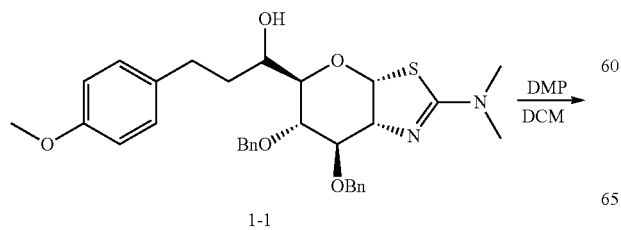

1-2

1-((3aR,5 S,6S,7R,7aR)-6,7-bis(benzyloxy)-2-(dimethylamino)-5,6,7,7a-tetrahydro-3aH-pyrano[3,2-d]thiazol-5-yl)-3-(4-methoxyphenyl)propan-1-one (1-2)

To a solution of 1-1 (730 mg, 1.3 mmol) in dichloromethane (20 mL) was added DMP (1.1 g, 2.6 mmol) at 0° C. After stirring for 3 hours at room temperature, the reaction was quenched by saturated aqueous sodium thiosulphate (15 mL) and sodium bicarbonate (15 mL), extracted with dichloromethane (3×50 mL). The combined organic layer was washed with brine (2×30 mL), dried over anhydrous sodium sulfate and concentrated under reduced pressure to give a residue, which was purified by a silica gel column, eluted with 5%-30% ethyl acetate in petroleum ether to afford the title compound (640 mg, 88%) as a yellow syrup; (ES, m/z)[M+H]$^+$561.2; $^1$H NMR (300 MHz, CDCl$_3$) δ 7.51-7.21 (m, 10H), 7.07 (d, J=8.1 Hz, 2H), 6.79 (d, J=8.1 Hz, 2H), 6.27 (d, J=6.3 Hz, 1H), 4.72-4.52 (m, 4H), 4.44-4.40 (m, 1H), 4.30-4.22 (m, 1H), 3.99-3.87 (m, 2H), 3.76 (s, 3H), 2.96 (s, 6H), 2.87-2.65 (m, 4H).

Step 3

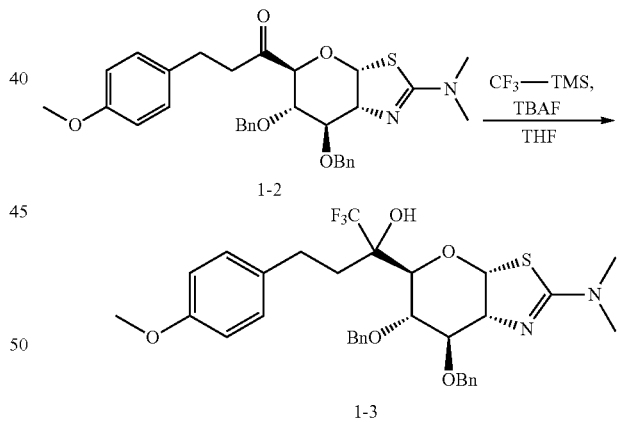

(R)-2-((3aR,5 S,6S,7R,7aR)-6,7-bis(benzyloxy)-2-(dimethylamino)-5,6,7,7a-tetrahydro-3aH-pyrano[3,2-d]thiazol-5-yl)-1,1,1-trifluoro-4-(4-methoxyphenyl)butan-2-ol (1-3)

A mixture of TBAF (105 mg, 0.4 mmol) and 4 A° molecule sieves in anhydrous THF (10 mL) was stirred for 30 min at 0° C. followed by the addition of a solution of 1-2 (500 mg, 0.9 mmol) and CF$_3$-TMS (508 mg, 3.6 mmol) in anhydrous THF (10 mL). After stirring for additional 12 hours at 25° C., additional TBAF (340 mg, 1.3 mmol) was added, and the mixture was stirred for 1 hour. The reaction was quenched by water (15 mL), extracted with ethyl acetate (3×30 mL), the combined organic layer was washed with brine (2×20 mL), dried over anhydrous sodium sulfate and concentrated under reduced pressure to give a residue, which was purified by a silica gel column, eluted with 3%~25% ethyl acetate in petroleum ether to afford the title compound (365 mg, 65%, two epimers' ratio is 1:1 by 1H NMR) as a yellow syrup; (ES, m/z)[M+H]$^+$ 631.1; $^1$H NMR (300 MHz, CDCl3) δ 7.51-7.21 (m, 10H), 7.11 (d, J=8.4 Hz, 2H), 6.89 (d, J=8.1 Hz, 2H), 6.41-6.30 (m, 1H), 4.84-4.67 (m, 4H), 4.41-4.27 (m, 2H), 4.11-3.86 (m, 2H), 3.76 (s, 3H), 2.99 (s, 6H), 2.80-2.73 (m, 2H), 2.07-1.89 (m, 2H).

Step 2

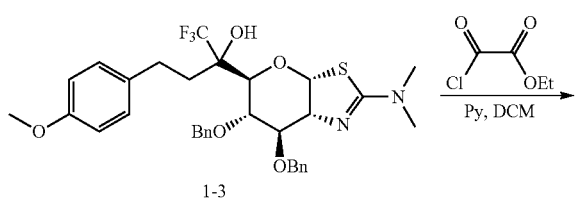

(R)-2-((3aR,5S,6S,7R,7aR)-6,7-bis(benzyloxy)-2-(dimethylamino)-5,6,7,7a-tetrahydro-3aH-pyrano[3,2-d]thiazol-5-yl)-1,1,1-trifluoro-4-(4-methoxyphenyl)butan-2-yl ethyl oxalate (1-4)

To a solution of 1-3 (315 mg, 0.5 mmol) in anhydrous dichloromethane (10 mL) was added pyridine (237 mg, 3 mmol) and ethyl 2-chloro-2-oxoacetate (544 mg, 4 mmol) at room temperature under nitrogen atmosphere. After stirring for 6 hours, the reaction was quenched by saturated aqueous sodium bicarbonate (10 mL), extracted with dichloromethane (3×20 mL). The combined organic layer was washed with brine (2×20 mL), dried over anhydrous sodium sulfate and concentrated under reduced pressure to give crude 1-4 as a yellow syrup, which was used in next step without further purification; (ES, m/z): [M+H]$^+$ 731.1.

Step 5

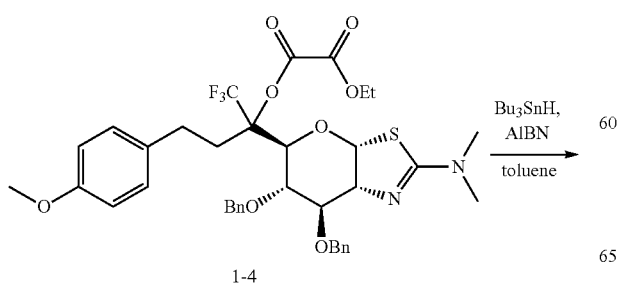

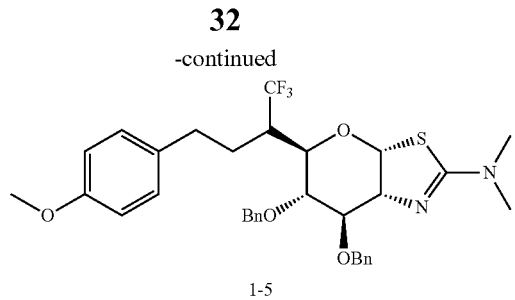

(3aR,5R,6R,7R,7aR)-6,7-bis(benzyloxy)-N,N-dimethyl-5-((S)-1,1,1-trifluoro-4-(4-methoxyphenyl)butan-2-yl)-5,6,7,7a-tetrahydro-3aH-pyrano[3,2-d]thiazol-2-amine (1-5)

To a solution of crude 1-4 in toluene (10 mL) was added Bu$_3$SnH (642 mg, 2.2 mmol) and AIBN (22 mg, 0.13 mmol). After stirred for 2 hours at 90° C., the reaction mixture was concentrated under reduced pressure to give a residue, which was purified by a silica gel column, eluted with 2%-25% ethyl acetate in petroleum ether to afford the title compound (85 mg, 28% of 2 steps, two epimers' ratio is 6:4 by $^1$H NMR) as yellow oil; (ES, m/z)[M+H]$^+$ 615.1; $^1$HNMR (300 MHz, CDCl$_3$) δ 7.55-7.27 (m, 10H), 7.00 (d, J=6.7 Hz, 2H), 6.87 (d, J=5.1 Hz, 2H), 6.33-6.31 (m, 1H), 4.76-4.55 (m, 4H), 4.31-4.27 (m, 1H), 4.01-3.87 (m, 1H), 3.81-3.61 (m, 2H), 3.76 (s, 3H), 3.00 (s, 6H), 2.86-2.63 (m, 3H), 1.85-1.72 (m, 2H).

Step 6

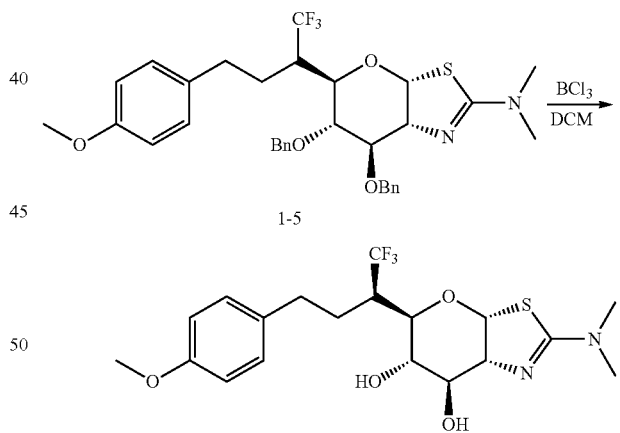

Example 1
&
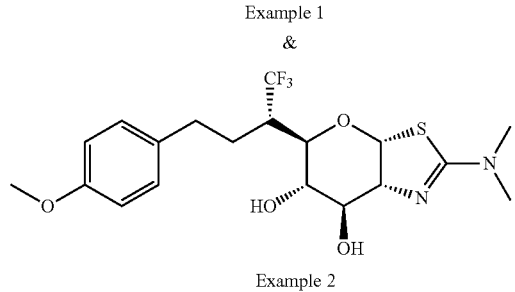
Example 2

(3aR,5R,6S,7R,7aR)-2-(dimethylamino)-5-((R)-1,1,1-trifluoro-4-(4-methoxyphenyl)butan-2-yl)-5,6,7,7a-tetrahydro-3aH-pyrano[3,2-d]thiazole-6,7-diol & (3aR,5R,6S,7R,7aR)-2-(dimethylamino)-5-((S)-1,1,1-trifluoro-4-(4-methoxyphenyl)butan-2-yl)-5,6,7,7a-tetrahydro-3aH-pyrano[3,2-d]thiazole-6,7-diol A solution of 1-5 (61 mg, 0.1 mmol) in DCM (10 mL) was treated with 1 N solution of $BCl_3$ in DCM (1 mL, 1 mmol) for 2 hours at −60° C., then quenched by the addition of methanol (10 mL). Volatiles were distilled out under reduced pressure to give a residue, which was dissolved into methanol (5 mL) and neutralized by Con. $NH_4OH$ (3 ml, 26% aqueous solution). After concentration, the crude product was purified by Prep-HPLC with the following conditions (Agilent 1200 prep HPLC): Column, Sun Fire Prep C18; mobile phase, water with 0.05% $NH_4OH$ and $CH_3CN$ (10% up to 25% in 11 min); Detector, 220 nm, to give (3aR,5R,6S,7R,7aR)-2-(dimethylamino)-5-((R)-1,1,1-trifluoro-4-(4-methoxyphenyl)butan-2-yl)-5,6,7,7a-tetrahydro-3aH-pyrano[3,2-d]thiazole-6,7-diol (10.5 mg, Faster eluting isomer by Prep-HPLC) as a white solid; (ES, m/z) [M+H]$^+$ 435.0; $^1$HNMR (300 MHz, $CD_3OD$) δ 7.13 (d, J=6.3 Hz, 2H), 6.86 (d, J=6.3 Hz, 2H), 6.38 (d, J=4.8 Hz, 1H), 4.12 (t, J=4.5 Hz, 1H), 3.89 (t, J=4.2 Hz, 1H), 3.84-3.75 (m, 2H), 3.77 (s, 3H), 3.03 (s, 6H), 2.75-2.59 (m, 3H), 1.95-1.89 (m, 2H). And & (3aR,5R,6S,7R,7aR)-2-(dimethylamino)-5-((S)-1,1,1-trifluoro-4-(4-methoxyphenyl)butan-2-yl)-5,6,7,7a-tetrahydro-3aH-pyrano[3,2-d]thiazole-6,7-diol (9.7 mg, Slower eluting isomer by Prep-HPLC) as a white solid; (ES, m/z) [M+H]$^+$ 435.0; $^1$HNMR (300 MHz, $CD_3OD$) 7.17 (d, J=6.6 Hz, 2H), 6.84 (d, J=6.3 Hz, 2H), 6.37 (d, J=5.3 Hz, 1H), 4.13 (t, J=4.7 Hz, 1H), 3.88 (t, J=5.1 Hz, 1H), 3.84-3.75 (m, 5H), 3.00 (s, 6H), 2.75-2.59 (m, 3H), 1.95-1.89 (m, 2H).

Examples 3 and 4

(3aR,5R,6S,7R,7aR,E)-2-(dimethylamino)-5-(1,1,1-trifluoro-4-(4-methoxyphenyl)but-2-en-2-yl)-5,6,7,7a-tetrahydro-3aH-pyrano[3,2-d]thiazole-6,7-diol & (3aR,5R,6S,7R,7aR,Z)-2-(dimethylamino)-5-(1,1,1-trifluoro-4-(4-methoxyphenyl)but-2-en-2-yl)-5,6,7,7a-tetrahydro-3aH-pyrano[3,2-d]thiazole-6,7-diol

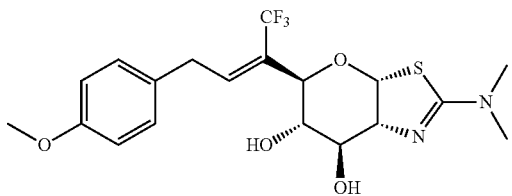

Example 3
&

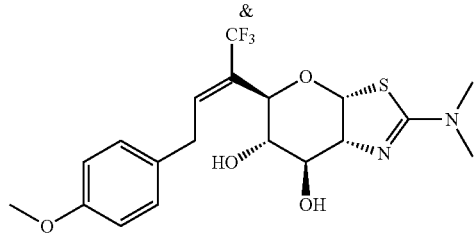

Example 4

Scheme 2

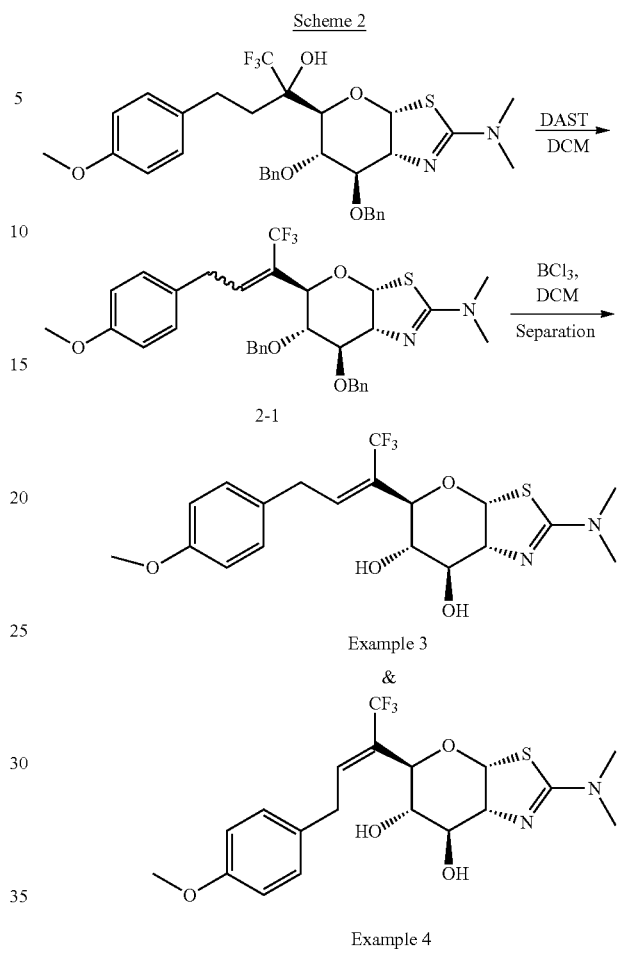

Step 1

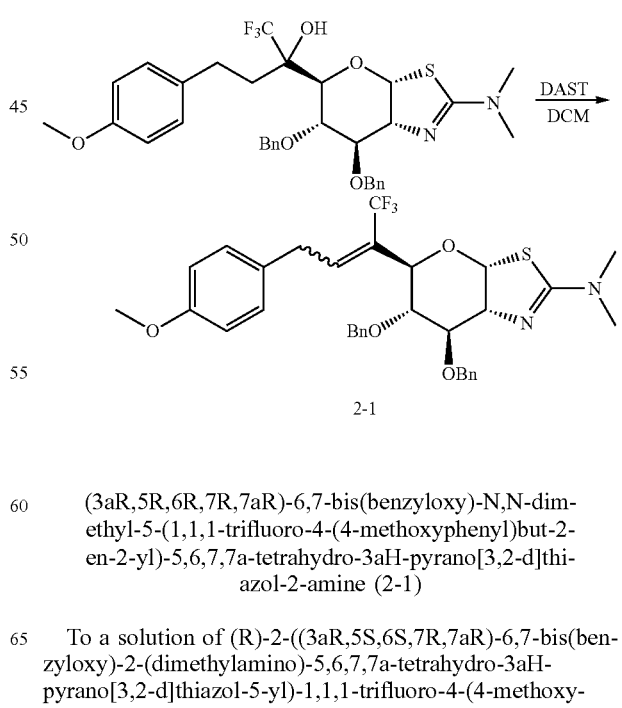

(3aR,5R,6R,7R,7aR)-6,7-bis(benzyloxy)-N,N-dimethyl-5-(1,1,1-trifluoro-4-(4-methoxyphenyl)but-2-en-2-yl)-5,6,7,7a-tetrahydro-3aH-pyrano[3,2-d]thiazol-2-amine (2-1)

To a solution of (R)-2-((3aR,5S,6S,7R,7aR)-6,7-bis(benzyloxy)-2-(dimethylamino)-5,6,7,7a-tetrahydro-3aH-pyrano[3,2-d]thiazol-5-yl)-1,1,1-trifluoro-4-(4-methoxyphenyl)butan-2-ol (470 mg, 0.75 mmol) in dichloromethane (20 mL) was added DAST (1.2 g, 7.4 mmol) at 0° C. After stirring for 4 hours at 15° C., the reaction was quenched by saturated aqueous sodium bicarbonate (20 mL), extracted with dichloromethane (3×50 mL). The combined organic layer was washed with brine (2×30 mL), dried over anhydrous magnesium sulfate and concentrated under reduced pressure to give a residue, which was purified by a silica gel column, eluted with 3%~25% ethyl acetate in petroleum ether to afford the product (225 mg, 49%); (ES, m/z): [M+H]+ 613.1; 1H NMR (300 MHz, CDCl3) δ 7.54-7.26 (m, 10H), 7.23-7.00 (m, 2H), 6.85-6.76 (m, 2H), 6.48-6.15 (m, 2H), 4.87-4.55 (m, 4H), 4.61-4.30 (m, 2H), 4.06-3.96 (m, 1H), 3.80 (s, 3H), 3.74-3.70 (m, 1H), 3.70-3.58 (m, 2H), 3.06-3.01 (m, 6H).

Step 2 white solid; (ES, m/z) [M+H]+ 433.0; 1HNMR (300 MHz, CD3OD) 7.19 (d, J=8.4 Hz, 2H), 6.87 (d, J=8.4 Hz, 2H), 6.51 (t, J=6.9 Hz, 1H), 6.41 (d, J=6.3 Hz, 1H), 4.61 (d, J=9.6 Hz, 1H), 4.17 (t, J=6.3 Hz, 1H), 3.99 (t, J=5.7 Hz, 1H), 3.92-3.87 (m, 1H), 3.78 (s, 3H), 3.70-3.58 (m, 2H), 3.00 (s, 6H).

And (3aR, 5R,6S,7R,7aR,Z)-2-(dimethylamino)-5-(1,1,1-trifluoro-4-(4-methoxyphenyl)but-2-en-2-yl)-5,6,7,7a-tetrahydro-3aH-pyrano[3,2-d]thiazole-6,7-diol (12.5 mg, Slower eluting isomer by Prep-HPLC) as a white solid; (ES, m/z) [M+H]+ 433.0; 1HNMR (300 MHz, CD3OD) 7.14 (d, J=8.7 Hz, 2H), 6.87 (d, J=8.4 Hz, 2H), 6.38 (t, J=7.8 Hz, 1H), 6.32 (d, J=6.6 Hz, 1H), 4.29 (d, J=9.6 Hz, 1H), 4.06 (t, J=6.6 Hz, 1H), 3.85 (t, J=6.3 Hz, 1H), 3.78 (s, 3H), 3.67-3.61 (m, 3H), 3.01 (s, 6H).

Example 5

(E)-ethyl 3-((3aR,5R,6S,7R,7aR)-6,7-dihydroxy-2-(methylamino)-5,6,7,7a-tetrahydro-3aH-pyrano[3,2-d]thiazol-5-yl)acrylate

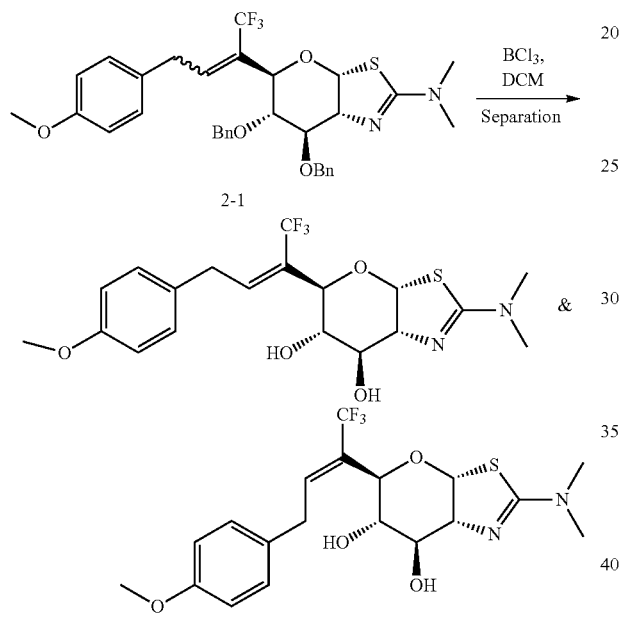

(3aR,5R,6S,7R,7aR,E)-2-(dimethylamino)-5-(1,1,1-trifluoro-4-(4-methoxyphenyl)but-2-en-2-yl)-5,6,7,7a-tetrahydro-3aH-pyrano[3,2-d]thiazole-6,7-diol & (3aR,5R,6S,7R,7aR,Z)-2-(dimethylamino)-5-(1,1,1-trifluoro-4-(4-methoxyphenyl)but-2-en-2-yl)-5,6,7,7a-tetrahydro-3aH-pyrano[3,2-d]thiazole-6,7-diol

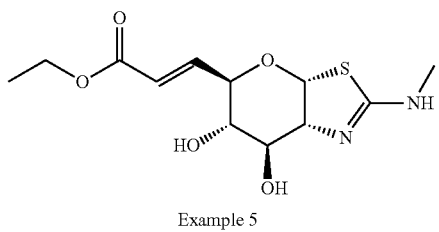 [SMILES: CCOC(=O)/C=C/[C@H]1O[C@@H]2SC(NC)=N[C@@H]2[C@@H](O)[C@@H]1O]

Example 5

A solution of 2-1 (220 mg, 0.36 mmol) in dichloromethane (15 mL) was treated with 1 N BCl3 in dichloromethane (3.6 mL, 3.6 mmol) for 2 hours at −50° C., then quenched by the addition of methanol (15 mL). Volatiles were distilled out under reduced pressure to give a residue, which was dissolved into methanol (5 mL) and neutralized by Con. NH4OH (3 ml, 26% aqueous solution). After concentration, the crude product was purified by Prep-HPLC with the following conditions [(Agilent 1200 prep HPLC): Column, Sun Fire Prep C18; mobile phase, water with 0.05% NH4OH and CH3CN (22% up to 32% in 18 min); Detector, 220 nm, Detector, 220 nm] to give (3aR,5R,6S,7R,7aR,E)-2-(dimethylamino)-5-(1,1,1-trifluoro-4-(4-methoxyphenyl)but-2-en-2-yl)-5,6,7,7a-tetrahydro-3aH-pyrano[3,2-d]thiazole-6,7-diol (12.3 mg, Faster eluting isomer by Prep-HPLC) as a Scheme 3

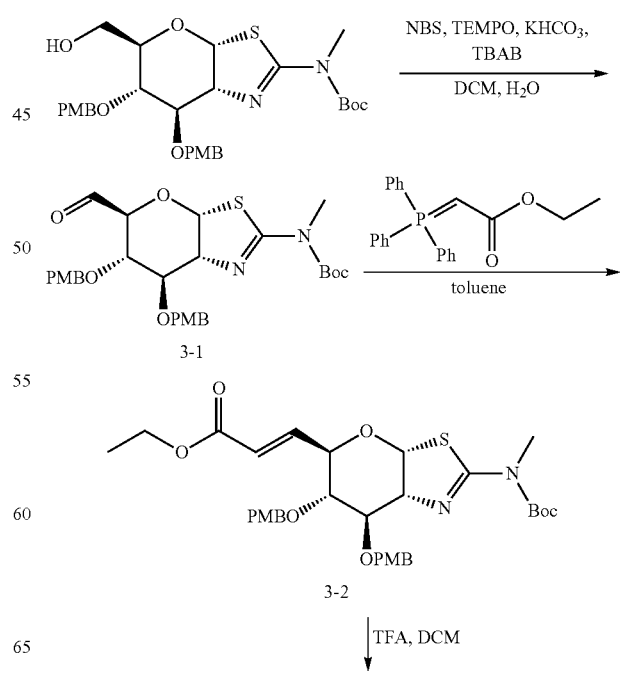

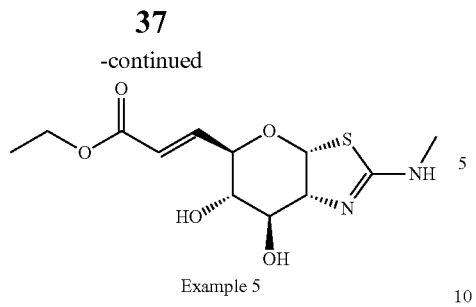

Example 5

Step 1

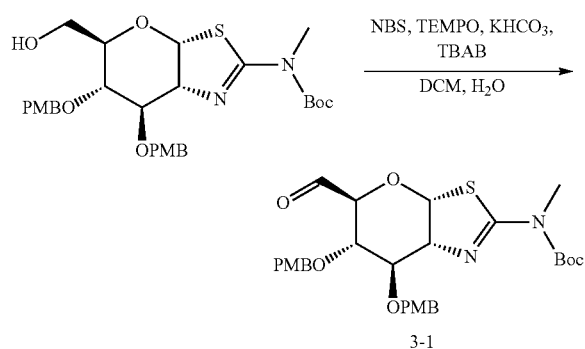

tert-butyl (3aR,5S,6S,7R,7aR)-5-formyl-6,7-bis(4-methoxybenzyloxy)-5,6,7,7a-tetrahydro-3aH-pyrano[3,2-d]thiazol-2-yl(methyl)carbamate (3-1)

To a mixture of tert-butyl (3aR,5R,6S,7R7aR)-5-(hydroxymethyl)-6,7-bis(4-methoxybenzyloxy)-5,6,7,7a-tetrahydro-3aH-pyrano[3,2-d]thiazol-2-yl(methyl) carbamate (WO2012/061972 A1) (1.5 g, 2.6 mmol), TBAB (41 mg, 0.13 mmol), KHCO₃ (1.2 g, 12 mmol) and TEMPO (20 mg, 0.13 mmol) in dichloromethane (25 mL) and H₂O (5 mL) was added NBS (498 mg, 2.8 mmol) at 15° C. After stirring for 45 min, the reaction was quenched by saturated aqueous sodium sulfite (10 mL). The organic layer was separated and the aqueous layer was extracted with dichloromethane (2×20 mL). The combined organic layer was dried over anhydrous magnesium sulfate and concentrated under reduced pressure to give a residue, which was purified by silica gel column, eluted with 20%~30% ethyl acetate in dichloromethane to afford the product as a yellow syrup (1.2 g, 77% pure), which was used directly in next step; (ES, m/z) [M+H]⁺ 573.1.

Step 2

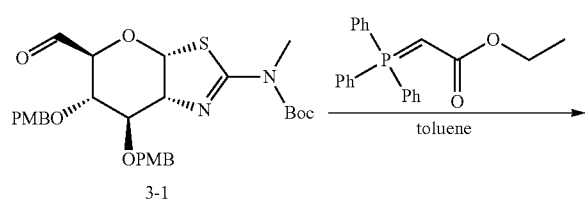

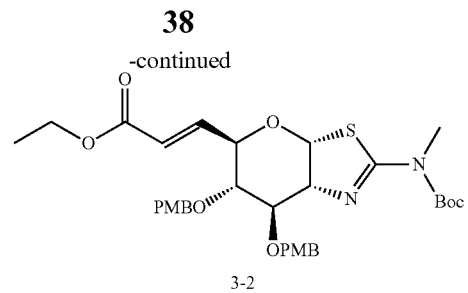

3-2

(E)-ethyl 3-((3aR,5R,6R,7R,7aR)-2-(tert-butoxycarbonyl(methyl)amino)-6,7-bis(4-methoxybenzyloxy)-5,6,7,7a-tetrahydro-3aH-pyrano[3,2-d]thiazol-5-yl)acrylate (3-2)

To a solution of 3-1 (725 mg, 1.3 mmol) in toluene (20 mL) was added (carbethoxymethylene)triphenylphosphorane (690 mg, 2.0 mmol) at room temperature. After stirring for 12 hours at 90° C., the volatiles were distilled out under reduced pressure to give a residue, which was purified by a silica gel column, eluted with 2% 20% ethyl acetate in petroleum ether to afford the title compound (577 mg, 71%) as a light yellow solid. (ES, m/z): [M+H]⁺ 643.1; ¹H NMR (300 MHz, CDCl₃) δδ 7.51-7.23 (m, 4H), 7.01-6.83 (m, 5H), 6.32 (d, J=6.3 Hz, 1H), 6.11-6.05 (m, 1H) 4.77-4.60 (m, 4H), 4.23-4.15 (m, 3H), 4.11-3.94 (m, 2H), 3.80 (s, 6H), 3.79-3.67 (m, 1H), 3.31 (s, 3H), 1.51 (s, 9H), 1.33 (t, J=6.9 Hz, 3H).

Step 3

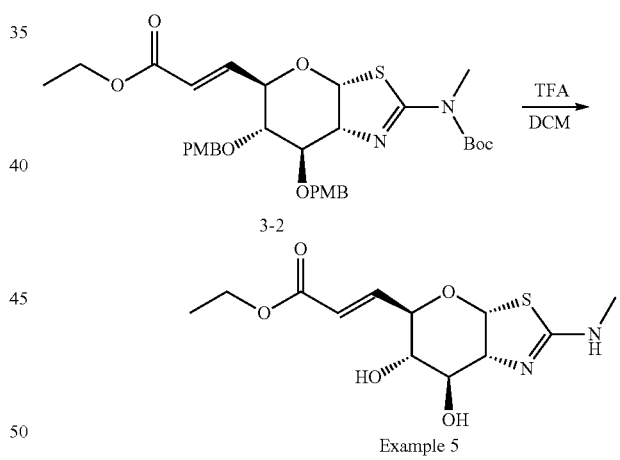

Example 5

(E)-ethyl 3-((3aR,5R,6S,7R,7aR)-6,7-dihydroxy-2-(methylamino)-5,6,7,7a-tetrahydro-3aH-pyrano[3,2-d]thiazol-5-yl)acrylate A solution of 3-2 (180 mg, 0.28 mmol) in DCM (10 mL) was treated with TFA (2 mL) for 2 hours at room temperature. Volatiles were distilled out to give a residue, which was dissolved into methanol (5 mL) and neutralized with concentrated ammonia. After concentrated under reduced pressure, the crude residue was purified by Prep HPLC [(Agilent 1200 prep HPLC): Column, Sun Fire Prep C18, 19*50 mm 5 um; mobile phase, water with 0.05% NH₄OH and CH₃CN (15% CH₃CN up to 35% in 12 min); Detector, UV 220 nm] to afford the title compound as a white solid (33 mg, 40%).

(ES, m/z)[M+H]+ 303.0; HNMR (300 MHz, CD3OD) δ 7.12-7.06 (m, 1H), 6.36 (d, J=6.6 Hz, 1H), 6.08-6.02 (m, 1H), 4.24-4.22 (m, 3H), 4.11 (t, J=6.0 Hz, 1H), 3.97 (t, J=5.4 Hz, 1H), 3.43-3.42 (m, 1H), 2.87 (s, 3H), 1.29 (t, J=6.9 Hz, 3H).

Examples 6 and 7

(3aR,5R,6S,7R,7aR)-5-((R)-1-hydroxy-3-(4-methoxyphenyl)propyl)-2-(methylamino)-5,6,7,7a-tetrahydro-3aH-pyrano[3,2-d]thiazole-6,7-diol & (3aR,5R,6S,7R,7aR)-5-((S)-1-hydroxy-3-(4-methoxyphenyl)propyl)-2-(methylamino)-5,6,7,7a-tetrahydro-3aH-pyrano[3,2-d]thiazole-6,7-diol

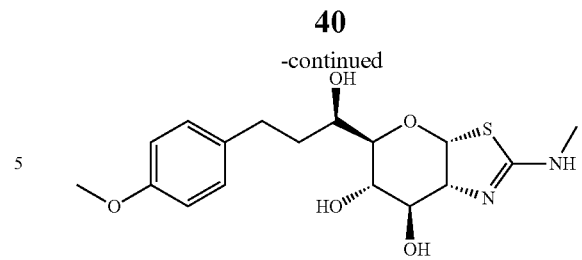

Example 6

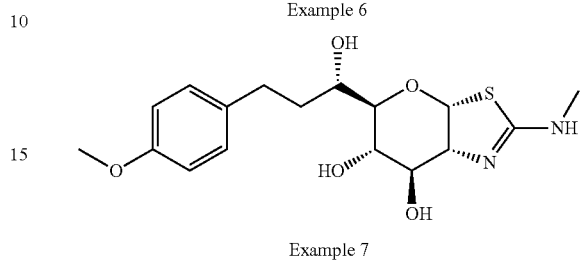

Example 7

Step 1

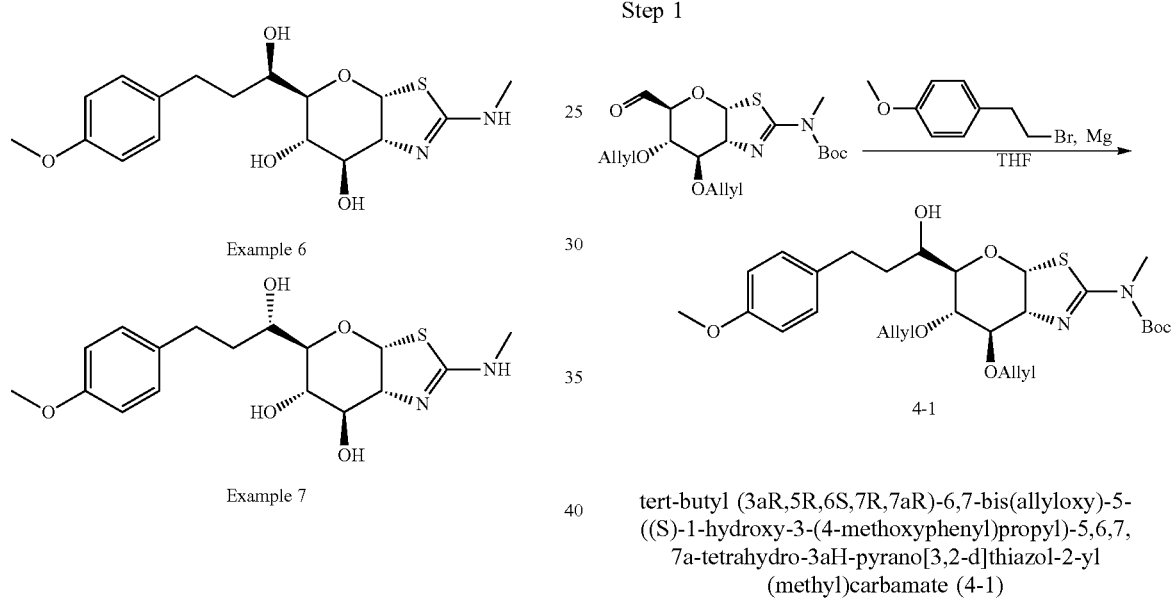

4-1 tert-butyl (3aR,5R,6S,7R,7aR)-6,7-bis(allyloxy)-5-((S)-1-hydroxy-3-(4-methoxyphenyl)propyl)-5,6,7,7a-tetrahydro-3aH-pyrano[3,2-d]thiazol-2-yl(methyl)carbamate (4-1)

A solution of (4-methoxyphenethyl) magnesium bromide in anhydrous THF (20 mL) was prepared from magnesium (144 mg, 6 mmol) and 1-(2-bromoethyl)-4-methoxybenzene (1.28 g, 6 mmol) using standard conditions. After cooling the solution to −10° C., a solution of tert-butyl (3aR,5S,6S,7R,7aR)-6,7-bis(allyloxy)-5-formyl-5,6,7,7a-tetrahydro-3aH-pyrano[3,2-d]thiazol-2-yl(methyl)carbamate (WO2012/064680A1) (824 mg, 2 mmol) in anhydrous THF (10 mL) was added dropwise over a period of 20 min. The reaction mixture was then allowed to warm to 20° C. and was stirred for additional 4 hours. Then the reaction was quenched by saturated aqueous ammonium chloride (20 mL), extracted with dichloromethane (3×30 mL). The combined organic layer was washed with brine (20 mL), dried over anhydrous magnesium sulfate and concentrated under reduced pressure to give a residue, which was purified by a silica gel column, eluted with 3%~35% ethyl acetate in petroleum ether to afford the title compound (668 mg, 61%, two epimers' ratio is 2:3 by $^1$H NMR) as a yellow syrup; (ES, m/z)[M+H]+ 549.1; $^1$H NMR (300 MHz, CDCl3) δ 7.15-7.13 (m, 2H), 6.85-6.82 (m, 2H), 6.17-6.13 (m, 1H), 5.96-5.82 (m, 2H), 5.38-5.21 (m, 4H), 4.45-4.39 (m, 1H), 4.33-4.19 (m, 4H), 4.03-3.84 (m, 3H), 3.81 (s, 3H), 3.80-

Scheme 4

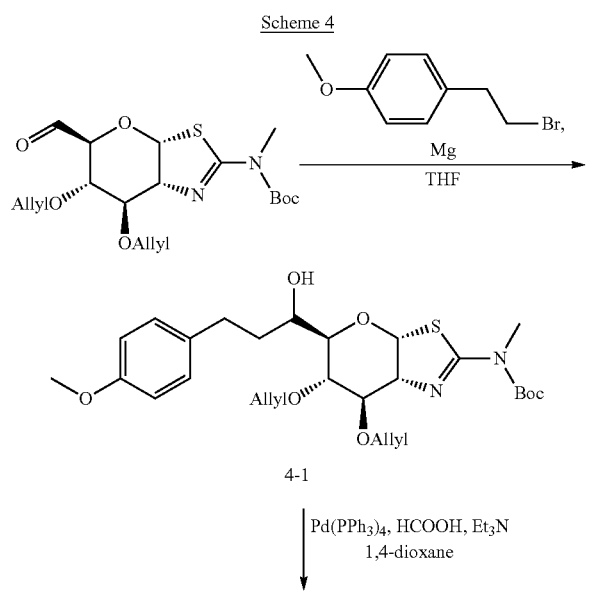

4-1

| Pd(PPh3)4, HCOOH, Et3N
| 1,4-dioxane 3.75 (m, 1H), 3.39-3.36 (m, 3H), 2.79-2.71 (m, 2H), 2.06-2.03 (m, 2H), 1.56-1.54 (m, 9H).

Step 2

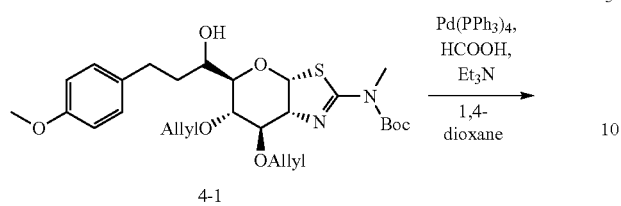

4-1

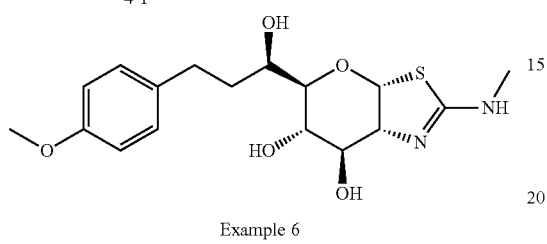

Example 6

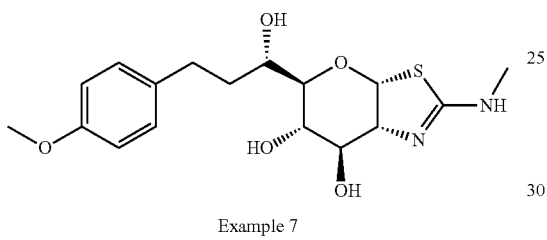

Example 7

(3aR,5R,6S,7R,7aR)-5-((R)-1-hydroxy-3-(4-methoxyphenyl)propyl)-2-(methylamino)-5,6,7,7a-tetrahydro-3aH-pyrano[3,2-d]thiazole-6,7-diol & (3aR,5R,6S,7R,7aR)-5-((S)-1-hydroxy-3-(4-methoxyphenyl)propyl)-2-(methylamino)-5,6,7,7a-tetrahydro-3aH-pyrano[3,2-d]thiazole-6,7-diol To a solution of 4-1 (330 mg, 0.6 mmol) in 1,4-dioxane (10 mL) was added Pd(PPh$_3$)$_4$(138 mg, 0.12 mmol), Et$_3$N (121 mg, 1.2 mmol), HCOOH (55 mg, 1.2 mmol) at 25° C. under N$_2$ atmosphere. After 1 hour at 60° C., additional HCOOH (276 mg, 6 mmol) was added and the mixture was stirred for additional 12 hours at 60° C., then quenched by H$_2$O (20 mL), extracted with dichloromethane (2×15 mL) to remove the organic impurities. The pH value of aqueous phase was adjusted to 7-8 by saturated aqueous NaHCO$_3$, then concentrated under reduced pressure to give a residue, which was purified by a silica gel column, eluted with 2% 10% methanol in dichloromethane to give the mixture of two epimer. Further separation by Prep HPLC [(Agilent 1200 prep HPLC): Column, Sun Fire Prep C18*50 mm 5 um; mobile phase, water with CH$_3$CN (15% CH$_3$CN up to 35% in 18 min); Detector, UV, 220 nm] to afford (3aR,5R,6S,7R,7aR)-5-((R)-1-hydroxy-3-(4-methoxyphenyl)propyl)-2-(methylamino)-5,6,7,7a-tetrahydro-3aH-pyrano[3,2-d]thiazole-6,7-diol (29.6 mg, Faster eluting isomer by Prep-HPLC) as a white solid; (ES, m/z)[M+H]$^+$ 369.0; $^1$H NMR (300 MHz, CD$_3$OD) δ 7.15 (d, J=8.4 Hz, 2H), 6.83 (d, J=8.7 Hz, 2H), 6.32 (d, J=6.3 Hz, 1H), 4.29 (t, J=6.0 Hz, 1H), 4.06-4.03 (m, 1H), 3.87-3.76 (m, 3H), 3.74 (s, 3H), 2.85 (s, 3H), 2.68-2.62 (m, 2H), 2.13-2.02 (m, 2H), 1.83-1.72 (m, 1H); and (3aR,5R,6S,7R,7aR)-5-((S)-1-hydroxy-3-(4-methoxyphenyl)propyl)-2-(methylamino)-5,6,7,7a-tetra-hydro-3aH-pyrano[3,2-d]thiazole-6,7-diol (50.9 mg, Slower eluting isomer by Prep-HPLC) as a white solid; (ES, m/z) [M+H]$^+$ 369.0; $^1$H NMR (300 MHz, CD$_3$OD) δ 7.13 (d, J=8.7 Hz, 2H), 6.83 (d, J=8.7 Hz, 2H), 6.33 (d, J=6.3 Hz, 1H), 4.13 (t, J=6.0 Hz, 1H), 4.00 (t, J=4.8 Hz, 1H), 3.81-3.78 (m, 2H), 3.76 (s, 3H), 3.44-3.33 (m, 1H), 2.85 (s, 3H), 2.74-2.60 (m, 2H), 1.90-1.78 (m, 2H).

Examples 8 and 9

(3aR,5S,6S,7R,7aR)-2-(methylamino)-5-((R)-1,1,1-trifluoro-2-hydroxy-4-(4-methoxyphenyl)butan-2-yl)-5,6,7,7a-tetrahydro-3aH-pyrano[3,2-d]thiazole-6,7-diol &

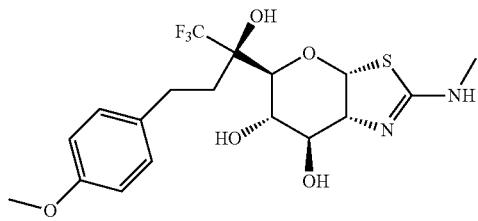

Example 6

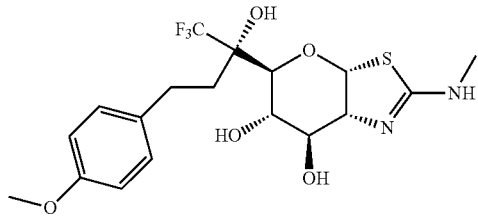

Example 7

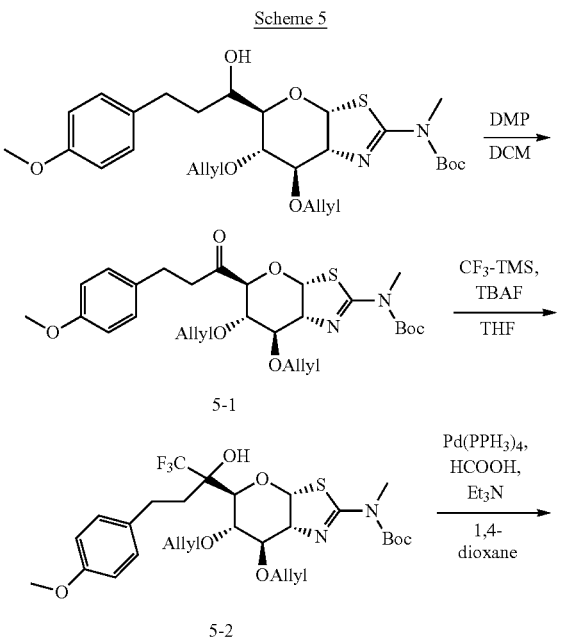

Scheme 5

-continued

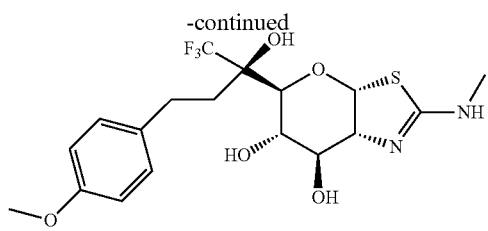

Example 8

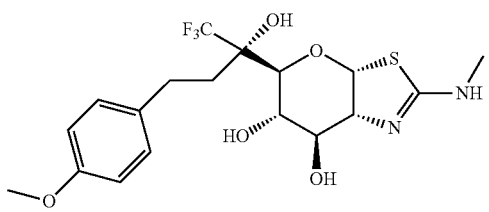

Example 9

Step 1

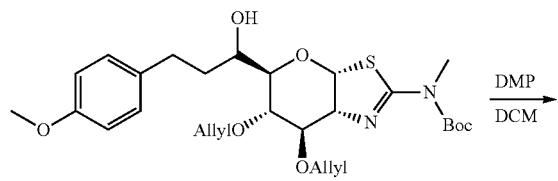

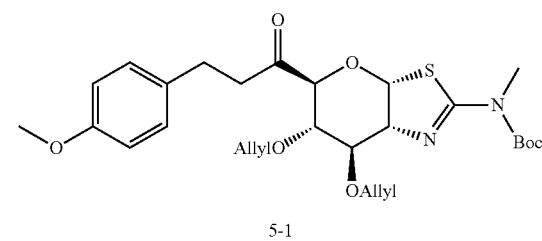

5-1 tert-butyl (3aR,5S,6S,7R,7aR)-6,7-bis(allyloxy)-5-(3-(4-methoxyphenyl)propanoyl)-5,6,7,7a-tetrahydro-3aH-pyrano[3,2-d]thiazol-2-yl(methyl)carbamate (5-1)

To a solution of tert-butyl (3aR,5R,6S,7R,7aR)-6,7-bis(allyloxy)-5-((S)-1-hydroxy-3-(4-methoxyphenyl)propyl)-5,6,7,7a-tetrahydro-3aH-pyrano[3,2-d]thiazol-2-yl(methyl)carbamate (From Example 6, step 1) (610 mg, 1.1 mmol) in dichloromethane (20 mL) was added DMP (1.2 g, 2.8 mmol) at 0° C. After stirring for 3 hours at room temperature, the reaction was quenched by saturated aqueous sodium thiosulphate (15 mL) and sodium bicarbonate (15 mL), extracted with dichloromethane (3×50 mL). The combined organic layer was washed with brine (2×30 mL), dried over anhydrous sodium sulfate and concentrated under reduced pressure to give a residue, which was purified by a silica gel column, eluted with 3%~30% ethyl acetate in petroleum ether to afford the title compound (439 mg, 72%) as a yellow syrup; (ES, m/z)[M+H]+ 547.1; $^1$H NMR (300 MHz, CDCl$_3$) δ 7.11 (d, J=8.4 Hz, 2H), 6.84 (d, J=8.4 Hz, 2H), 6.08 (d, J=4.5 Hz, 1H), 5.99-5.88 (m, 2H), 5.71-5.69 (m, 1H), 5.36-5.18 (m, 4H), 4.55-4.53 (m, 1H), 4.24-4.15 (m, 4H), 3.84-3.78 (m, 2H), 3.77 (s, 3H), 3.33 (s, 3H), 2.97-2.81 (m, 4H), 1.55 (s, 9H).

Step 2

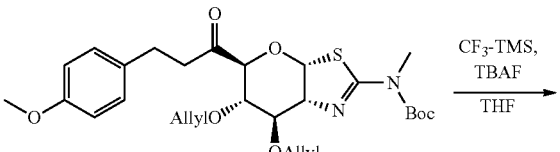

5-1

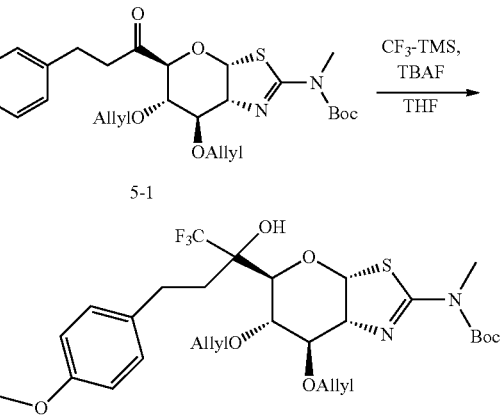

5-2 tert-butyl (3aR,5S,6S,7R,7aR)-6,7-bis(allyloxy)-5-((R)-1,1,1-trifluoro-2-hydroxy-4-(4-methoxyphenyl)butan-2-yl)-5,6,7,7a-tetrahydro-3aH-pyrano[3,2-d]thiazol-2-yl(methyl)carbamate (5-2)

A mixture of TBAF (78 mg, 0.3 mmol) and 4 A° molecule sieves in anhydrous THF (10 mL) was stirred for 30 min at 0° C. followed by the addition of a solution of 5-1 (415 mg, 0.76 mmol) and CF$_3$-TMS (536 mg, 3.8 mmol) in anhydrous THF (10 mL). After stirring for additional 12 hours at 25° C., additional TBAF (313 mg, 1.2 mmol) was added, and the mixture was stirred for 1 hour. The reaction was quenched by water (15 mL), extracted with ethyl acetate (3×30 mL), the combined organic layer was washed with brine (2×20 mL), dried over anhydrous sodium sulfate and concentrated under reduced pressure to give a residue, which was purified by a silica gel column, eluted with 3%~40% ethyl acetate in petroleum ether to afford the title compound (296 mg, 63%, two epimers' ratio is 1:1 by $^1$H NMR) as a yellow syrup; (ES, m/z)[M+H]+ 617.0; $^1$H NMR (300 MHz, CDCl$_3$) δ 7.14 (d, J=8.1 Hz, 2H), 6.86 (d, J=8.1 Hz, 2H), 6.41 (d, J=6.0 Hz, 1H), 5.97-5.85 (m, 2H), 5.33-5.16 (m, 4H), 4.34-4.31 (m, 1H), 4.21-4.12 (m, 5H), 4.11-3.86 (m, 2H), 3.79 (s, 3H), 3.21 (s, 3H), 2.81-2.74 (m, 2H), 2.06-1.99 (m, 2H), 1.56 (s, 9H).

Step 3

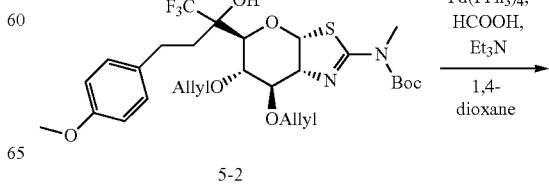

5-2

-continued

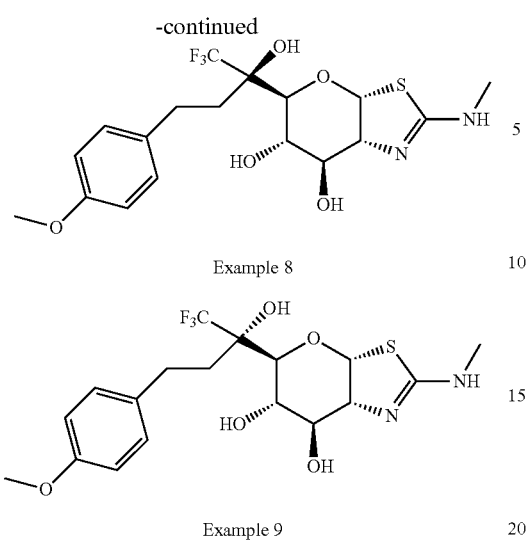

Example 8

Example 9

(3aR,5S,6S,7R,7aR)-2-(methylamino)-5-((R)-1,1,1-trifluoro-2-hydroxy-4-(4-methoxyphenyl)butan-2-yl)-5,6,7,7a-tetrahydro-3aH-pyrano[3,2-d]thiazole-6,7-diol & (3aR,5S,6S,7R,7aR)-2-(methylamino)-5-((S)-1,1,1-trifluoro-2-hydroxy-4-(4-methoxyphenyl)butan-2-yl)-5,6,7,7a-tetrahydro-3aH-pyrano[3,2-d]thiazole-6,7-diol)

To a solution of 5-2 (270 mg, 0.44 mmol) in 1,4-dioxane (10 mL) was added Pd(PPh$_3$)$_4$(104 mg, 0.09 mmol), Et$_3$N (111 mg, 1.1 mmol), HCOOH (42 mg, 0.9 mmol) at 25° C. under N$_2$ atmosphere. After 1 hour at 60° C., additional HCOOH (230 mg, 5 mmol) was added and the mixture was stirred for additional 12 hours at 60° C., then quenched by H$_2$O (20 mL), extracted with dichloromethane (2×20 mL) to remove the organic impurities. The pH value of aqueous phase was adjusted to 7-8 by saturated aqueous NaHCO$_3$, then concentrated under reduced pressure to give a residue, which was purified by a silica gel column, eluted with 2% 10% methanol in dichloromethane to give the mixture of two epimer. Further separation by Prep HPLC [(Agilent 1200 prep HPLC): Column, Sun Fire Prep C18*50 mm 5 um; mobile phase, water with CH$_3$CN (13% CH$_3$CN up to 38% in 15 min); Detector, UV, 220 nm] to afford (3aR,5S,6S,7R,7aR)-2-(methylamino)-5-((R)-1,1,1-trifluoro-2-hydroxy-4-(4-methoxyphenyl)butan-2-yl)-5,6,7,7a-tetrahydro-3aH-pyrano[3,2-d]thiazole-6,7-diol (13.3 mg, Faster eluting isomer by Prep-HPLC) as a white solid; (ES, m/z) [M+H]$^+$ 437.0; $^1$H NMR (300 MHz, CD$_3$OD) δ 7.13 (d, J=8.4 Hz, 2H), 6.83 (d, J=8.4 Hz, 2H), 6.35 (d, J=6.6 Hz, 1H), 4.32 (t, J=5.4 Hz, 1H), 4.21-4.19 (m, 1H), 4.11-4.08 (m, 1H), 3.88-3.85 (m, 1H), 3.77 (s, 3H), 2.88 (s, 3H), 2.84-2.77 (m, 2H), 2.06-2.00 (m, 2H); and (3aR,5S,6S,7R,7aR)-2-(methylamino)-5-((S)-1,1,1-trifluoro-2-hydroxy-4-(4-methoxyphenyl)butan-2-yl)-5,6,7,7a-tetrahydro-3aH-pyrano[3,2-d]thiazole-6,7-diol (10.7 mg, Slower eluting isomer by Prep-HPLC) as a white solid; (ES, m/z)[M+H]$^+$ 437.0; $^1$H NMR (300 MHz, CD$_3$OD) δ 7.12 (d, J=8.4 Hz, 2H), 6.83 (d, J=8.7 Hz, 2H), 6.40 (d, J=6.6 Hz, 1H), 4.30 (t, J=5.7 Hz, 1H), 4.13-4.06 (m, 2H), 3.94-3.91 (m, 1H), 3.77 (s, 3H), 2.90 (s, 3H), 2.77-2.59 (m, 2H), 2.02-1.96 (m, 2H).

Example 10

(3aR,5S,6S,7R,7aR)-5-(1,1-difluoro-3-(4-methoxyphenyl)propyl)-2-(methylamino)-5,6,7,7a-tetrahydro-3aH-pyrano[3,2-d]thiazole-6,7-diol

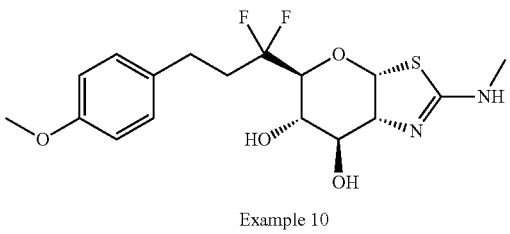

Example 10

Scheme 6

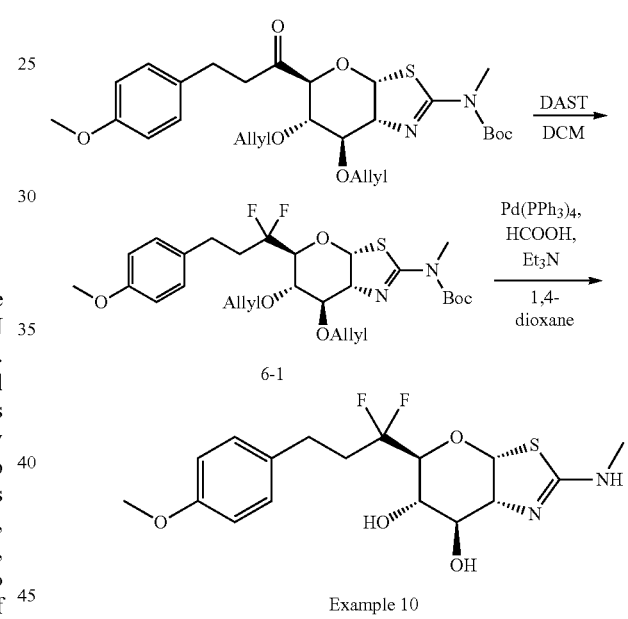

Example 10

Step 1

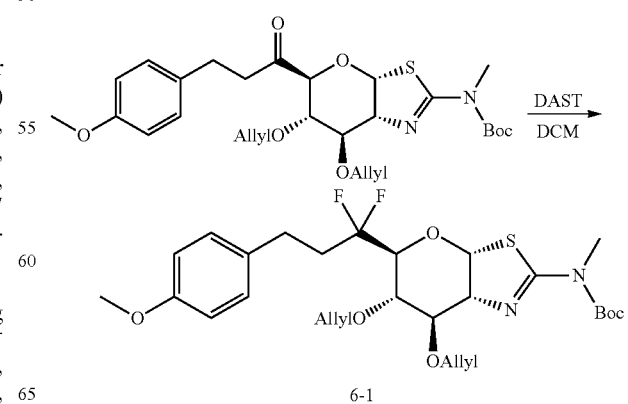

6-1 tert-butyl (3aR,5S,6S,7R,7aR)-6,7-bis(allyloxy)-5-(1,1-difluoro-3-(4-methoxyphenyl)propyl)-5,6,7,7a-tetrahydro-3aH-pyrano[3,2-d]thiazol-2-yl(methyl)carbamate (6-1)

To a solution of tert-butyl (3aR,5S,6S,7R,7aR)-6,7-bis(allyloxy)-5-(3-(4-methoxyphenyl)propanoyl)-5,6,7,7a-tetrahydro-3aH-pyrano[3,2-d]thiazol-2-yl(methyl)carbamate (From Example 9, step 1) (270 mg, 0.5 mmol) in dichloromethane (10 mL) was added DAST (403 mg, 2.5 mmol) at 0° C. After stirring for 6 hours at 25° C., the reaction was quenched by saturated aqueous sodium bicarbonate (10 mL), extracted with dichloromethane (3×20 mL). The combined organic layer was washed with brine (2×20 mL), dried over anhydrous magnesium sulfate and concentrated under reduced pressure to give a residue, which was purified by a silica gel column, eluted with 2%~30% ethyl acetate in petroleum ether to afford the title compound (154 mg, 55%); (ES, m/z) [M+H]$^+$ 569.2; $^1$H NMR (300 MHz, CDCl$_3$) δ 7.13 (d, J=8.4 Hz, 2H), 6.86 (d, J=8.4 Hz, 2H), 6.41 (d, J=6.3 Hz, 1H), 6.00-5.86 (m, 2H), 5.37-5.21 (m, 4H), 4.57-4.54 (m, 1H), 4.37-4.28 (m, 1H), 4.27-4.16 (m, 5H), 3.98-3.87 (m, 1H), 3.77 (s, 3H), 3.31 (s, 3H), 2.38-2.23 (m, 4H), 1.57 (s, 9H).

Step 2

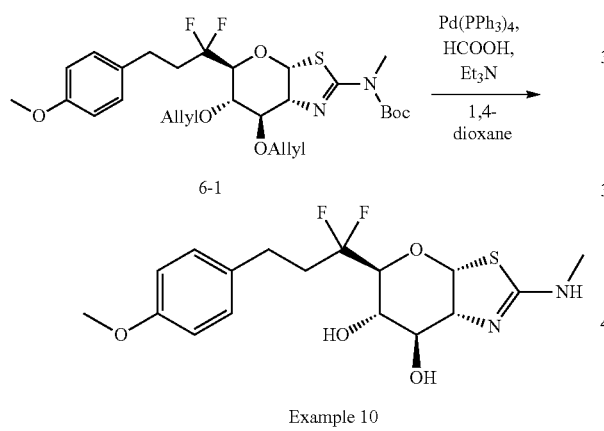

(3aR,5S,6S,7R,7aR)-5-(1,1-difluoro-3-(4-methoxyphenyl)propyl)-2-(methylamino)-5,6,7,7a-tetrahydro-3aH-pyrano[3,2-d]thiazole-6,7-diol To a solution of 6-1 (110 mg, 0.19 mmol) in 1,4-dioxane (10 mL) was added Pd(PPh$_3$)$_4$ (46 mg, 0.04 mmol), Et$_3$N (49 mg, 0.48 mmol), HCOOH (19 mg, 0.4 mmol) at 25° C. under N$_2$ atmosphere. After 1 hour at 60° C., additional HCOOH (62 mg, 2 mmol) was added and the mixture was stirred for additional 12 hours at 60° C., then quenched by H$_2$O (10 mL), extracted with dichloromethane (2×10 mL) to remove the organic impurities. The pH value of aqueous phase was adjusted to 7-8 by saturated aqueous NaHCO$_3$, then concentrated under reduced pressure to give a residue, which was purified by Prep HPLC [(Agilent 1200 prep HPLC): Column, Sun Fire Prep C18*50 mm 5 um; mobile phase, water with CH$_3$CN (18% CH$_3$CN up to 43% in 13 min); Detector, UV, 220 nm] to afford (3aR,5S,6S,7R,7aR)-5-(1,1-difluoro-3-(4-methoxyphenyl)propyl)-2-(methylamino)-5,6,7,7a-tetrahydro-3aH-pyrano[3,2-d]thiazole-6,7-diol (27 mg, 36%) as a white solid; (ES, m/z)[M+H]$^+$ 389.0; $^1$H NMR (300 MHz, CD$_3$OD) δ 7.13 (d, J=8.7 Hz, 2H), 6.85 (d, J=8.4 Hz, 2H), 6.35 (d, J=6.6 Hz, 1H), 4.52 (t, J=5.4 Hz, 1H), 4.38 (t, J=5.7 Hz, 1H), 4.11-4.09 (m, 1H), 3.79 (s, 3H), 3.78-3.76 (m, 1H), 2.98 (s, 3H), 2.29-2.18 (m, 4H).

Example 11

2-((3aR,5R,6S,7R,7aR)-2-(dimethylamino)-6,7-dihydroxy-5,6,7,7a-tetrahydro-3aH-pyrano[3,2-d]thiazol-5-yl)acetonitrile

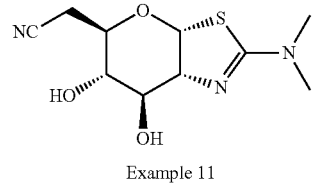 [SMILES: CN(C)C1=N[C@@H]2[C@@H](O)[C@H](O)[C@@H](CC#N)O[C@@H]2S1]

Example 11

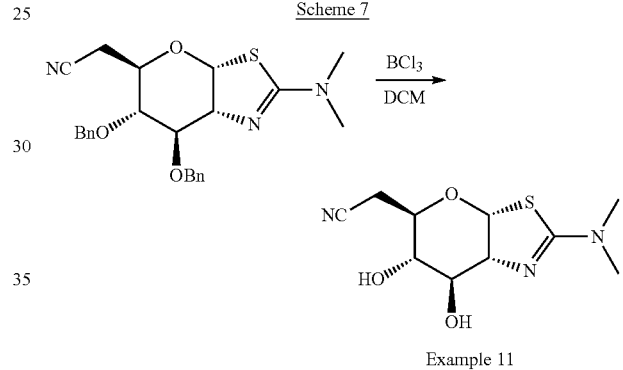

Scheme 7

Step 1

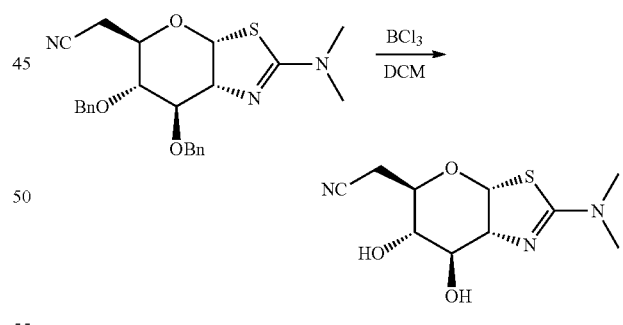

2-((3aR,5R,6S,7R,7aR)-2-(dimethylamino)-6,7-dihydroxy-5,6,7,7a-tetrahydro-3aH-pyrano[3,2-d]thiazol-5-yl)acetonitrile A solution of 2-((3aR,5R,6R,7R,7aR)-6,7-bis(benzyloxy)-2-(dimethylamino)-5,6,7,7a-tetrahydro-3aH-pyrano[3,2-d]thiazol-5-yl)acetonitrile (WO2012/064680A1) (85 mg, 0.2 mmol) in DCM (10 mL) was treated with 1 N solution of BCl$_3$ in DCM (2 mL, 2 mmol) for 2 hours at −60°

C., then quenched by the addition of methanol (10 mL). Volatiles were distilled out under reduced pressure to give a residue, which was dissolved into methanol (5 mL) and neutralized by Con. NH₄OH (3 ml, 26% aqueous solution). After concentration, the crude product was purified by Prep-HPLC with the following conditions (Agilent 1200 prep HPLC): Column, Sun Fire Prep C18; mobile phase, water with 0.05% NH₄OH and CH₃CN (15% up to 33% in 13 min); Detector, 220 nm, to afford 2-((3aR,5R,6S,7R,7aR)-2-(dimethylamino)-6,7-dihydroxy-5,6,7,7a-tetra-hydro-3aH-pyrano[3,2-d]thiazol-5-yl)acetonitrile (27 mg, 55%) as a white solid; (ES, m/z) [M+H]$^+$ 258.0; $^1$HNMR (300 MHz, D₂O) δ 6.23 (d, J=6.3 Hz, 1H), 4.09 (t, J=6.0 Hz, 1H), 3.90 (t, J=5.7 Hz, 1H), 3.84-3.81 (m, 1H), 3.52-3.47 (m, 1H), 2.91 (s, 6H), 2.88-2.75 (m, 2H).

Example 12 methyl 3-((3aR,5R,6S,7R,7aR)-6,7-dihydroxy-2-(methylamino)-5,6,7,7a-tetrahydro-3aH-pyrano[3,2-d]thiazol-5-yl)propanoate

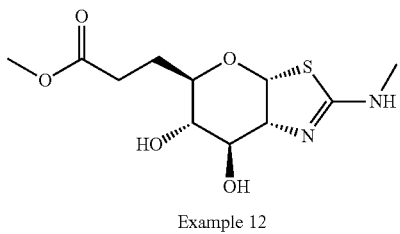

Example 12

Scheme 8

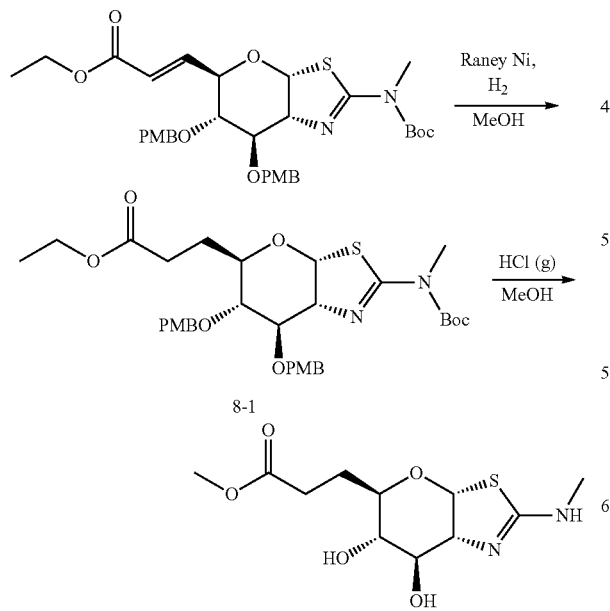

Step 1

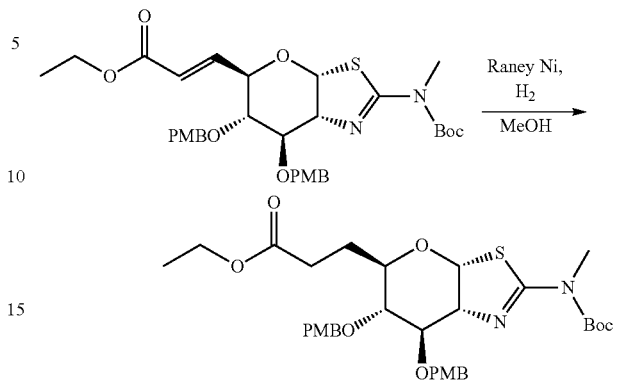

ethyl 3-((3aR,5R,6R,7R,7aR)-2-(tert-butoxycarbonyl(methyl)amino)-6,7-bis(4-methoxybenzyloxy)-5,6,7,7a-tetrahydro-3aH-pyrano[3,2-d]thiazol-5-yl)propanoate (8-1)

A mixture of (E)-ethyl 3-((3aR,5R,6R,7R,7aR)-2-(tert-butoxycarbonyl(methyl)amino)-6,7-bis(4-methoxybenzyloxy)-5,6,7,7a-tetrahydro-3aH-pyrano[3,2-d]thiazol-5-yl)acrylate (From Example 5, step 2) (350 mg, 0.55 mmol) and Raney Ni (50 mg) in methanol (20 mL) was stirred under hydrogen atmosphere (1 atm) for 12 hours at room temperature. Then the reaction mixture was filtered and the filtrate was concentrated under reduced pressure to afford a residue, which was purified by a silica gel column with 2%~30% ethyl acetate in petroleum ether to afford the title compound (231 mg, 66%) as a yellow syrup; (ES, m/z)[M+H]$^+$ 645.1; $^1$HNMR (300 MHz, CDCl₃) δ 7.35-7.19 (m, 4H), 6.92-6.81 (m, 4H), 6.02 (d, J=5.4 Hz, 1H), 4.84-4.72 (m, 1H), 4.67-4.51 (m, 4H), 4.19-4.07 (m, 2H), 4.19-4.07 (m, 2H), 3.81 (s, 6H), 3.77-3.67 (m, 1H), 3.31 (s, 3H), 2.51-2.39 (m, 2H), 1.81-1.69 (m, 2H), 1.51 (s, 9H), 1.46-1.29 (m, 3H).

Step 2

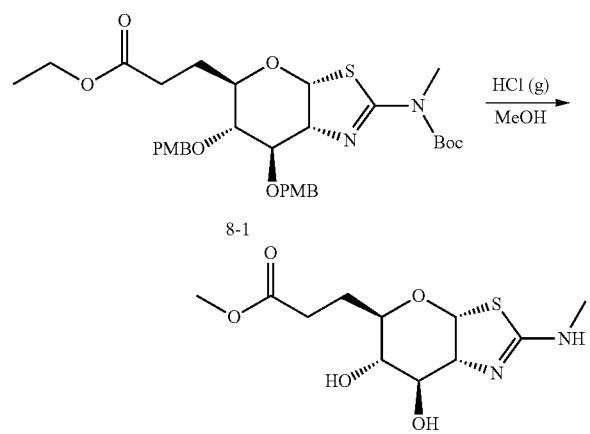

methyl 3-((3aR,5R,6S,7R,7aR)-6,7-dihydroxy-2-(methylamino)-5,6,7,7a-tetrahydro-3aH-pyrano[3,2-d]thiazol-5-yl)propanoate A solution of 8-1 (190 mg, 0.3 mmol) in MeOH (5 mL) was treated with 4 N solution of HCl (g) in MeOH (1 mL, 4 mmol) for 12 hours at room temperature. Volatiles were distilled out under reduced pressure to give a residue, which was dissolved into methanol (5 mL) and neutralized by Con. NH$_4$OH (5 ml, 26% aqueous solution). After concentration, the crude product was purified by Prep-HPLC with the following conditions (Agilent 1200 prep HPLC): Column, Sun Fire Prep C18; mobile phase, water with 0.05% NH$_4$OH and CH$_3$CN (20% up to 38% in 15 min); Detector, 220 nm, to afford methyl 3-((3aR,5R,6S,7R,7aR)-6,7-dihydroxy-2-(methylamino)-5,6,7,7a-tetrahydro-3aH-pyrano[3,2-d]thiazol-5-yl)propanoate (27 mg, 31%) as a white solid; (ES, m/z)[M+H]$^+$ 291.1; $^1$HNMR (300 MHz, D$_2$O) δ 6.43 (d, J=6.9 Hz, 1H), 4.14 (t, J=6.6 Hz, 1H), 3.86 (t, J=5.4 Hz, 1H), 3.63-3.58 (m, 1H), 3.57 (s, 3H), 3.43-3.38 (m, 1H), 2.93 (s, 3H), 2.42-2.37 (m, 2H), 2.15-2.06 (m, 1H), 1.82-1.72 (m, 1H).

Example 13

3-((3aR,5R,6S,7R,7aR)-2-(dimethylamino)-6,7-dihydroxy-5,6,7,7a-tetrahydro-3aH-pyrano[3,2-d]thiazol-5-yl)-N-methylpropanamide

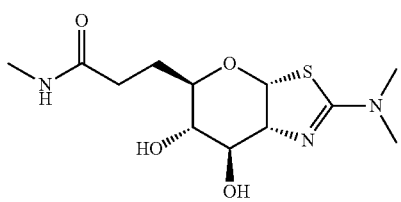

Example 13

Scheme 9

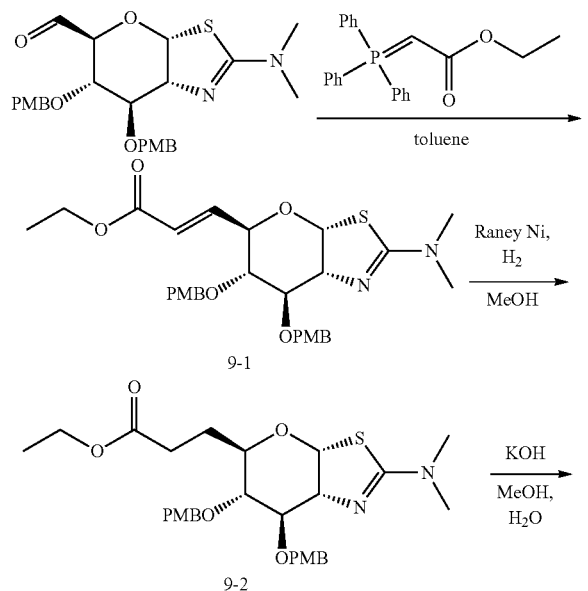

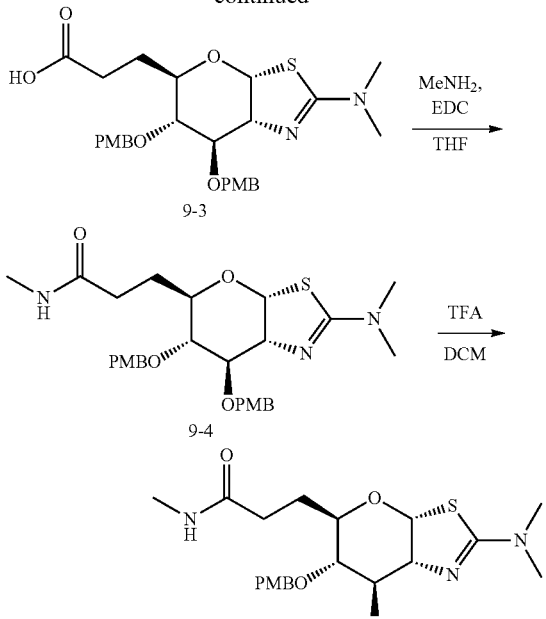

Example 13

Step 1

(E)-ethyl 3-((3aR,5R,6R,7R,7aR)-2-(dimethylamino)-6,7-bis(4-methoxybenzyloxy)-5,6,7,7a-tetrahydro-3aH-pyrano[3,2-d]thiazol-5-yl)acrylate (9-1)

To a solution of (3aR,5 S,6S,7R,7aR)-2-(dimethylamino)-6,7-bis(4-methoxybenzyloxy)-5,6,7,7a-tetrahydro-3aH-pyrano[3,2-d]thiazole-5-carbaldehyde (Cpd 11, WO2012/061972A1) (972 mg, 2 mmol) in toluene (20 mL) was added (carbethoxymethylene) triphenylphosphorane (1.05 g, 3 mmol) at room temperature. After stirring for 12 hours at 90° C., the volatiles were distilled out under reduced pressure to give a residue, which was purified by a silica gel column, eluted with 2%~25% ethyl acetate in petroleum ether to afford the title compound (810 mg, 73%) as a light yellow syrup; (ES, m/z)[M+H]$^+$ 557.1; $^1$H NMR (300 MHz, CDCl$_3$) δ 7.33-7.28 (m, 4H), 6.99-6.85 (m, 5H), 6.27 (d, J=6.6 Hz, 1H), 6.07 (dd, J, =15.9 Hz, J$_2$=1.5 Hz, 1H), 4.72-4.58 (m, 4H), 4.53-4.51 (m, 1H), 4.36-4.18 (m, 4H), 3.81 (s, 6H), 3.49-3.47 (m, 1H), 3.00 (s, 6H), 1.29 (t, J=6.9 Hz, 3H).

Step 2

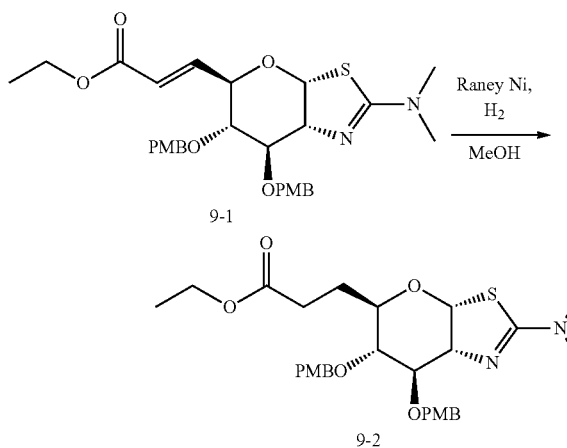

ethyl 3-((3aR,5R,6R,7R,7aR)-2-(dimethylamino)-6,
7-bis(4-methoxybenzyloxy)-5,6,7,7a-tetrahydro-
3aH-pyrano[3,2-d]thiazol-5-yl)propanoate (9-2)

A mixture of 9-1 (895 mg, 1.6 mmol) and Raney Ni (100 mg) in methanol (20 mL) was stirred under hydrogen atmosphere (1 atm) for 12 hours at room temperature. Then the reaction mixture was filtered and the filtrate was concentrated under reduced pressure to afford a residue, which was purified by a silica gel column with 2%-30% ethyl acetate in petroleum ether to afford the title compound (670 mg, 75%) as a yellow syrup; (ES, m/z)[M+H]$^+$ 559.1; $^1$H NMR (300 MHz, CDCl$_3$) δ 7.37-7.21 (m, 4H), 6.99-6.85 (m, 4H), 6.07 (d, J=6.3 Hz, 1H), 4.77-4.55 (m, 5H), 4.21-4.12 (m, 2H), 4.12-3.88 (m, 3H), 3.81 (s, 6H), 3.03 (s, 6H), 2.58-2.43 (m, 2H), 1.88-1.71 (m, 2H), 1.41-1.25 (m, 3H).

Step 3

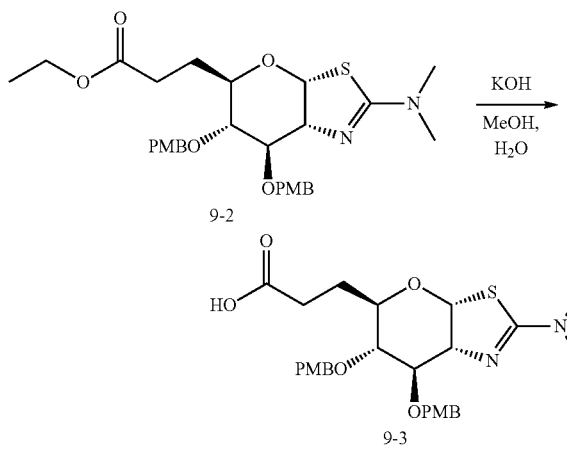

3-((3aR,5R,6R,7R,7aR)-2-(dimethylamino)-6,7-bis
(4-methoxybenzyloxy)-5,6,7,7a-tetrahydro-3aH-
pyrano[3,2-d]thiazol-5-yl)propanoic acid (9-3)

A solution of 9-2 (660 mg, 1.18 mmol) in methanol (20 mL) and water (2 mL) was treated for potassium hydroxide (280 mg, 5.00 mmol) for 2 hours at 40° C. Volatiles were distilled out under reduced pressure to give a residue, which was dissolved into water (20 mL), extracted with dichloromethane (2×20 mL) to remove the organic impurities. Then the pH value of aqueous phase was adjusted to 3 by diluted hydrogen chloride. Extracted with dichloromethane (3×30 mL), and the combined organic layer was washed with brine (2×20 mL), dried over anhydrous sodium sulfate and concentrated under reduced pressure to give the title compound (475 mg, 75%) as a yellow syrup; (ES, m/z) [M+H]+ 531.1; 1H NMR (300 MHz, CDCl3) δ 7.31-7.25 (m, 4H), 6.94-6.85 (m, 4H), 6.35 (d, J=6.0 Hz, 1H), 4.91-4.83 (m, 1H), 4.79-4.58 (m, 5H), 4.19-4.07 (m, 1H), 3.80 (s, 6H), 3.55-3.46 (m, 1H), 3.12 (s, 6H), 2.21-2.07 (m, 2H), 1.88-1.67 (m, 2H).

Step 4

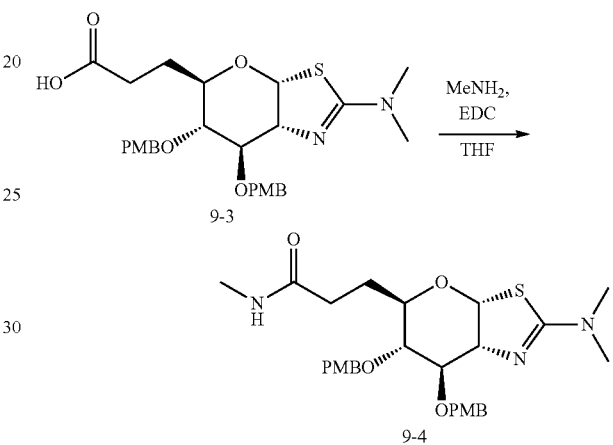

3-((3aR,5R,6R,7R,7aR)-2-(dimethylamino)-6,7-bis
(4-methoxybenzyloxy)-5,6,7,7a-tetrahydro-3aH-
pyrano[3,2-d]thiazol-5-yl)-N-methylpropanamide
(9-4)

A solution of 9-3 (300 mg, 0.57 mmol) and EDCI (325 mg, 1.7 mmol) in THF (5 mL) was treated with 2 N solution of methanamine in THF (3 ml, 6 mmol) for 12 hours at 50° C. Then the reaction was quenched by water (10 mL) and volatiles were distilled out under reduced pressure to give a residue, which was purified by a silica gel column with 2%-33% ethyl acetate in petroleum ether to afford the title compound (190 mg, 62%) as a yellow syrup; (ES, m/z) [M+H]$^+$ 544.0; $^1$H NMR (300 MHz, CDCl$_3$) δ 7.33-7.27 (m, 4H), 6.98-6.84 (m, 4H), 6.37 (d, J=6.3 Hz, 1H), 4.83-4.61 (m, 5H), 4.34-4.22 (m, 1H), 4.11-4.03 (m, 1H), 3.83 (s, 6H), 3.73-3.66 (m, 1H), 3.07 (s, 6H), 2.77 (s, 3H), 2.21-2.06 (m, 2H), 1.92-1.64 (m, 2H).

Step 5

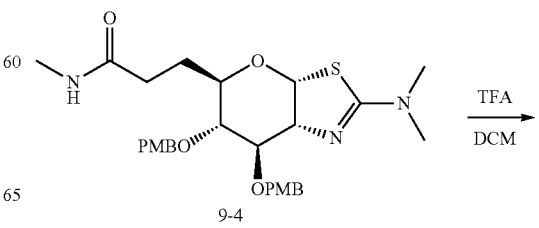

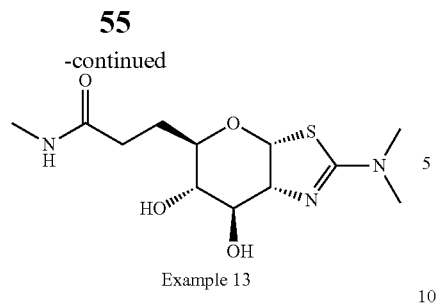

Example 13

3-((3aR,5R,6S,7R,7aR)-2-(dimethylamino)-6,7-dihydroxy-5,6,7,7a-tetrahydro-3aH-pyrano[3,2-d]thiazol-5-yl)-N-methylpropanamide A solution of 9-4 (120 mg, 0.13 mmol) in dichloromethane (10 mL) was treated with trifluoroacetic acid (1 mL) for 2 hours at room temperature. Volatiles were distilled out under reduced pressure to give a residue, which was dissolved into methanol (5 mL) and neutralized by Con. NH$_4$OH (5 ml, 26% aqueous solution). After concentration, the crude product was purified by Prep-HPLC with the following conditions (Agilent 1200 prep HPLC): Column, Sun Fire Prep C18; mobile phase, water with 0.05% NH$_4$OH and CH$_3$CN (15% up to 42% in 15 min); Detector, 220 nm, to afford 3-((3aR,5R,6S,7R,7aR)-2-(dimethylamino)-6,7-dihydroxy-5,6,7,7a-tetrahydro-3aH-pyrano[3,2-d]thiazol-5-yl)-N-methylpropanamide (22.3 mg, 33%) as a white solid; (ES, m/z)[M+H]$^+$ 304.1; $^1$H NMR (300 MHz, D$_2$O) δ 6.15 (d, J=6.6 Hz, 1H), 4.09 (t, J=6.0 Hz, 1H), 3.89 (t, J=4.8 Hz, 1H), 3.39-3.36 (m, 2H), 2.90 (s, 6H), 2.63 (s, 3H), 2.26-2.22 (m, 2H), 2.07-1.97 (m, 1H), 1.70-1.62 (m, 1H).

Example 14

(3aR,5R,6S,7R,7aR)-2-(methylamino)-5-(prop-1-en-2-yl)-5,6,7,7a-tetrahydro-3aH-pyrano[3,2-d]thiazole-6,7-diol 2,2,2-trifluoroacetate

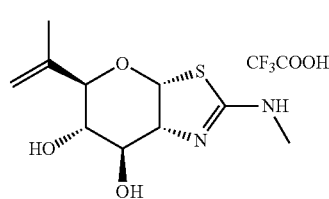

Example 14

Scheme 10

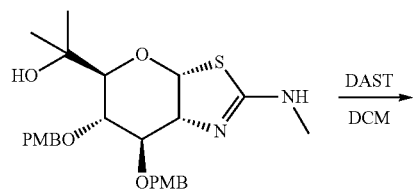

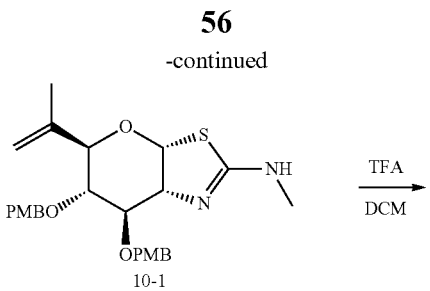
10-1

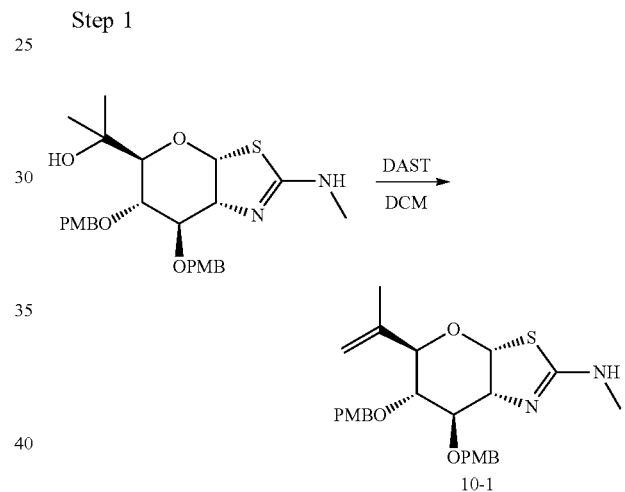

Example 14

Step 1

(3aR,5R,6R,7R,7aR)-6,7-bis(4-methoxybenzyloxy-N-methyl-5-(prop-1-en-2-yl)-5,6,7,7a-tetrahydro-3aH-pyrano[3,2-d]thiazol-2-amine (10-1)

To a solution of 2-((3aR,5S,6S,7R,7aR)-6,7-bis(4-methoxybenzyloxy)-2-(methylamino)-5,6,7,7a-tetrahydro-3aH-pyrano[3,2-d]thiazol-5-yl)propan-2-ol (WO2012/061972 A1) (450 mg, 0.9 mmol) in DCM (20 mL) was added DAST (725 mg, 4.5 mmol) at −78° C. After stirring for 1.5 hours at 0° C., the reaction was quenched by saturated aqueous sodium bicarbonate (20 mL), extracted with dichloromethane (2×30 mL). The combined organic layer was dried over anhydrous sodium sulfate and concentrated under reduced pressure to give a residue, which was purified by a silica gel column, eluted with 2%-15% ethyl acetate in petroleum ether to afford 7-1 (95 mg, 21%); (ES, m/z): [M+H]$^+$ 485.0; $^1$H NMR (300 MHz, CDCl$_3$) δ 7.35-7.22 (m, 4H), 6.99-6.84 (m, 4H), 6.42-6.36 (m, 1H), 5.12 (s, 1H), 5.10 (s, 1H), 4.77-4.60 (m, 4H), 4.19-4.09 (m, 2H), 3.94-3.82 (m, 1H), 3.81 (s, 6H), 3.79-3.67 (m, 1H), 3.00 (s, 3H), 1.77 (s, 3H).

Step 2

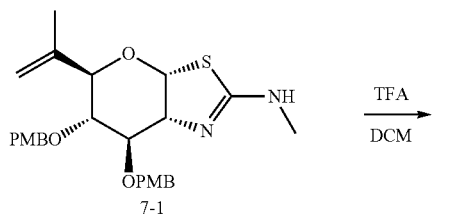

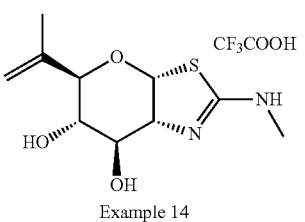

Example 14

(3aR,5R,6S,7R,7aR)-2-(methylamino)-5-(prop-1-en-2-yl)-5,6,7,7a-tetrahydro-3aH-pyrano[3,2-d]thiazole-6,7-diol 2,2,2-trifluoroacetate A solution of 7-1 (95 mg, 0.2 mmol) in DCM (10 mL) was treated with TFA (2 mL) for 2 hours at room temperature. Then volatiles were distilled out to give a residue, which was purified by Prep HPLC [(Agilent 1200 prep HPLC): Column, Sun Fire Prep C18, 19*50 mm 5 um; mobile phase, water with 0.05% TFA and CH$_3$CN (15% CH$_3$CN up to 30% in 13 min); Detector, UV 220 nm] to afford the title compound (19 mg, 27%) as a white solid; (ES, m/z): [M+H]$^+$ 245.0; $^1$H NMR (300 MHz, D$_2$O) δ 6.61-6.57 (m, 1H), 5.11 (s, 1H), 5.10 (s, 1H), 4.19-4.09 (m, 2H), 3.94-3.84 (m, 1H), 3.66-3.58 (m, 1H), 2.97 (s, 3H), 1.71 (s, 3H).

Example 15

(3aR,5R,6S,7R,7aR)-2-(methylamino)-5-(3,3,3-trifluoroprop-1-en-2-yl)-5,6,7,7a-tetrahydro-3aH-pyrano[3,2-d]thiazole-6,7-diol

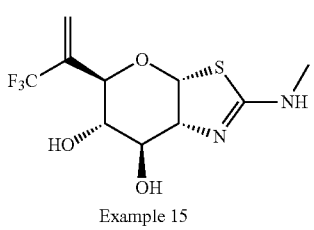 [SMILES: C=C([C@H]1O[C@@H]2SC(NC)=N[C@@H]2[C@@H](O)[C@@H]1O)C(F)(F)F]

Example 15

Scheme 11

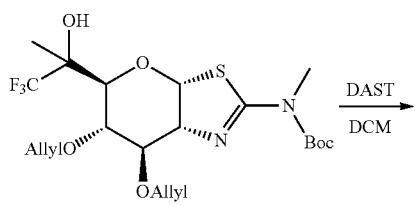

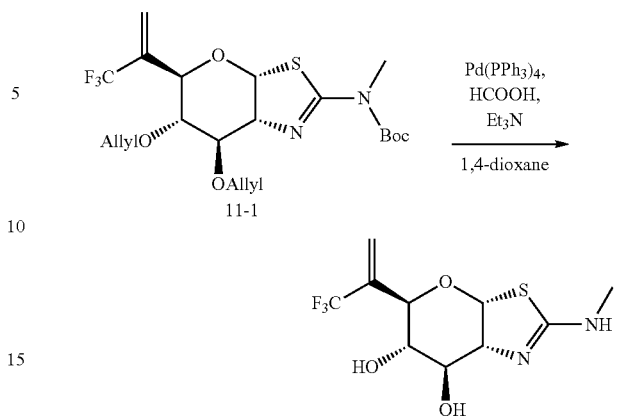

Example 15

Step 1

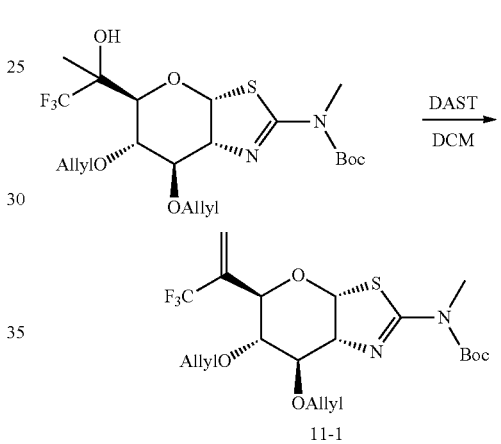

tert-butyl (3aR,5R,6R,7R,7aR)-6,7-bis(allyloxy)-5-(3,3,3-trifluoroprop-1-en-2-yl)-5,6,7,7a-tetrahydro-3aH-pyrano[3,2-d]thiazol-2-yl(methyl)carbamate (11-1)

To a solution of tert-butyl (3aR,5S,6S,7R,7aR)-6,7-bis(allyloxy)-5-((S)-1,1,1-trifluoro-2-hydroxypropan-2-yl)-5,6,7,7a-tetrahydro-3aH-pyrano[3,2-d] thiazol-2-yl(methyl)carbamate (850 mg, 1.7 mmol) in anhydrous dichloromethane (20 mL) was treated with DAST (2.7 g, 17 mmol) for 2 hours at room temperature. The reaction was quenched by saturated aqueous sodium bicarbonate (20 mL) and extracted with dichloromethane (3×50 mL), the combined organic layer was dried over anhydrous sodium sulfate and concentrated under reduced pressure to give a residue, which was purified by a silica gel column, eluted with 5% 15% ethyl acetate in petroleum ether to afford the title compound (477 mg, 58%) as a yellow syrup; (ES, m/z) [M+H]$^+$ 479.0; $^1$H NMR (300 MHz, CDCl$_3$) δ 6.32-6.30 (m, 1H), 6.15 (s, 1H), 5.99-5.81 (m, 3H), 5.37-5.19 (m, 4H), 4.45-4.00 (m, 6H), 3.96-3.92 (m, 1H), 3.65-3.61 (m, 1H), 3.33 (s, 3H), 1.54-1.56 (m, 9H).

Step 2

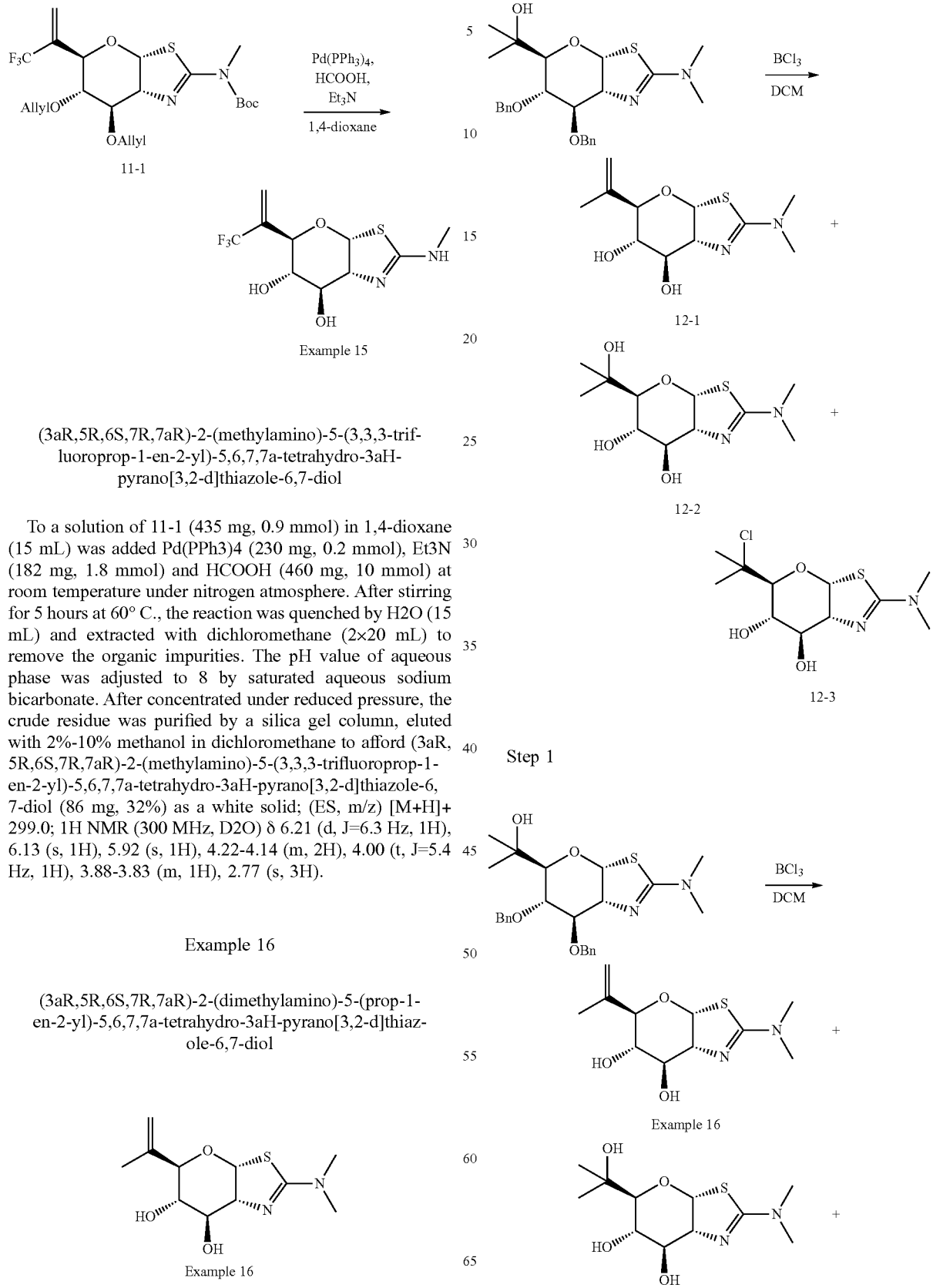

Example 15

(3aR,5R,6S,7R,7aR)-2-(methylamino)-5-(3,3,3-trif-
luoroprop-1-en-2-yl)-5,6,7,7a-tetrahydro-3aH-
pyrano[3,2-d]thiazole-6,7-diol To a solution of 11-1 (435 mg, 0.9 mmol) in 1,4-dioxane (15 mL) was added Pd(PPh3)4 (230 mg, 0.2 mmol), Et3N (182 mg, 1.8 mmol) and HCOOH (460 mg, 10 mmol) at room temperature under nitrogen atmosphere. After stirring for 5 hours at 60° C., the reaction was quenched by H2O (15 mL) and extracted with dichloromethane (2×20 mL) to remove the organic impurities. The pH value of aqueous phase was adjusted to 8 by saturated aqueous sodium bicarbonate. After concentrated under reduced pressure, the crude residue was purified by a silica gel column, eluted with 2%-10% methanol in dichloromethane to afford (3aR, 5R,6S,7R,7aR)-2-(methylamino)-5-(3,3,3-trifluoroprop-1-en-2-yl)-5,6,7,7a-tetrahydro-3aH-pyrano[3,2-d]thiazole-6,7-diol (86 mg, 32%) as a white solid; (ES, m/z) [M+H]+ 299.0; 1H NMR (300 MHz, D2O) δ 6.21 (d, J=6.3 Hz, 1H), 6.13 (s, 1H), 5.92 (s, 1H), 4.22-4.14 (m, 2H), 4.00 (t, J=5.4 Hz, 1H), 3.88-3.83 (m, 1H), 2.77 (s, 3H).

Example 16

(3aR,5R,6S,7R,7aR)-2-(dimethylamino)-5-(prop-1-
en-2-yl)-5,6,7,7a-tetrahydro-3aH-pyrano[3,2-d]thiaz-
ole-6,7-diol Example 16

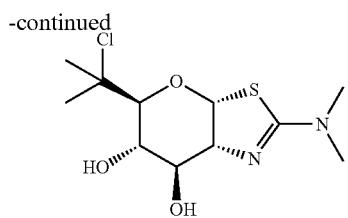

3aR,5R,6S,7R,7aR)-2-(dimethylamino)-5-(prop-1-en-2-yl)-5,6,7,7a-tetrahydro-3aH-pyrano[3,2-d]thiazole-6,7-diol A solution of 2-((3aR,5S,6S,7R,7aR)-6,7-bis(benzyloxy)-2-(dimethylamino)-5,6,7,7a-tetrahydro-3aH-pyrano[3,2-d]thiazol-5-yl)propan-2-ol (WO2012/061972 A1), (1.2 g, 2.6 mmol) in dichloromethane (150 mL) was treated with 1N solution of $BCl_3$ in dichloromethane (26 mL, 26 mmol) for 2 hours at −60° C., then quenched by the addition of methanol (60 mL). Volatiles were distilled out under reduced pressure to give a residue, which was dissolved into methanol (35 mL) and neutralized by Con. $NH_4OH$. After concentration, the crude product purificated by Prep-HPLC with the following conditions [(Agilent 1200 prep HPLC): Column, Sun Fire Prep C18; mobile phase, water with 0.05% $NH_4OH$ and $CH_3CN$ (18% up to 32% in 18 min); Detector, 220 nm, Detector, 220 nm] to give the title compound (53 mg, 8%) as a white solid, (ES, m/z): $[M+H]^+$ 259.0; $^1H$ NMR (300 MHz, $D_2O$) δ 6.22 (d, J=6.3 Hz, 1H), 5.02 (s, 2H), 4.06-3.95 (m, 2H), 3.86 (t, J=6.0 Hz, 1H), 3.63-3.58 (m, 1H), 2.90 (s, 6H), 1.66 (s, 3H); And tertiary alcohol 12-2(406 mg, 56%) as a white solid, $[M+H]^+$ 276.9; $^1H$ NMR (300 MHz, $D_2O$) δ 6.24 (d, J=6.9 Hz, 1H), 4.73-4.71 (m, 1H), 4.15-4.13 (m, 1H), 3.74-3.71 (m, 1H), 3.21-3.18 (m, 1H), 2.91 (s, 6H), 1.15 (s, 3H), 1.11 (s, 3H); And the chloride 12-3(108 mg, 14%), $[M+H]^+$ 295.0; $^1H$ NMR (300 MHz, $D_2O$) δ 6.45 (d, J=7.2 Hz, 1H), 4.59-4.55 (m, 1H), 4.39-4.37 (m, 1H), 4.11-4.07 (m, 1H), 3.51 (d, J=7.8 Hz, 1H), 3.10 (s, 6H), 1.69 (s, 3H), 1.67 (s, 3H)

Compounds in the following table were prepared by methods similar to those described above for Examples 1-16.

TABLE 1

| Example | Structure | Name | MH+ |
|---|---|---|---|
| 17 | 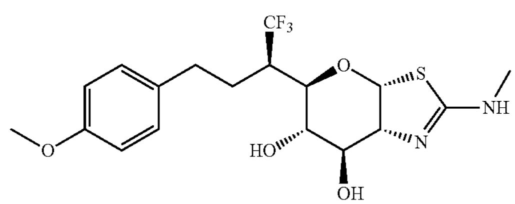 | (3aR,5R,6S,7R,7aR)-2-(methylamino)-5-((R)-1,1,1-trifluoro-4-(4-methoxyphenyl)butan-2-yl)-5,6,7,7a-tetrahydro-3aH-pyrano[3,2-d]thiazole-6,7-diol | 421.0 |
| 18 | 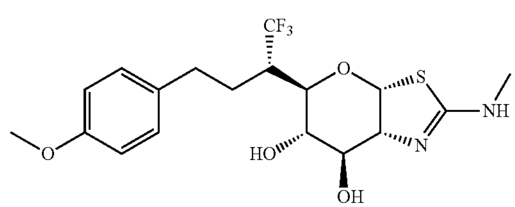 | (3aR,5R,6S,7R,7aR)-2-(methylamino)-5-(1,1,1-trifluoro-4-(4-methoxyphenyl)butan-2-yl)-5,6,7,7a-tetrahydro-3aH-pyrano[3,2-d]thiazole-6,7-diol | 421.0 |
| 19 | 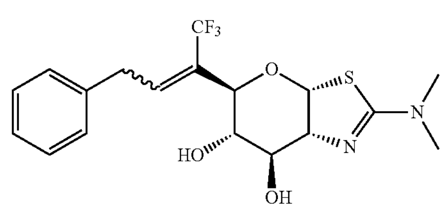 [SMILES: CN(C)C1=N[C@@H]2[C@@H](O)[C@H](O)[C@@H](C(=CCc3ccccc3)C(F)(F)F)O[C@@H]2S1] | (3aR,5R,6S,7R,7aR)-2-(dimethylamino)-5-(1,1,1-trifluoro-4-phenylbut-2-en-2-yl)-5,6,7,7a-tetrahydro-3aH-pyrano[3,2-d]thiazole-6,7-diol | 403.0 |
| 20 | 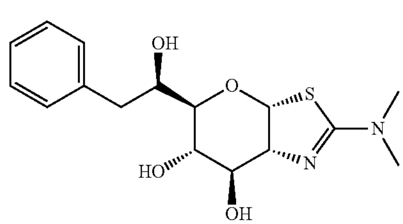 [SMILES: CN(C)C1=N[C@@H]2[C@@H](O)[C@H](O)[C@@H]([C@H](O)Cc3ccccc3)O[C@@H]2S1] | (3aR,5R,6S,7R,7aR)-2-(dimethylamino)-5-((R)-1-hydroxy-2-phenylethyl)-5,6,7,7a-tetrahydro-3aH-pyrano[3,2-d]thiazole-6,7-diol | 339.0 |

TABLE 1-continued

| Example | Structure | Name | MH+ |
|---|---|---|---|
| 21 | 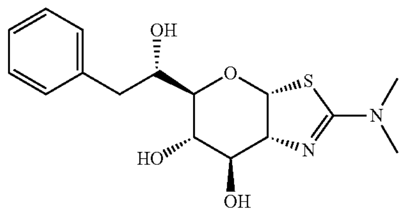 [SMILES: CN(C)C1=N[C@@H]2[C@@H](O)[C@H](O)[C@@H]([C@@H](O)Cc3ccccc3)O[C@@H]2S1] | (3aR,5R,6S,7R,7aR)-2-(dimethylamino)-5-((S)-1-hydroxy-2-phenylethyl)-5,6,7,7a-tetrahydro-3aH-pyrano[3,2-d]thiazole-6,7-diol | 339.1 |
| 22 | 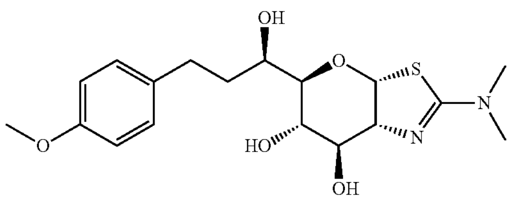 | (3aR,5R,6S,7R,7aR)-2-(dimethylamino)-5-((R)-1-hydroxy-3-(4-methoxyphenyl)propyl)-5,6,7,7a-tetrahydro-3aH-pyrano[3,2-d]thiazole-6,7-diol | 383.0 |
| 23 | 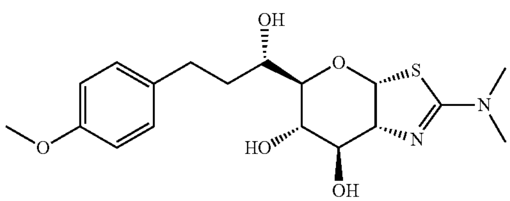 | (3aR,5R,6S,7R,7aR)-2-(dimethylamino)-5-((S)-1-hydroxy-3-(4-methoxyphenyl)propyl)-5,6,7,7a-tetrahydro-3aH-pyrano[3,2-d]thiazole-6,7-diol | 383.0 |
| 24 | 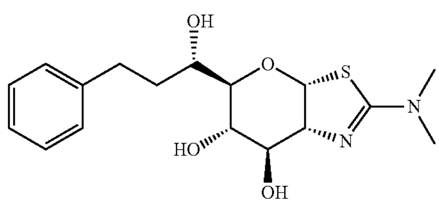 [SMILES: CN(C)C1=N[C@@H]2[C@@H](O)[C@H](O)[C@@H]([C@@H](O)CCc3ccccc3)O[C@@H]2S1] | (3aR,5R,6S,7R,7aR)-2-(dimethylamino)-5-((S)-1-hydroxy-3-phenylpropyl)-5,6,7,7a-tetrahydro-3aH-pyrano[3,2-d]thiazole-6,7-diol | 353.0 |
| 25 | 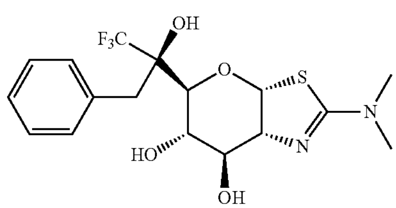 [SMILES: CN(C)C1=N[C@@H]2[C@@H](O)[C@H](O)[C@@H]([C@](O)(Cc3ccccc3)C(F)(F)F)O[C@@H]2S1] | (3aR,5S,6S,7R,7aR)-2-(dimethylamino)-5-((R)-1,1,1-trifluoro-2-hydroxy-3-phenylpropan-2-yl)-5,6,7,7a-tetrahydro-3aH-pyrano[3,2-d]thiazole-6,7-diol | 407.0 |
| 26 | 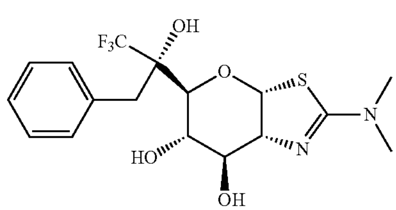 [SMILES: CN(C)C1=N[C@@H]2[C@@H](O)[C@H](O)[C@@H]([C@@](O)(Cc3ccccc3)C(F)(F)F)O[C@@H]2S1] | (3aR,5S,6S,7R,7aR)-2-(dimethylamino)-5-(1,1,1-trifluoro-2-hydroxy-3-phenylpropan-2-yl)-5,6,7,7a-tetrahydro-3aH-pyrano[3,2-d]thiazole-6,7-diol | 407.0 |
| 27 | 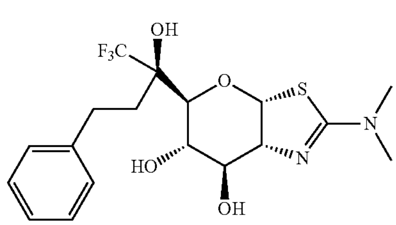 [SMILES: CN(C)C1=N[C@@H]2[C@@H](O)[C@H](O)[C@@H]([C@](O)(CCc3ccccc3)C(F)(F)F)O[C@@H]2S1] | (3aR,5S,6S,7R,7aR)-2-(dimethylamino)-5-((S)-1,1,1-trifluoro-2-hydroxy-4-phenylbutan-2-yl)-5,6,7,7a-tetrahydro-3aH-pyrano[3,2-d]thiazole-6,7-diol | 421.0 |

TABLE 1-continued

| Example | Name | MH+ |
|---|---|---|
| 28 | (3aR,5S,6S,7R,7aR)-2-(dimethylamino)-5-(1,1,1-trifluoro-2-hydroxy-4-phenylbutan-2-yl)-5,6,7,7a-tetrahydro-3aH-pyrano[3,2-d]thiazole-6,7-diol | 421.0 |
| 29 | (3aR,5S,6S,7R,7aR)-2-(dimethylamino)-5-((S)-1,1,1-trifluoro-2-hydroxy-4-(4-methoxyphenyl)butan-2-yl)-5,6,7,7a-tetrahydro-3aH-pyrano[3,2-d]thiazole-6,7-diol | 451.0 |
| 30 | (3aR,5S,6S,7R,7aR)-2-(dimethylamino)-5-(1,1,1-trifluoro-2-hydroxy-4-(4-methoxyphenyl)butan-2-yl)-5,6,7,7a-tetrahydro-3aH-pyrano[3,2-d]thiazole-6,7-diol | 451.0 |
| 31 | 2-((3aR,5R,6S,7R,7aR)-6,7-dihydroxy-2-(methylamino)-5,6,7,7a-tetrahydro-3aH-pyrano[3,2-d]thiazol-5-yl)acetonitrile | 270.0 |
| 32 | 2-((3aR,5R,6S,7R,7aR)-2-(allylamino)-6,7-dihydroxy-5,6,7,7a-tetrahydro-3aH-pyrano[3,2-d]thiazol-5-yl)acetonitrile | 243.9 |
| 33 | 3-((3aR,5R,6S,7R,7aR)-2-(dimethylamino)-6,7-dihydroxy-5,6,7,7a-tetrahydro-3aH-pyrano[3,2-d]thiazol-5-yl)-N,N-dimethylpropanamide | 318.0 |
| 34 | (3aR,5R,6S,7R,7aR)-5-[3-(4-methoxyphenyl)propyl]-2-(methylamino)-5,6,7,7a-tetrahydro-3aH-pyrano[3,2-d][1,3]thiazole-6,7-diol | 353.4 |

Example 35

(3aR,5S,6S,7R,7aR)-6,7-dihydroxy-N-methyl-2-(methylamino)-5,6,7,7a-tetrahydro-3aH-pyrano[3,2-d]thiazole-5-carboxamide

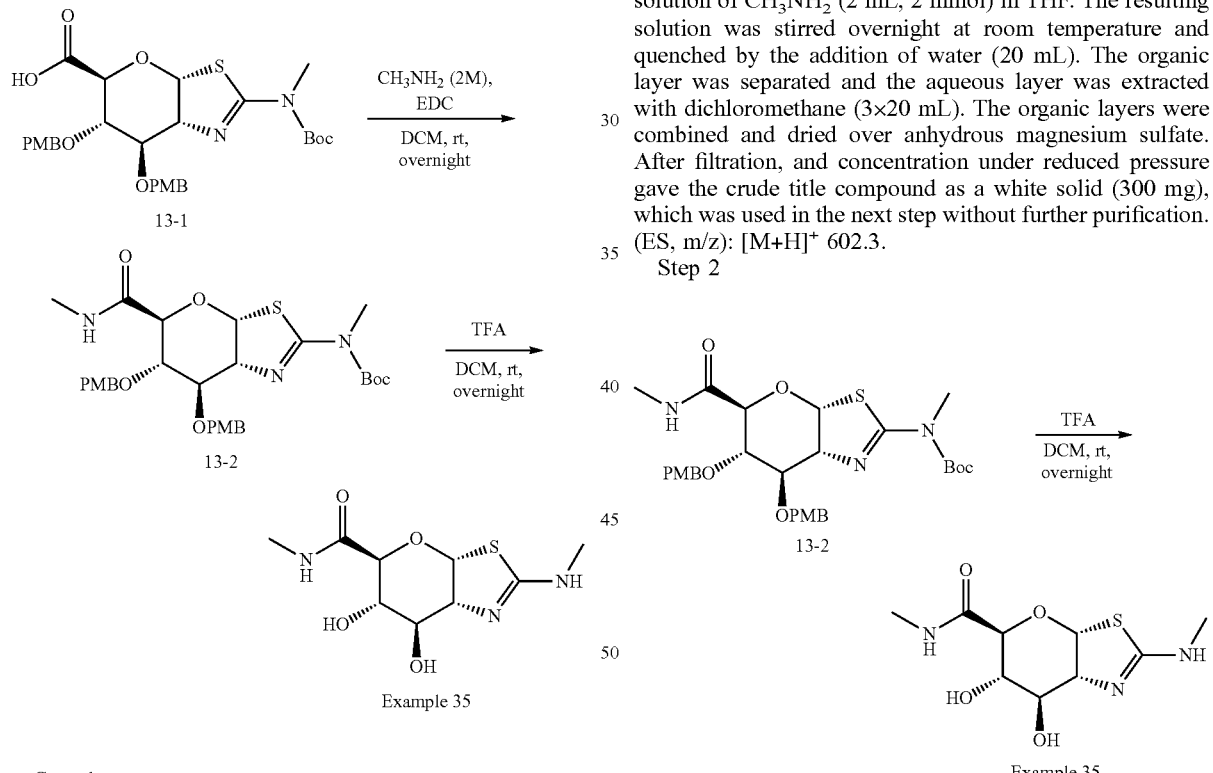

Step 1 tert-butyl (3aR,5S,6S,7R,7aR)-6,7-bis(4-methoxybenzyloxy)-5-(methylcarbamoyl)-5,6,7,7a-tetrahydro-3aH-pyrano[3,2-d]thiazol-2-yl(methyl)carbamate (13-2)

A solution of (3aR,5S,6S,7R,7aR)-6,7-bis(4-methoxybenzyloxy)-2-(tert-butoxycarbonyl)-5,6,7,7a-tetrahydro-3aH-pyrano[3,2-d]thiazole-5-carboxylic acid (400 mg, 0.68 mmol) (Prepared according to PCT publication WO2012061972 (A1), page 52, Step 7) in dichloromethane (12 mL) was treated with EDC (262 mg, 1.36 mmol) for 30 min at room temperature followed by the addition of 2 M solution of $CH_3NH_2$ (2 mL, 2 mmol) in THF. The resulting solution was stirred overnight at room temperature and quenched by the addition of water (20 mL). The organic layer was separated and the aqueous layer was extracted with dichloromethane (3×20 mL). The organic layers were combined and dried over anhydrous magnesium sulfate. After filtration, and concentration under reduced pressure gave the crude title compound as a white solid (300 mg), which was used in the next step without further purification. (ES, m/z): $[M+H]^+$ 602.3.

Step 2

(3aR,5S,6S,7R,7aR)-6,7-dihydroxy-N-methyl-2-(methylamino)-5,6,7,7a-tetrahydro-3aH-pyrano[3,2-d]thiazole-5-carboxamide A solution of the above crude tert-butyl (3aR,5S,6S,7R,7aR)-6,7-bis(4-methoxybenzyloxy)-5-(methylcarbamoyl)-5,6,7,7a-tetrahydro-3aH-pyrano[3,2-d]thiazol-2-yl(methyl)carbamate (300 mg) in dichloromethane (10 mL) was treated with trifluoroacetic acid (1 mL) overnight at room temperature. Upon evaporation of the volatiles, the residue was dissolved into methanol (5 mL) and neutralized with concentrated aqueous ammonia (1 mL). After concentrated under reduced pressure, the crude product was purified by Prep-HPLC with the following conditions [(Agilent 1200 detect prep HPLC): Column (Sun Fire Prep C18), 19*150 mm, 5 um; mobile phase, water with 0.05% ammonia and CH$_3$CN (10% CH$_3$CN up to 45% in 10 min); Detector, UV220 nm] to give the title compound as a white solid (40 mg, 22%, 2 steps). (ES, m/z) [M+H]$^+$ 262.1; $^1$H NMR (300 MHz, D$_2$O) δ 6.17 (d, J=6.3 Hz, 1H), 4.13-4.09 (m, 1H), 3.96-3.92 (m, 2H), 3.73 (dd, J=5.1 Hz, 8.7 Hz, 1H), 2.72 (s, 3H), 2.64 (s, 3H).

Example 36

(3aR,5S,6S,7R,7aR)-6,7-dihydroxy-2-(methylamino)-5,6,7,7a-tetrahydro-3aH-pyrano[3,2-d]thiazole-5-carboxylic acid

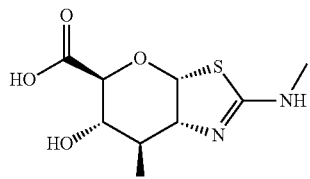

Example 36 nol (2 mL) and neutralized with concentrated aqueous ammonia (0.2 mL). After concentrated under reduced pressure, the crude product was purified by Prep-HPLC with the following conditions [(Agilent 1200 detect prep HPLC): Column (Sun Fire Prep C18), 19*150 mm; mobile phase, water with 0.03% NH$_3$.H$_2$O and CH$_3$CN (10% CH$_3$CN up to 45% in 10 min); Detector 220 nm.] to give the title compound as a light yellow solid (14.5 mg, 34%). (ES, m/z) [M+H]$^+$249.0; $^1$H NMR (300 MHz, D$_2$O) δ 6.36 (d, J=5.7 Hz, 1H), 4.24-4.12 (m, 2H), 4.08-3.97 (m, 1H), 3.91-3.87 (m, 1H), 2.92 (s, 3H).

Example 37

(3aR,5S,6S,7R,7aR)-methyl 6,7-dihydroxy-2-(methylamino)-5,6,7,7a-tetrahydro-3aH-pyrano[3,2-d]-thiazole-5-carboxylate

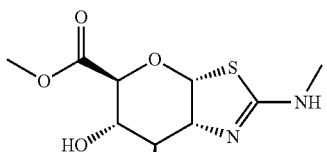

Example 37

Scheme 14

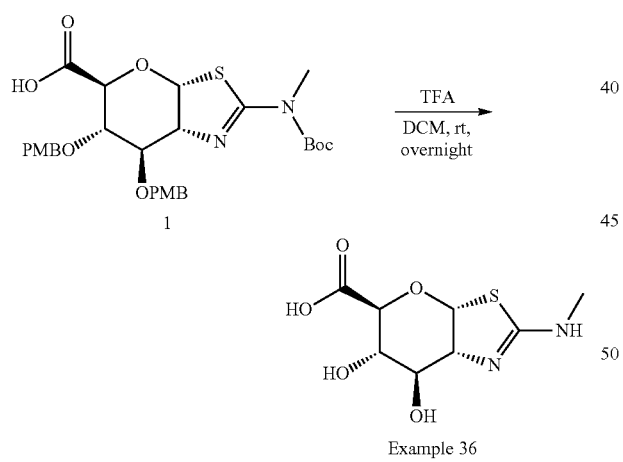

(3aR,5 S,6S,7R,7aR)-6,7-dihydroxy-2-(methylamino)-5,6,7,7a-tetrahydro-3aH-pyrano[3,2-d]thiazole-5-carboxylic acid A solution of (3aR,5S,6S,7R,7aR)-6,7-bis(4-methoxybenzyloxy)-2-(tert-butoxycarbonyl)-5,6,7,7a-tetrahydropyrano[3,2-d]thiazole-5-carboxylic acid (100 mg, 0.17 mmol) in dichloromethane (5 mL) was treated with trifluoroacetic acid (0.5 mL) overnight at room temperature. Upon evaporation of the volatiles, the residue was dissolved into metha- Scheme 15

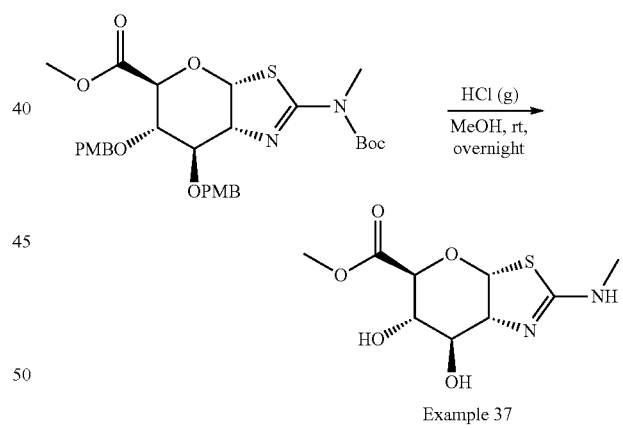

(3aR,5 S,6S,7R,7aR)-methyl 6,7-dihydroxy-2-(methylamino)-5,6,7,7a-tetrahydro-3aH-pyrano[3,2-d]thiazole-5-carboxylate A solution of (3aR,5S,6S,7R,7aR)-methyl 2-(tert-butoxycarbonyl(methyl)amino)-6,7-bis(4-methoxybenzyloxy)-5,6,7,7a-tetrahydro-3aH-pyrano[3,2-d]thiazole-5-carboxylate (200 mg, 0.34 mmol) (Prepared according to PCT publication WO2012061972 (A1), page 52, Step 8) in methanol (5 mL, saturated with HCl gas) was kept overnight at room temperature. Upon evaporation of the volatiles, the residue was dissolved in methanol (2 mL) and neutralized with concentrated aqueous ammonia (0.2 mL). After concentrated under reduced pressure, the crude product was purified by Prep-HPLC with the following conditions [(Agilent 1200 detect prep HPLC): Column (Sun Fire Prep C18), 19*150 mm; mobile phase, water with 0.03% NH$_3$.H$_2$O and CH$_3$CN (8% CH$_3$CN up to 45% in 10 min); Detector 220 nm.] to give the title compound as a white solid (46.8 mg, 53%). (ES, m/z) [M+H]$^+$ 262.9; $^1$H NMR (300 MHz, D$_2$O) δ 6.33 (d, J=5.1 Hz, 1H), 4.36-4.34 (m, 1H), 4.21-4.18 (m, 2H), 4.15-4.10 (m, 1H), 3.70 (s, 3H), 2.94 (s, 3H).

Example 38

1-((3aR,6S,7R,7aR)-6,7-dihydroxy-2-(methylamino)-5,6,7,7a-tetrahydro-3aH-pyrano[3,2-d]thiazol-5-yl)ethanone

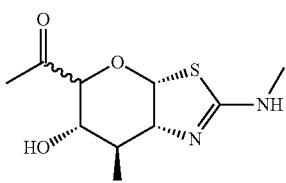

Example 38

Scheme 16

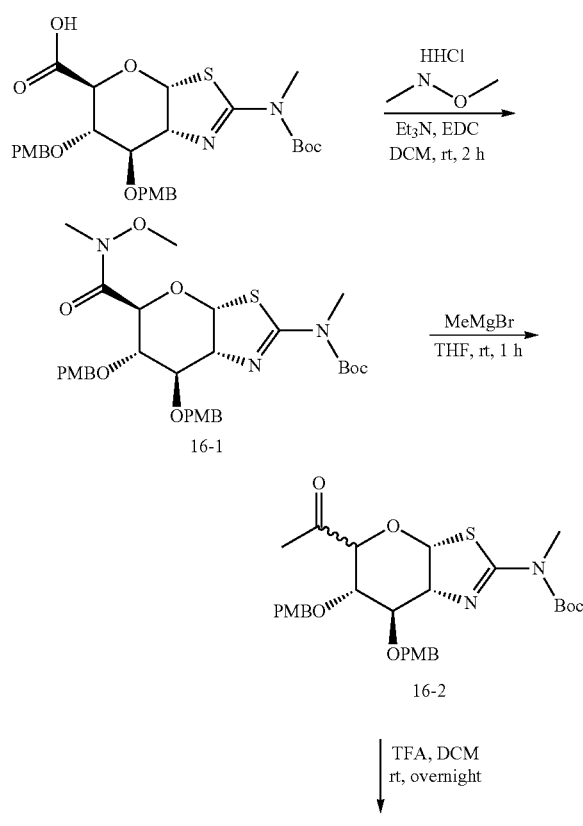

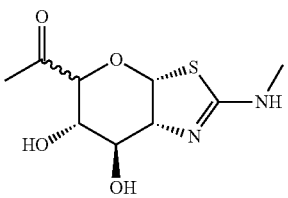

Example 38

Step 1

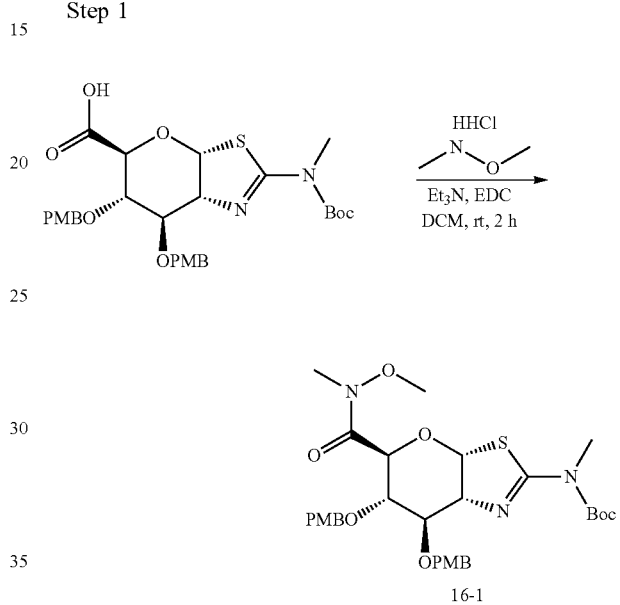

16-1 tert-butyl (3aR,5S,6S,7R,7aR)-5-(methoxy(methyl)carbamoyl)-6,7-bis(4-methoxybenzyloxy)-5,6,7,7a-tetrahydro-3aH-pyrano[3,2-d]thiazol-2-yl(methyl)carbamate (16-11)

A solution of (3aR,5S,6S,7R,7aR)-6,7-bis(4-methoxybenzyloxy)-2-(tert-butoxycarbonyl)-5,6,7,7a-tetrahydro-3aH-pyrano[3,2-d]thiazole-5-carboxylic acid (600 mg, 1 mmol) (Prepared according to PCT publication WO2012061972 (A1), page 52, Step 7), N-methoxymethanamine hydrochloride (198 mg, 2 mmol) and triethylamine (0.7 mL) in dichloromethane (30 mL) was treated with EDC (392 mg, 2 mmol) for 2 hours at room temperature. Then the reaction was quenched by brine (30 mL) and the aqueous layer was extracted with dichloromethane (3×30 mL). The combined organic layer was dried over anhydrous magnesium sulfate. After filtration and concentration under reduced pressure, the residue was purified by a silica gel column, eluted with 10%-20% ethyl acetate in petroleum ether to give the title compound as a white solid (550 mg, 85%). (ES, m/z): [M+H]$^+$ 632.1; $^1$H NMR (300 MHz, CDCl$_3$) δ 7.29-7.21 (m, 4H), 6.91-6.83 (m, 4H), 6.08 (d, J=5.7 Hz, 1H), 4.61-4.48 (m, 4H), 4.31-4.30 (m, 1H), 4.29-4.22 (m, 2H), 4.19-4.17 (t, J=4.8 Hz, 1H), 3.82 (s, 6H), 3.71 (s, 3H), 3.67 (s, 3H), 3.30 (s, 3H), 1.54 (s, 9H).

Step 2

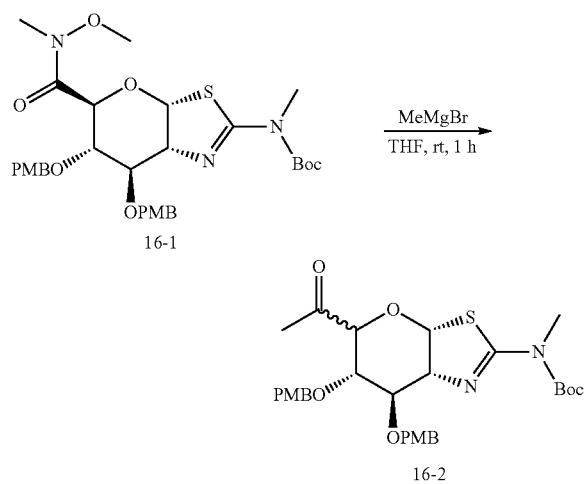

tert-butyl (3aR,6S,7R,7aR)-6,7-bis(4-methoxybenzyloxy)-5-acetyl-5,6,7,7a-tetrahydro-3aH-pyrano[3,2-d]thiazol-2-yl(methyl)carbamate (16-2)

A solution of tert-butyl (3aR,5S,6S,7R,7aR)-5-(methoxy(methyl)carbamoyl)-6,7-bis(4-methoxybenzyloxy)-5,6,7,7a-tetrahydro-3aH-pyrano[3,2-d]thiazol-2-yl(methyl)carbamate (631 mg, 1 mmol) in THF (10 mL) was treated with 2 M solution of methylmagnesium bromide (0.6 mL, 1.2 mmol) in THF for 1 hour at room temperature. Then the reaction was quenched by saturated aqueous NH$_4$Cl solution (20 mL) and extracted with ethyl acetate (3×20 mL). The combined organic layer was washed with brine (2×20 mL) and dried over anhydrous magnesium sulfate. After filtration and concentration under reduced pressure gave the product as light yellow syrup (410 mg, 70%). (ES, m/z): [M+H]$^+$ 587.0; $^1$H NMR (300 MHz, CDCl$_3$) δ 7.31-7.23 (m, 4H), 6.94-6.87 (m, 4H), 6.21 (d, J=6.6 Hz, 1H), 4.63-4.51 (m, 4H), 4.33-4.31 (m, 1H), 4.28-4.23 (m, 2H), 4.21-4.18 (m, 1H), 3.84 (s, 6H), 3.30 (s, 3H), 2.45 (s, 3H), 1.54 (s, 9H)

Step 3

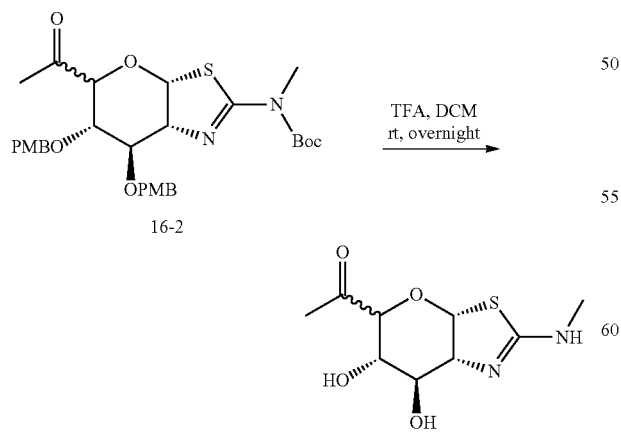

Example 38

1-((3aR,6S,7R,7aR)-6,7-dihydroxy-2-(methylamino)-5,6,7,7a-tetrahydro-3aH-pyrano[3,2-d]thiazol-5-yl)ethanone A solution of tert-butyl (3aR,6S,7R,7aR)-6,7-bis(4-methoxybenzyloxy)-5-acetyl-5,6,7,7a-tetrahydro-3aH-pyrano[3,2-d]thiazol-2-yl(methyl)carbamate (100 mg, 0.17 mmol) in dichloromethane (2 mL) was treated with trifluoroacetic acid (0.2 mL) overnight at room temperature. Upon evaporation of the volatiles, the residue was dissolved into methanol (2 mL) and neutralized with concentrated aqueous ammonia (0.2 mL). After concentrated under reduced pressure, the crude product was purified by Prep-HPLC with the following conditions [(Agilent 1200 detect prep HPLC): Column (Sun Fire Prep C18), 19*150 mm; mobile phase, water with 0.03% NH$_3$H$_2$O and CH$_3$CN (10% CH$_3$CN up to 45% in 12 min); Detector 220 nm.] to give the title compound as a off-white solid (11.3 mg, 27%). (ES, m/z): [M+H]$^+$ 247.1; $^1$H NMR (300 MHz, D$_2$O) δ 6.11 (d, J=5.4 Hz, 1H), 4.70-4.45 (m, 1H), 4.15-4.07 (m, 2H), 3.88-3.80 (m, 1H), 2.74 (s, 3H), 2.17 (s, 1.5H), 2.13 (s, 1.5H).

Example 39

(3aR,5S,6S,7R,7aR)-5-(chloromethyl)-2-(methylamino)-5,6,7,7a-tetrahydro-3aH-pyrano[3,2-d]thiazole-6,7-diol

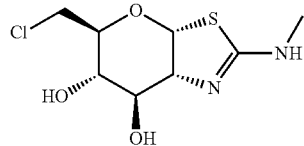

Example 39

Scheme 17

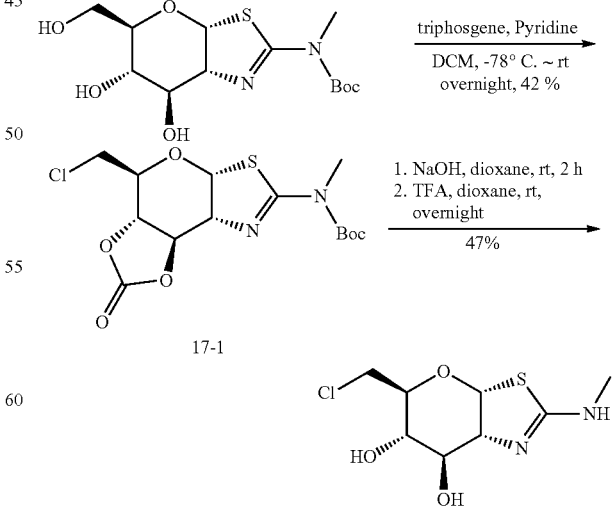

Example 39

Step 1

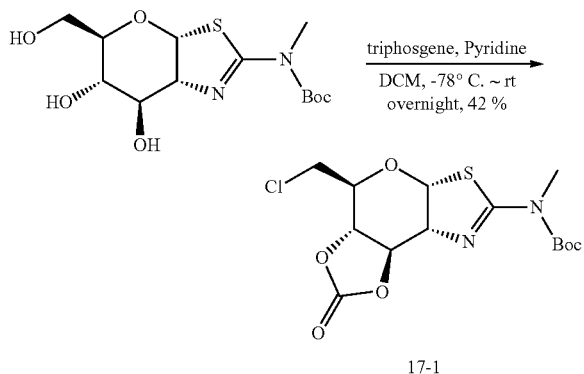

17-1 tert-butyl N-[(1R,2R,6R,8S,9S)-8-(chloromethyl)-11-oxo-7,10,12-trioxa-5-thia-3-azatricyclo[7.3.0.0-[2,6]] dodec-3-en-4-yl]-N-methylcarbamate (17-1)

Into a solution of tert-butyl N-[(3aR,5R,6S,7R,7aR)-6,7-dihydroxy-5-(hydroxymethyl)-3aH,5H,6H,7H,7aH-pyrano[3,2-d][1,3]thiazol-2-yl]-N-methylcarbamate (5 g, 14.95 mmol) and pyridine (7.1 g, 89.76 mmol) in dichloromethane (40 mL) was added a solution of triphosgene (4.4 g, 14.83 mmol) in dichloromethane (10 mL) at −78° C. The resulting solution was stirred overnight at room temperature and quenched by the addition of saturated aqueous solution of NaHCO$_3$ (30 mL). The organic layer was separated and the aqueous layer was extracted with dichloromethane (3×50 mL). The combined organic layers was dried over anhydrous magnesium sulfate. After filtration and concentration under reduced pressure, the residue was purified by a silica gel column, eluted with 10%-20% ethyl acetate in petroleum ether to give the title compound as a white solid (2.4 g, 42%). (ES, m/z): [M+H]$^+$ 379.0; $^1$H NMR (300 MHz, CDCl$_3$) δ 6.11 (d, J=5.4 Hz, 1H), 4.67-4.42 (m, 3H), 4.35-4.29 (m, 1H), 3.91-3.75 (m, 2H), 3.37 (s, 3H), 1.54 (s, 9H).

Step 2

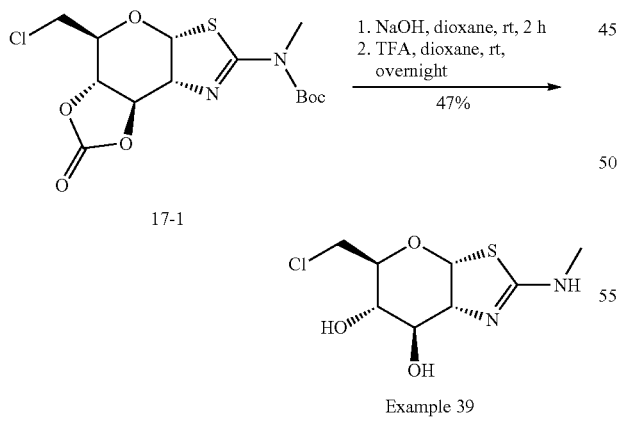

Example 39

(3aR,5S,6S,7R,7aR)-5-(chloromethyl)-2-(methylamino)-5,6,7,7a-tetrahydro-3aH-pyrano[3,2-d]thiazole-6,7-diol A solution of tert-butyl N-[(1R,2R,6R,8S,9S)-8-(chloromethyl)-1-oxo-7,10,12-trioxa-5-thia-3-azatricyclo[7.3.0.0 [2,6]]dodec-3-en-4-yl]-N-methylcarbamate (200 mg, 0.53 mmol,) in dioxane (10 mL) was treated with sodium hydroxide (42 mg, 1.05 mmol) at room temperature for 2 hours followed by the addition of trifluoroacetic acid (1 mL). The resulting solution was stirred for overnight at room temperature. Upon evaporation of the volatiles, the residue was dissolved into methanol (2 mL) and neutralized with concentrated aqueous ammonia (0.2 mL). After concentrated under reduced pressure, the crude product was purified by Prep-HPLC with the following conditions [(Agilent 1200 detect prep HPLC): Column (Sun Fire Prep C18), 19*150 mm; mobile phase, water with 0.03% NH$_3$H$_2$O and CH$_3$CN (15% CH$_3$CN up to 45% in 10 min); Detector 220 nm] to give the title compound as a white solid (62.6 mg, 47%). (ES, m/z): [M+H]$^+$ 253.0; $^1$H NMR (300 MHz, D$_2$O) δ 6.24 (d, J=4.5 Hz, 1H), 4.14 (t, J=4.2 Hz, 1H), 3.99 (t, J=4.2 Hz, 1H), 3.81-3.63 (m, 4H), 2.76 (s, 3H).

Example 40

(3aR,5R,6S,7R,7aR)-5-(2-aminoethyl)-2-(methylamino)-5,6,7,7a-tetrahydro-3aH-pyrano[3,2-d]thiazole-6,7-diol

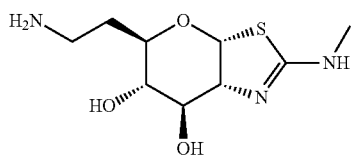

Example 40

Scheme 18

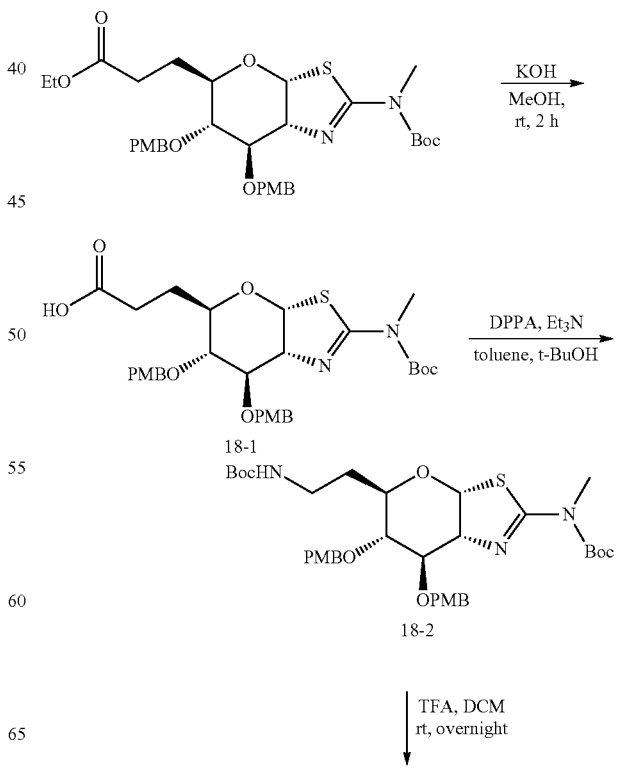

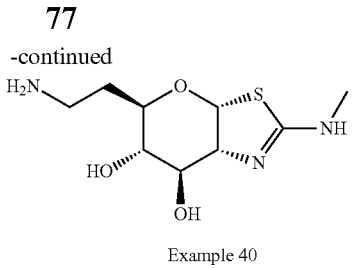

Example 40

Step 1

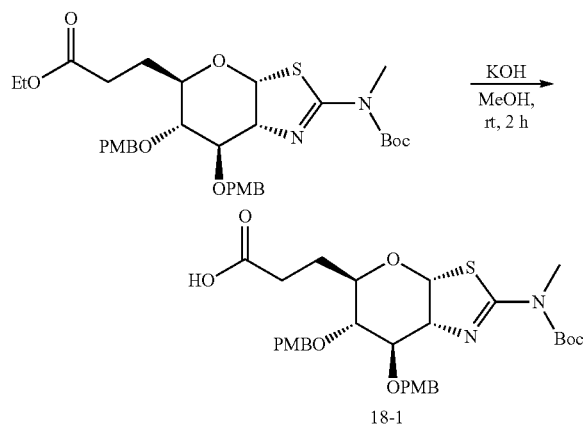

3-((3aR,5R,6R,7R,7aR)-6,7-bis(4-methoxybenzyloxy)-2-(tert-butoxycarbonyl)-5,6,7,7a-tetrahydro-3aH-pyrano[3,2-d]thiazol-5-yl)propanoic acid (18-1)

To a solution of ethyl 3-((3aR,5R,6R,7R,7aR)-6,7-bis(4-methoxybenzyloxy)-2-(tert-butoxycarbonyl)-5,6,7,7a-tetrahydro-3aH-pyrano[3,2-d]thiazol-5-yl)propanoate (740 mg, 1.15 mmol) (Prepared according to patent WO2012061972 (A1), page 103, Step 2) in methanol (30 mL) was added potassium hydroxide (129 mg, 2.30 mmol). The resulting solution was stirred for 2 hours at room temperature. After removal of methanol under reduced pressure, the residue was dissolved in water (30 mL). The pH value of the solution was adjusted to 3 with diluted hydrochloric acid and extracted with dichloromethane (4×30 mL). The organic layers were combined and dried over anhydrous magnesium sulfate. After filtration, the filtrate was concentrated under reduced pressure to give crude 1 as syrup (700 mg), which was used in the next step without further purification.

Step 2

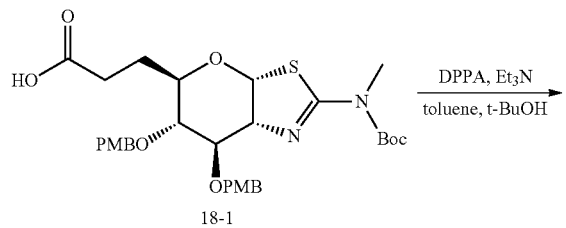

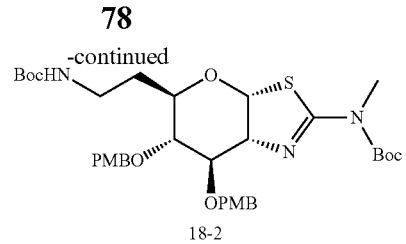

18-2

Boc protected tert-butyl (3aR,5R,6R,7R,7aR)-6,7-bis(4-methoxybenzyloxy)-5-(2-aminoethyl)-5,6,7,7a-tetrahydro-3aH-pyrano[3,2-d]thiazol-2-yl(methyl)carbamate (18-2)

To a solution of the above crude acid 1 (700 mg) in toluene (30 mL) was added triethylamine (0.7 mL, 4.15 mmol) and DPPA (625 mg, 2.27 mmol). The resulting solution was stirred for 2 hours at 30° C. followed by the addition of tert-Butanol (8 mL). After heated to reflux overnight the resulting solution was cooled to room temperature and quenched with water (50 mL), the organic layer was separated and the aqueous layer was extracted with dichloromethane (2×30 mL). The combined organic layer was dried over anhydrous magnesium sulfate. After filtration and concentration under reduced pressure, the residue was purified by a silica gel column, eluted with 20% ethyl acetate in petroleum to give the title compound as colorless syrup (400 mg, 51%, 2 steps). (ES, m/z): [M+H]$^+$ 688.0; $^1$H NMR (300 MHz, CDCls) δ 7.34 (d, J=8.4 Hz, 2H), 7.19 (d, J=8.5 Hz, 2H), 6.93-6.84 (m, 4H), 6.06 (d, J=6.9 Hz, 1H), 4.83 (brs, 1H), 4.70-4.63 (m, 2H), 4.59-4.40 (m, 2H), 4.27-4.23 (m, 2H), 3.82 (s, 3H), 3.81 (s, 3H), 3.42-3.14 (m, 7H), 1.91-1.80 (m, 2H), 1.54 (s, 9H), 1.43 (s, 9H).

Step 3

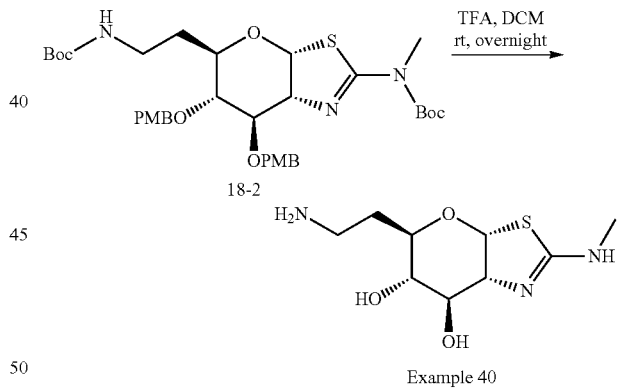

Example 40

(3aR,5R,6S,7R,7aR)-5-(2-aminoethyl)-2-(methylamino)-5,6,7,7a-tetrahydro-3aH-pyrano[3,2-d]thiazole-6,7-diol A solution of Boc protected tert-butyl (3aR,5R,6R,7R,7aR)-6,7-bis(4-methoxybenzyloxy)-5-(2-aminoethyl)-5,6,7,7a-tetrahydro-3aH-pyrano[3,2-d]thiazol-2-yl(methyl)carbamate (120 mg, 0.17 mmol) in dichloromethane (5 mL) was treated with trifluoroacetic acid (0.5 mL) for overnight at room temperature. Upon evaporation of the volatiles under reduced pressure, the residue was dissolved in methanol (3 mL) and neutralized with concentrated aqueous ammonia (0.3 mL). After concentrated under reduced pressure, the crude product was purified by Prep-HPLC with the following conditions [(Agilent 1200 detect prep HPLC):

Column (Sun Fire Prep C18), 19*150 mm; mobile phase, water with 0.03% NH$_3$H$_2$O and CH$_3$CN (10% CH$_3$CN up to 45% in 10 min); Detector 220 nm.] to give the title compound as a white solid (19.1 mg, 44%). (ES, m/z): [M+H]$^+$ 248.0; $^1$H NMR (300 MHz, D$_2$O) δ 6.16 (d, J=6.6 Hz, 1H), 4.12-4.10 (m, 1H), 3.95-3.92 (m, 1H), 3.57-3.50 (m, 1H), 3.43-3.40 (m, 1H), 3.01-2.96 (m, 2H), 2.71 (s, 3H), 2.10-1.99 (m, 1H), 1.81-1.71 (m, 1H).

Example 41

(3aR,5R,6S,7R,7aR)-2-(methylamino)-5-(2-(methylamino)ethyl)-5,6,7,7a-tetrahydro-3aH-pyrano[3,2-d]thiazole-6,7-diol

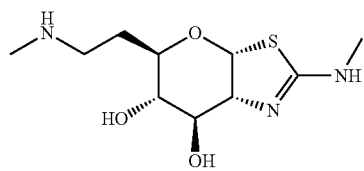

Example 41

Scheme 19

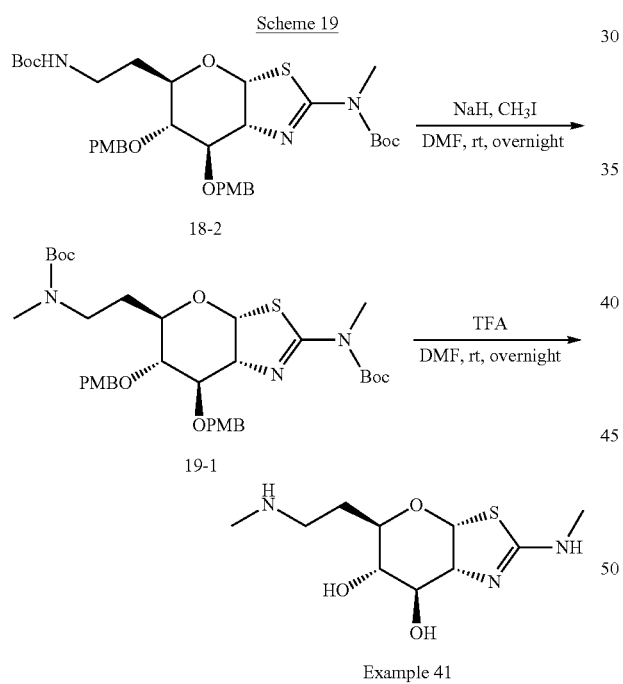

Step 1

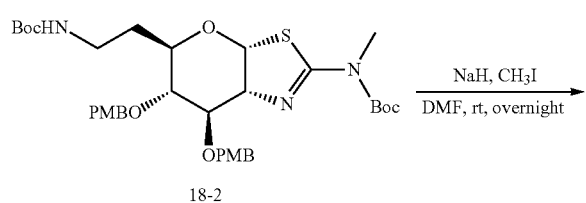

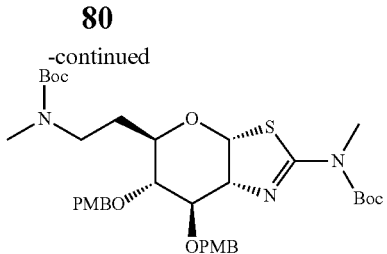

19-1

Boc protected tert-butyl (3aR,5R,6R,7R,7aR)-6,7-bis(4-methoxybenzyloxy)-5-(2-(methylamino)ethyl)-5,6,7,7a-tetrahydro-3aH-pyrano[3,2-d]thiazol-2-yl(methyl)carbamat (19-1)

A solution of Boc protected tert-butyl (3aR,5R,6R,7R,7aR)-6,7-bis(4-methoxybenzyloxy)-5-(2-aminoethyl)-5,6,7,7a-tetrahydro-3aH-pyrano[3,2-d]thiazol-2-yl(methyl)carbamate (200 mg, 0.29 mmol) in N,N-dimethylformamide (4 mL) was treated with sodium hydride (14 mg, 0.58 mmol) for 30 min at room temperature followed by the addition of iodomethane (1 mL). The resulting solution was stirred overnight at room temperature then quenched with water (20 mL) and extracted with ethyl acetate (3×20 ml). The combined organic layer was washed with brine (2×30 mL), dried over magnesium sulfate and concentrated under reduced pressure to give crude 3 as colorless syrup (140 mg), which was used in the next step without further purification.

Step 2

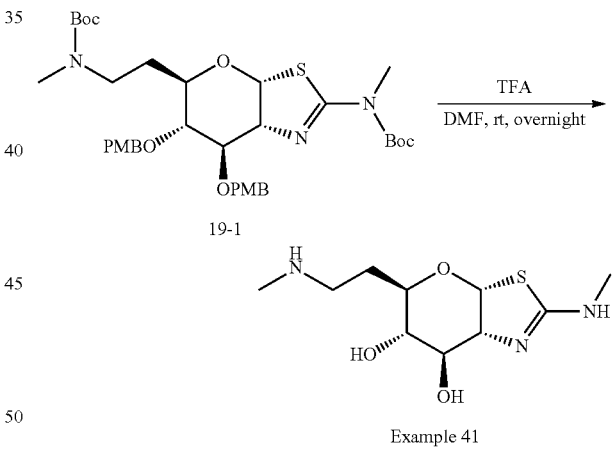

(3aR,5R,6S,7R,7aR)-2-(methylamino)-5-(2-(methylamino)ethyl)-5,6,7,7a-tetrahydro-3aH-pyrano[3,2-d]thiazole-6,7-diol A solution of the above crude Boc protected tert-butyl (3aR,5R,6R,7R,7aR)-6,7-bis(4-methoxybenzyloxy)-5-(2-(methylamino)ethyl)-5,6,7,7a-tetrahydro-3aH-pyrano[3,2-d]thiazol-2-yl(methyl)carbamate (140 mg) in dichloromethane (6 mL) was treated with trifluoroacetic acid (0.6 mL) for overnight at room temperature. Upon evaporation of the volatiles under reduced pressure, the residue was dissolved in methanol (3 mL) and neutralized with concentrated aqueous ammonia (0.3 mL). After concentrated under reduced pressure, the crude product was purified by Prep-HPLC with the following conditions [(Agilent 1200 detect prep HPLC): Column (Sun Fire Prep C18), 19*150 mm; mobile phase, water with 0.03% NH$_3$H$_2$O and CH$_3$CN (10% CH$_3$CN up to 45% in 12 min); Detector 220 nm] to give the title compound as a white solid (41.5 mg, 54%). (ES, m/z): [M+H]$^+$ 262.1; $^1$H NMR (300 MHz, D$_2$O) δ 6.15 (d, J=6.3 Hz, 1H), 4.09 (t, J=5.7 Hz, 1H), 3.93 (t, J=4.5 Hz, 1H), 3.54-3.37 (m, 2H), 2.96-2.85 (m, 2H), 2.70 (s, 3H), 2.49 (s, 3H), 2.07-1.97 (m, 1H), 1.81-1.71 (m, 1H).

TABLE 2

| Example | structure | Name | MH+ |
|---|---|---|---|
| 42 | 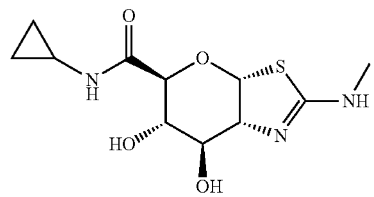 [SMILES: CNC1=N[C@@H]2[C@@H](O)[C@H](O)[C@@H](C(=O)NC3CC3)O[C@@H]2S1] | (3aR,5S,6S,7R,7aR)-N-cyclopropyl-6,7-dihydroxy-2-(methylamino)-5,6,7,7a-tetrahydro-3aH-pyrano[3,2-d]thiazole-5-carboxamide | 288.1 |
| 43 | 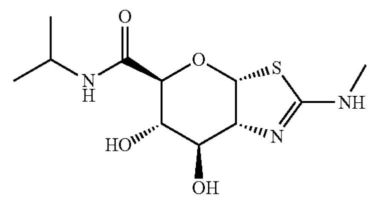 [SMILES: CNC1=N[C@@H]2[C@@H](O)[C@H](O)[C@@H](C(=O)NC(C)C)O[C@@H]2S1] | (3aR,5S,6S,7R,7aR)-6,7-dihydroxy-N-isopropyl-2-(methylamino)-5,6,7,7a-tetrahydro-3aH-pyrano[3,2-d]thiazole-5-carboxamide | 290.2 |
| 44 | 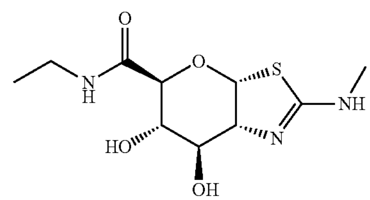 [SMILES: CCNC(=O)[C@H]1O[C@@H]2SC(NC)=N[C@@H]2[C@@H](O)[C@@H]1O] | (3aR,5S,6S,7R,7aR)-N-ethyl-6,7-dihydroxy-2-(methylamino)-5,6,7,7a-tetrahydro-3aH-pyrano[3,2-d]thiazole-5-carboxamide | 276.1 |
| 45 | 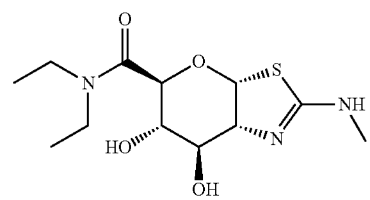 [SMILES: CCN(CC)C(=O)[C@H]1O[C@@H]2SC(NC)=N[C@@H]2[C@@H](O)[C@@H]1O] | (3aR,5S,6S,7R,7aR)-N,N-diethyl-6,7-dihydroxy-2-(methylamino)-5,6,7,7a-tetrahydro-3aH-pyrano[3,2-d]thiazole-5-carboxamide | 304.0 |
| 46 | 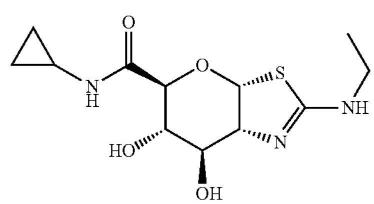 [SMILES: CCNC1=N[C@@H]2[C@@H](O)[C@H](O)[C@@H](C(=O)NC3CC3)O[C@@H]2S1] | (3aR,5S,6S,7R,7aR)-N-cyclopropyl-2-(ethylamino)-6,7-dihydroxy-5,6,7,7a-tetrahydro-3aH-pyrano[3,2-d]thiazole-5-carboxamide | 302.2 |
| 47 | 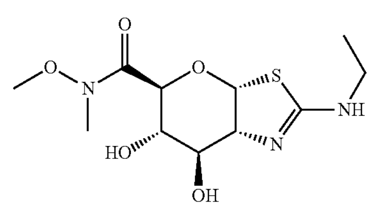 [SMILES: CCNC1=N[C@@H]2[C@@H](O)[C@H](O)[C@@H](C(=O)N(C)OC)O[C@@H]2S1] | (3aR,5S,6S,7R,7aR)-2-(ethylamino)-6,7-dihydroxy-N-methoxy-N-methyl-5,6,7,7a-tetrahydro-3aH-pyrano[3,2-d]thiazole-5-carboxamide | 306.2 |
| 48 | 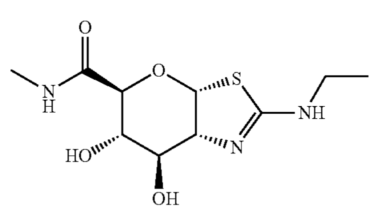 [SMILES: CCNC1=N[C@@H]2[C@@H](O)[C@H](O)[C@@H](C(=O)NC)O[C@@H]2S1] | (3aR,5S,6S,7R,7aR)-2-(ethylamino)-6,7-dihydroxy-N-methyl-5,6,7,7a-tetrahydro-3aH-pyrano[3,2-d]thiazole-5-carboxamide | 276.1 |

TABLE 2-continued

| Example | structure | Name | MH+ |
|---|---|---|---|
| 49 | 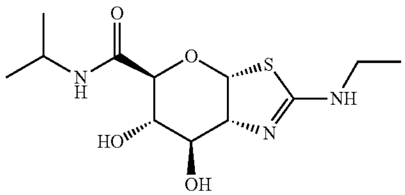 [SMILES: CCNC1=N[C@@H]2[C@@H](O)[C@H](O)[C@@H](C(=O)NC(C)C)O[C@@H]2S1] | (3aR,5S,6S,7R,7aR)-2-(ethylamino)-6,7-dihydroxy-N-isopropyl-5,6,7,7a-tetrahydro-3aH-pyrano[3,2-d]thiazole-5-carboxamide | 304.1 |
| 50 | 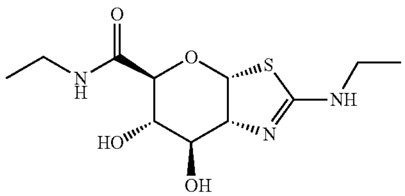 [SMILES: CCNC(=O)[C@H]1O[C@@H]2SC(NCC)=N[C@@H]2[C@@H](O)[C@@H]1O] | (3aR,5S,6S,7R,7aR)-N-ethyl-2-(ethylamino)-6,7-dihydroxy-5,6,7,7a-tetrahydro-3aH-pyrano[3,2-d]thiazole-5-carboxamide | 290.1 |
| 51 | 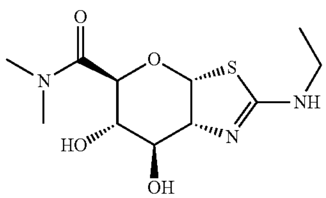 [SMILES: CCNC1=N[C@@H]2[C@@H](O)[C@H](O)[C@@H](C(=O)N(C)C)O[C@@H]2S1] | (3aR,5S,6S,7R,7aR)-2-(ethylamino)-6,7-dihydroxy-N,N-dimethyl-5,6,7,7a-tetrahydro-3aH-pyrano[3,2-d]thiazole-5-carboxamide | 290.1 |
| 52 | 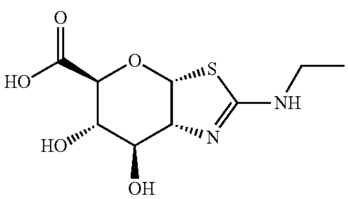 [SMILES: CCNC1=N[C@@H]2[C@@H](O)[C@H](O)[C@@H](C(=O)O)O[C@@H]2S1] | (3aR,5S,6S,7R,7aR)-2-(ethylamino)-6,7-dihydroxy-5,6,7,7a-tetrahydro-3aH-pyrano[3,2-d]thiazole-5-carboxylic acid | 263.0 |
| 53 | 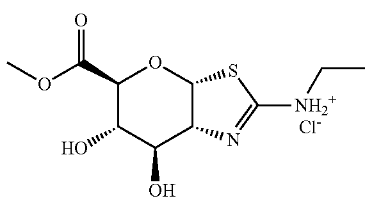 [SMILES: CC[NH2+]C1=N[C@@H]2[C@@H](O)[C@H](O)[C@@H](C(=O)OC)O[C@@H]2S1 ; [Cl-]] | (3aR,5S,6S,7R,7aR)-N-ethyl-6,7-dihydroxy-5-(methoxycarbonyl)-5,6,7,7a-tetrahydro-3aH-pyrano[3,2-d]thiazol-2-aminium chloride | 277.0 |
| 54 | 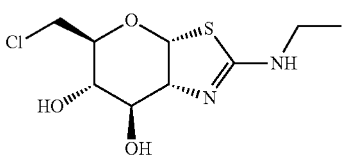 [SMILES: CCNC1=N[C@@H]2[C@@H](O)[C@H](O)[C@@H](CCl)O[C@@H]2S1] | (3aR,5S,6S,7R,7aR)-5-(chloromethyl)-2-(ethylamino)-5,6,7,7a-tetrahydro-3aH-pyrano[3,2-d]thiazole-6,7-diol | 267.0 |
| 55 | 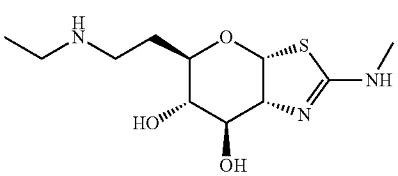 [SMILES: CCNCC[C@H]1O[C@@H]2SC(NC)=N[C@@H]2[C@@H](O)[C@@H]1O] | (3aR,5R,6S,7R,7aR)-5-(2-(ethylamino)ethyl)-2-(methylamino)-5,6,7,7a-tetrahydro-3aH-pyrano[3,2-d]thiazole-6,7-diol | 276.0 |
| 56 | 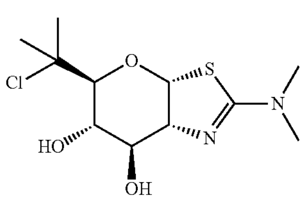 [SMILES: CN(C)C1=N[C@@H]2[C@@H](O)[C@H](O)[C@@H](C(C)(C)Cl)O[C@@H]2S1] | (3aR,5S,6S,7R,7aR)-5-(2-chloropropan-2-yl)-2-(dimethylamino)-5,6,7,7a-tetrahydro-3aH-pyrano[3,2-d]thiazole-6,7-diol | 295 |

Example 57

(3aR,5R,6S,7R,7aR)-2-(ethylamino)-5-ethynyl-5,6,7,7-tetrahydro-3aH-pyrano[3,2-d]thiazole-6,7-diol

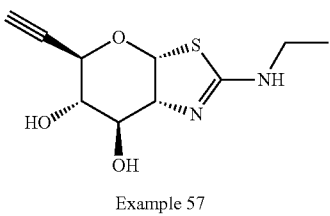 [SMILES: C#C[C@H]1O[C@@H]2SC(NCC)=N[C@@H]2[C@@H](O)[C@@H]1O]

Example 57

Scheme 20

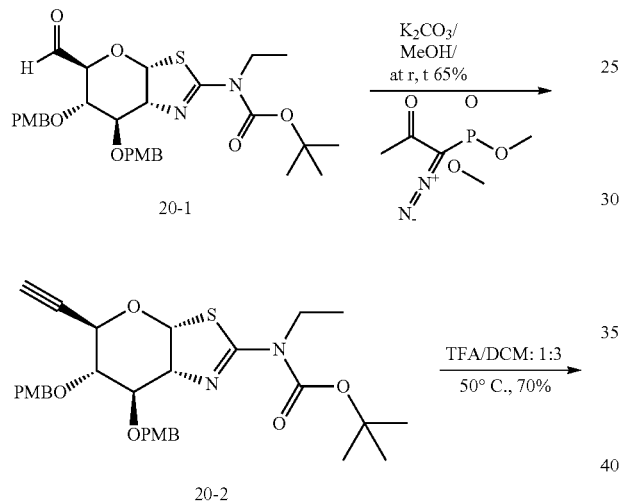

Example 57

To a solution of substrate 20-1 (548 mg, 0.935 mmol) and dimethyl(1-diazo-2-oxopropyl)phosphonate (269 mg, 1.4 mmol) in 4 mL dry methanol at 0° C. was added dry K₂CO₃ (258 mg, 1.85 mmol). N₂ gas was evolved immediately and the colour of the resulting suspension became light yellow. Ice bath was removed and the mixture was continued to stir at room temperature under Argon for 18 hours. After evaporation of the methanol, the residues was diluted with 100 mL ethyl acetate, and washed twice with 30 mL water, once with 50 mL brine and dried over MgSO₄. Evaporation solvent and flash chromatograph using 15% ethyl acetate and hexane gave compound 20-2 (324 mg, 60%) as colourless oil. Compound 2: (ES, m/z) [M-100 (BOC)+1]⁺483; ¹H NMR (400 MHz, CDCl₃) δ 7.24-7.30 (m, 4H), 6.84-6.89 (m, 4H), 5.90 (d, J=6.48 Hz, 1H), 4.64 (d, J=7.24 Hz, 2H), 4.59 (d, J=4.16 Hz, 2H), 4.25 (dd, J=4.60, 6.44 Hz, 1H), 4.20 (dd, J=2.16, 8.12 Hz, 1H), 4.07 (t, J=4.44 Hz, 1H), 3.85-3.93 (m, 2H), 3.81-3.84 (m, 1H), 3.83 (s, 3H), 3.82 (s, 3H), 2.47 (d, J=4.2 Hz, 1H), 1.55 (s, 9H), 1.12 (t, J=6.94 Hz, 3H);

To a solution of substrate 20-2 (304 mg, 0.522 mmol) in 3 mL DCM was added 1 mL of TFA at 0° C. The ice bath was removed and the resulting solution was continued to stir for 2 hours at room temperature then 1 hour at 40° C. Evaporation solvent and flash chromatograph using 3:5:92 NH₃H₂O-MeOH-DCM gave the title compound (90 mg, 70%) as white powder. Compound 3: (ES, m/z) [M+1]+243; ¹H NMR (400 MHz, methanol-d₄) δ 6.15 (d, J=6.08 Hz, 1H), 4.24 (dd, J=2.2, 8.52 Hz, 1H), 4.07 (t, J=5.8 Hz, 1H), 3.92 (t, J=5.8 Hz, 1H), 3.68 (dd, J=5.72, 8.52 Hz, 1H), 3.25-3.67 (m, 2H), 2.93 (d, J=2.2 Hz, 1H), 1.18 (t, J=7.2 Hz, 3H); ¹³C NMR (100 MHz, methanol-d₄) δ 161.15, 87.50, 80.61, 75.32, 74.24, 74.01, 73.57, 65.88, 38.36, 13.42.

Example 58

(3aR,5R,6S,7R,7aR)-2-(ethylamino)-6,7-dihydroxy-5,6,7,7a-tetrahydro-3aH-pyrano[3,2-d]thiazole-5-carbonitrile

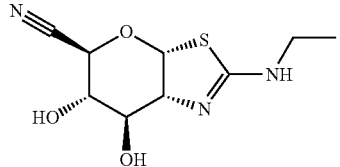

Example 58

Scheme 21

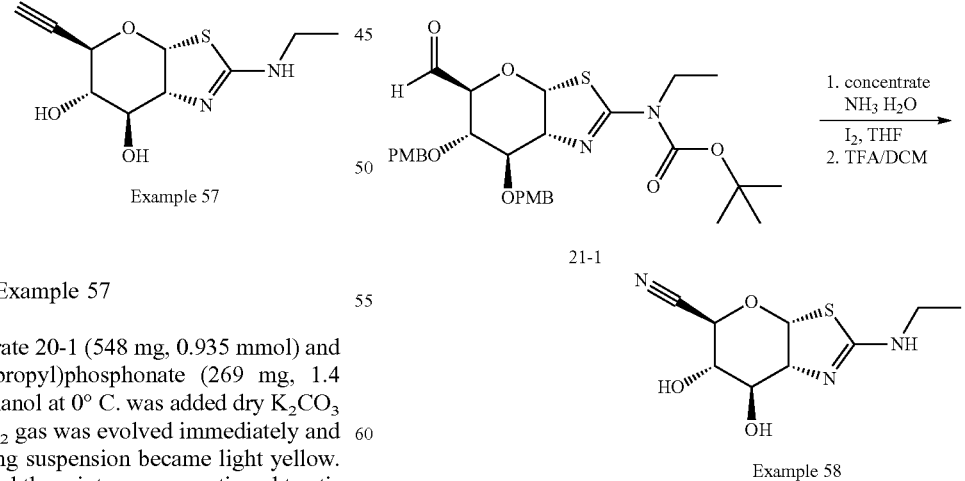

Example 58

To a solution of substrate 21-1 (275 mg, 0.45 mmol) was added mixture of concentrated ammonia (5 mL) solution and THF (2 mL). At room temperature, I₂ (57 mg, 0.45 mmol) was added and brownish solution was obtained. After 3 h, saturated Na₂S₂O₃ solution was added and this aqueous was extracted with 3 time 20 mL ethyl acetate. The combined organic solution was washed twice with 30 mL water, once with 50 mL brine and dried over MgSO₄. Evaporation solvent and flash chromatograph gave the crude compound.

To a solution of the crude material from above in 2 mL DCM was added 1.5 mL of TFA at 0° C. The ice bath was removed and the resulting solution was continued to stir for 2 hours at room temperature. Evaporation solvent and flash chromatograph using 3:5:92 NH₃H₂O-MeOH-DCM gave the title compound (21 mg) as white powder. (ES, m/z) [M+1]⁺ 244.1; ¹H NMR (400 MHz, methanol-d₄) δ 6.10 (d, J=7.8 Hz, 1H), 4.43 (d, J=7.8 Hz, 1H), 4.11 (t, J=5.24 Hz, 1H), 4.04 (t, J=5.12 Hz, 1H), 3.88 (dd, J=5.72, 7.8 Hz, 1H), 3.67-3.27 (m, 2H), 1.18 (t, J=7.24 Hz, 3H); ¹³C NMR (100 MHz, methanol-d₄) δ 160.88, 116.99, 86.82, 75.40, 71.98, 71.34, 64.59, 38.41, 13.35.

Example 59

(3aR,5 S,6S,7R,7aR)-2-(methylamino)-5-((phenylthio)methyl)-5,6,7,7a-tetrahydro-3aH-pyrano[3,2-d]thiazole-6,7-diol

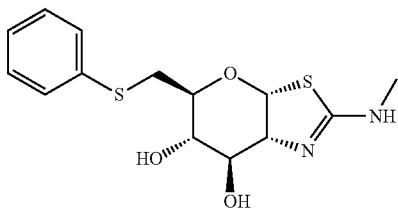

Example 59

Tert-butyl ((3aR,5R,5aS,7S,8S,9aR,9bR)-5-(hydroxymethyl)-7,8-dimethoxy-7,8-dimethyl-5,5a,7,8,9a,9b-hexahydro-3aH-[1,4]dioxino[2',3':4,5]pyrano[3,2-d]thiazol-2-yl) (methyl) carbamate

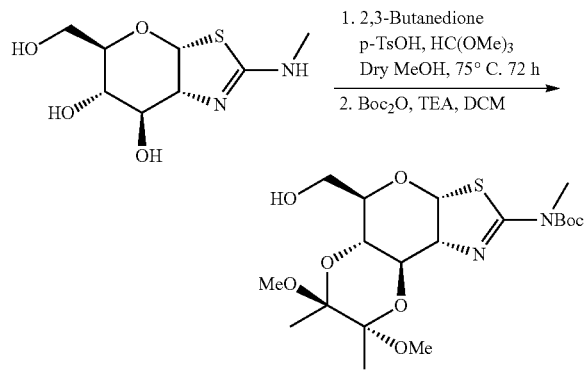

p-TsOH monohydrate (1.42 g, 7.5 mmol) was added to a stirred solution of (3aR,5R,6S,7R,7aR)-5-(hydroxymethyl)-2-(methylamino)-5,6,7,7a-tetrahydro-3aH-pyrano[3,2-d]thiazole-6,7-diol (1.17 g, 5 mmol), 2, 3-butanedione (4.37 mL, 50 mmol) and trimethyl orthoformate (3.7 mL, 34 mmol) in anhydrous methanol (20 mL). The mixture was heated at 75° C. for 72 h followed by the addition of triethylamine (1 mL) at RT. The contents were completely evaporated and mixture was re-dissolved in DCM (20 mL). Triethylamine (1.4 mL, 10 mmol) and Boc anhydride (1.63 g, 7.5 mmol) was added and mixture stirred overnight at RT. Washed with brine (30 mL) and dried over anhydrous sodium sulphate, organics were concentrated and purified on silica gel by automatic flash column chromatography (EtOAc/hexanes, 1:9), affording tert-butyl ((3aR,5R,5aS,7S,8S,9aR,9bR)-5-(hydroxymethyl)-7,8-dimethoxy-7,8-dimethyl-5,5a,7,8,9a,9b-hexahydro-3aH-[1,4]dioxino[2',3':4,5]pyrano[3,2-d]thiazol-2-ylmethyl)carbamate as crystalline white solid (0.89 g, 40%). ¹H NMR (500 MHz, CDCl₃) δ 6.11 (d, J=6.5 Hz, 1H), 4.09 (dd, J=8.5, 7.0 Hz, 1H), 3.96 (dt, J=9.5, 4.0 Hz, 1H), 3.87-3.75 (m, 4H), 3.29 (s, 3H), 3.26 (s, 3H), 3.23 (s, 3H), 1.97 (bs, 1H), 1.5 (s, 9H), 1.32 (s, 3H), 1.27 (s, 3H).

tert-butyl ((3aR,5S,5aS,7S,8S,9aR,9bR)-7,8-dimethoxy-7,8-dimethyl-5-((phenylthio)methyl)-5,5a,7,8,9a,9b-hexahydro-3aH-[1,4]dioxino[2',3':4,5]pyrano[3,2-d]thiazol-2-yl)methyl) carbamate

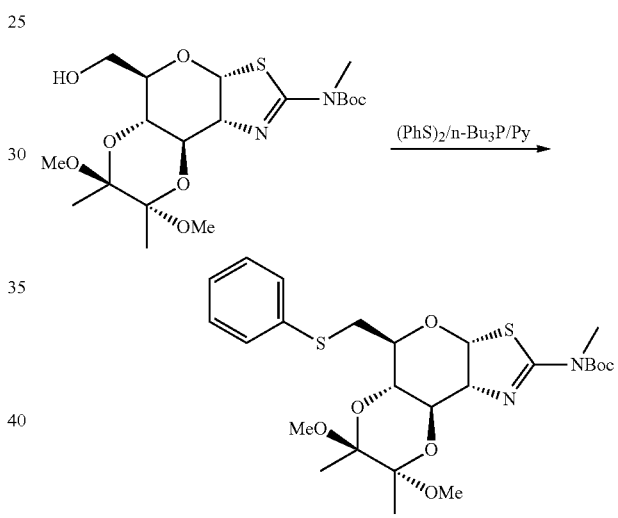

To a stirred solution of tert-butyl ((3aR,5R,5aS,7S,8S,9aR,9bR)-5-(hydroxymethyl)-7,8-dimethoxy-7,8-dimethyl-5,5a,7,8,9a,9b-hexahydro-3aH-[1,4]dioxino[2',3':4,5]pyrano[3,2-d]thiazo-2-yl)methyl)carbamate (0.236 g, 0.52 mmol) in dry pyridine (10 mL) was added diphenyl disulfide (0.23 g, 1.05 mmol) followed by n-tributylphosphine (0.26 mL, 1.05 mmol). After stirring at RT overnight, the mixture was diluted with EtOAc (50 mL) and organics were washed with brine (50 mL), dried over anhydrous sodium sulfate and concentrated. Co-evaporation with hexanes removed the residual pyridine. The crude residue was purified on silica gel by automatic flash column chromatography (EtOAc/hexanes, 3:7), affording tert-butyl ((3aR,5S,5aS,7S,8S,9aR,9bR)-7,8-dimethoxy-7,8-dimethyl-5-((phenylthio)methyl)-5,5a,7,8,9a, 9b-hexahydro-3aH-[1,4]dioxino[2',3':4,5]pyrano[3,2-d]thiazol-2-yl)methyl) carbamate as a white solid (0.195 g, 69.3%). ¹H NMR (500 MHz, CDCl₃) δ 7.39-7.16 (m, 5H), 6.07 (d, J=6.5 Hz, 1H), 4.19-4.10 (m, 1H), 3.86-3.77 (m, 2H), 3.38 (d, J=13.5, 3.0 Hz, 1H), 3.32 (s, 3H), 3.27 (s, 3H), 3.24 (s, 3H), 3.13 (dd, J=13.5, 6.5 Hz, 1H), 1.5 (s, 9H), 1.33 (s, 3H), 1.27 (s, 3H).

(3aR,5S,6S,7R,7aR)-2-(methylamino)-5-((phenyl-thio) methyl)-5,6,7,7a-tetrahydro-3aH-pyrano[3,2-d]thiazole-6,7-diol tert-butyl ((3aR,5S,5aS,7S,8S,9aR,9bR)-7,8-dimethoxy-7,8-dimethyl-5-((phenylsulfonyl) methyl)-5,5a,7,8,9a,9b-hexahydro-3aH-[1,4]dioxino[2',3':4,5]pyrano[3,2-d]thiazol-2-yl)methyl)carbamate

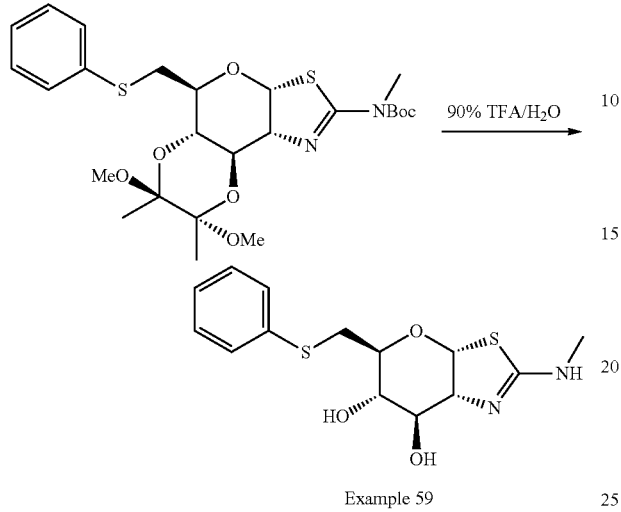

Example 59

At 0° C., to tert-butyl ((3aR,5S,5aS,7S,8S,9aR,9bR)-7,8-dimethoxy-7,8-dimethyl-5-((phenylthio) methyl)-5,5a,7,8,9a, 9b-hexahydro-3aH-[1,4]dioxino[2',3':4,5]pyrano[3,2-d]thiazol-2-yl)methyl) carbamate (0.072 g, 0.134 mmol) was added a solution of 90% TFA/H$_2$O (10 mL) and stirred at this temperature for 10 mins. Ice-bath was removed and reaction stirred for 5 h at RT. The reaction mixture was evaporated to dryness. The residue was neutralized with 1.5 M NH$_3$/MeOH solution (10 mL) and concentrated. The crude residue was purified by silica gel column chromatography (DCM/MeOH, 9:1) to provide (3aR,5S,6S,7R,7aR)-2-(methylamino)-5-((phenylthio)methyl)-5,6,7,7a-tetrahydro-3aH-pyrano[3,2-d]thiazole-6,7-diol as a white solid (0.038 g, 86.8%). $^1$H NMR (400 MHz, CD$_3$OD) δ 7.42-7.17 (m, 5H), 6.40 (d, J=6.4 Hz, 1H), 4.11 (t, J=6.4 Hz, 1H), 3.88 (t, J=6.4 Hz, 1H), 3.75 (td, J=8.8, 2.4 Hz, 1H), 3.51 (dd, J=9.2, 6.0 Hz, 1H), 3.46 (dd, J=14.0, 2.4 Hz, 1H), 3.03 (dd, J=14.0, 8.8 Hz, 1H), 2.90 (s, 3H). $^{13}$C NMR (100 MHz, CD$_3$OD) δ 166.96, 138.59, 131.75, 130.81, 128.12, 90.89, 76.16, 74.53, 72.23, 55.64, 38.12, 31.87. MS, (ES, m/z) [M+H]$^+$ 327.1.

Example 60

(3aR,5S,6S,7R,7aR)-2-(methylamino)-5-((phenyl-sulfonyl)methyl)-5,6,7,7a-tetrahydro-3aH-pyrano[3,2-d]thiazole-6,7-diol

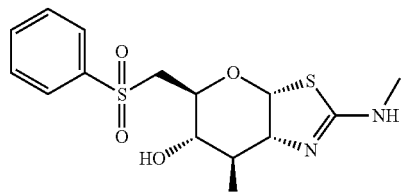

Example 60

To a solution of tert-butyl ((3aR,5S,5aS,7S,8S,9aR,9bR)-7,8-dimethoxy-7,8-dimethyl-5-((phenylthio)methyl)-5,5a,7,8,9a, 9b-hexahydro-3aH-[1,4]dioxino[2',3':4,5]pyrano[3,2-d]thiazol-2-yl)methyl) carbamate (0.102 g, 0.19 mmol) in THF: MeOH (1:4, 10 mL) was added aq. sodium acetate (0.31 g/0.6 mL H$_2$O, 3.8 mmol) and oxone (0.58 g, 0.95 mmol). The turbid reaction mixture was stirred at RT for 2.5 h and diluted with DCM (30 mL). DCM layer was washed with aq. sodium thiosulfate (1M, 30 mL), dried over anhydrous sodium sulfate. After filtration the solvent was evaporated under reduced pressure, and the residue was purified on silica gel by automatic flash column chromatography (EtOAc/hexanes, 1:1) affording tert-butyl ((3aR,5S,5aS,7S,8S,9aR,9bR)-7,8-dimethoxy-7,8-dimethyl-5-((phenylsulfonyl) methyl)-5,5a,7, 8,9a,9b-hexahydro-3aH-[1,4]dioxino[2',3':4,5]pyrano[3,2-d]thiazol-2-yl)methyl)carbamate as a white solid (0.057 g, 52.3%). $^1$H NMR (400 MHz, CDCl$_3$) δ 7.90-7.53 (m, 5H), 5.76 (d, J=6.8 Hz, 1H), 4.42 (td, J=10.0, 1.2 Hz, 1H), 3.98 (dd, J=8.8, 6.8 Hz, 1H), 3.72 (t, J=9.2 Hz, 1H), 3.63 (dd, J=14.8, 1.6 Hz, 1H), 3.40 (t, J=10.0 Hz, 1H), 3.32 (dd, J=10.0, 5.6 Hz, 1H), 3.26 (s, 3H), 3.20 (s, 3H), 3.18 (s, 3H), 1.54 (s, 9H), 1.29 (s, 3H), 1.25 (s, 3H). (3aR,5S,6S,7R,7aR)-2-(methylamino)-5-((phenylsulfonyl) methyl)-5,6,7,7a-tetrahydro-3aH-pyrano[3,2-d]thiazole-6,7-diol

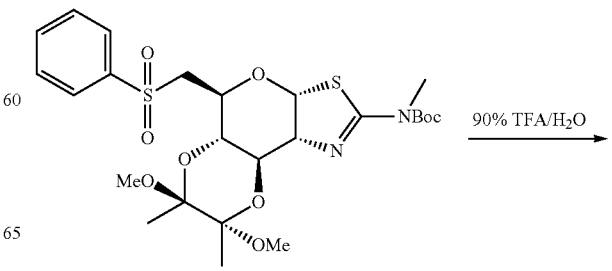

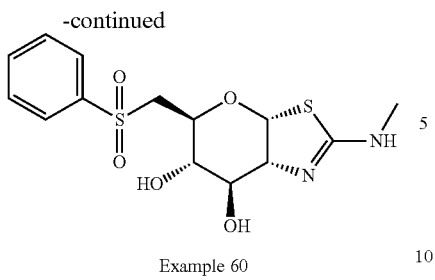

Example 60

At 0° C., to tert-butyl ((3aR,5S,5aS,7S,8S,9aR,9bR)-7,8-dimethoxy-7,8-dimethyl-5-((phenyl sulfonyl)methyl)-5,5a,7,8,9a,9b-hexahydro-3aH-[1,4]dioxino[2',3':4,5]pyrano[3,2-d]thiazol-2-yl)(methyl)carbamate (0.082 g, 0.14 mmol) was added a solution of 90% TFA/H$_2$O (10 mL) and stirred at this temperature for 10 mins. Ice-bath was removed and reaction stirred for 5 h at RT.

The reaction mixture was evaporated to dryness. The residue was neutralized with 1.5 M NH$_3$/MeOH solution (10 mL) and concentrated. The crude residue was purified by silica gel column chromatography (DCM/MeOH, 9:1) to provide (3aR,5S,6S,7R,7aR)-2-(methylamino)-5-((phenylsulfonyl)methyl)-5,6,7,7a-tetrahydro-3aH-pyrano[3,2-d]thiazole-6,7-diol as a white solid (0.045 g, 89.2%). $^1$H NMR (500 MHz, CD$_3$OD) δ 7.88-7.57 (m, 5H), 6.14 (d, J=6.5 Hz, 1H), 4.02 (t, J=9.0 Hz, 1H), 3.98 (t, J=6.5 Hz, 1H), 3.66 (dd, J=15.0, 1.0 Hz, 1H), 3.54 (dd, J=15.0, 9.0 Hz, 1H), 3.30 (m, 1H), 2.91 (s, 3H). $^{13}$C NMR (125 MHz, CD$_3$OD) δ 164.00, 142.05, 135.92, 131.25, 130.09, 89.59, 75.84, 73.06, 72.80, 59.61, 55.62, 33.86, 32.11. MS, (ES, m/z) [M+H]$^+$ 359.1.

Example 61

(3aR,5S,6S,7R,7aR)-5-((benzylthio)methyl)-2-(methylamino)-5,6,7,7a-tetrahydro-3aH-pyrano[3,2-d]thiazole-6,7-diol

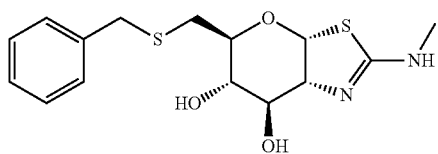

Example 61

((3aR,5R,5aS,7S,8S,9aR,9bR)-2-((tert-butoxycarbonyl)(methyl)amino)-7,8-dimethoxy-7,8-dimethyl-5,5a,7,8,9a,9b-hexahydro-3aH-[1,4]dioxino[2',3':4,5]pyrano[3,2-d]thiazol-5-yl)methyl 4-methylbenzenesulfonate

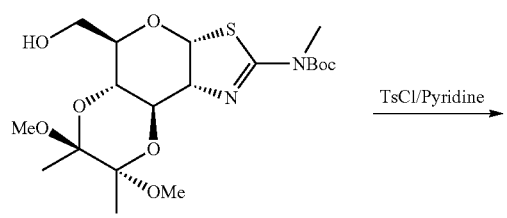

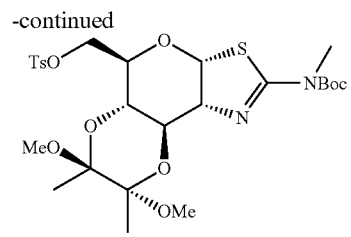

To a solution of tert-butyl ((3aR,5R,5aS,7S,8S,9aR,9bR)-5-(hydroxymethyl)-7,8-dimethoxy-7,8-dimethyl-5,5a,7,8,9a,9b-hexahydro-3aH-[1,4]dioxino[2',3':4,5]pyrano[3,2-d]thiazo-2-yl)methyl)carbamate (0.22 g, 0.50 mmol) in pyridine (8 mL) at 0° C. under N$_2$, was added toluenesulfonyl chloride (TsCl) (0.14 g, 0.75 mmol). After the addition, it was stirred at RT overnight. The mixture was then diluted with dichloromethane (50 mL), and washed with saturated aqueous NaHCO$_3$ (30 mL) and brine (30 mL). The organic layer was collected and dried over anhydrous Na$_2$SO$_4$. After filtration the solvent was evaporated under reduced pressure and the residue was purified on silica gel by automatic flash column chromatography (EtOAc/hexanes, 2:3) to yield ((3aR,5R,5aS,7S,8S,9aR,9bR)-2-((tert-butoxycarbonyl)(methyl) amino)-7,8-dimethoxy-7,8-dimethyl-5,5a,7,8,9a,9b-hexahydro-3aH [1,4] dioxino [2',3':4,5] pyrano[3,2-d] thiazol-5-yl)methyl 4-methylbenzenesulfonate as a crystalline white solid (0.137 g, 45.4%). $^1$H NMR (400 MHz, CDCl$_3$) δ 7.76 (d, J=8.4 Hz, 2H), 7.33 (d, J=8.0 Hz, 2H), 5.82 (d, J=6.4 Hz, 1H), 4.3 (dd, J=10.8, 3.6 Hz, 1H), 4.15 (dd, J=10.8, 2.0 Hz, 1H), 4.04 (dd, J=8.0, 6.4 Hz, 1H), 3.97-3.94 (m, 1H), 3.86 (t, J=10.8 Hz, 1H), 3.79 (dd, J=10.4, 8.0 Hz, 1H), 3.28 (s, 3H), 3.23 (s, 6H), 2.43 (s, 3H), 1.5 (s, 9H), 1.31 (s, 3H), 1.25 (s, 3H).

tert-butyl ((3aR,5S,5aS,7S,8S,9aR,9bR)-5-((benzylthio)methyl)-7,8-dimethoxy-7,8-dimethyl-5,5a,7,8,9a,9b-hexahydro-3aH-[1,4]dioxino[2',3':4,5]pyrano[3,2-d]thiazol-2-yl)methyl)carbamate

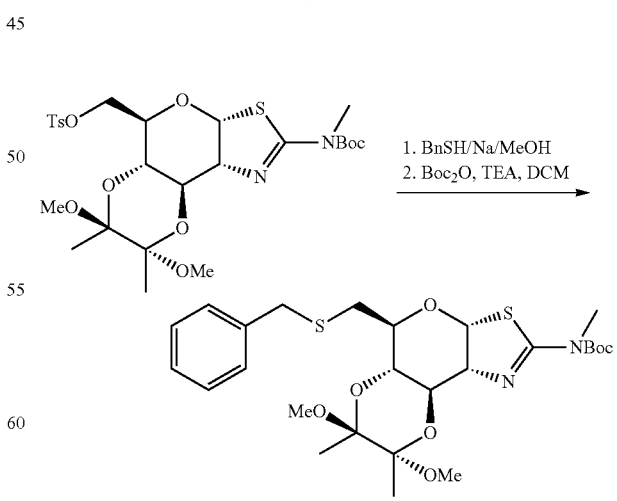

To a stirred solution of benzyl mercaptan (0.120 mL, 1.03 mmol) in anhydrous methanol at 0° C. under N$_2$ was added sodium metal (Na) (0.023 g, 1.03) slowly and contents were stirred at RT. After 1 h, ((3aR,5R,5aS,7S,8S,9aR,9bR)-2-((tert-butoxycarbonyl)(methyl)amino)-7,8-dimethoxy-7,8-dimethyl-5,5a,7,8,9a,9b-hexahydro-3aH-[1,4]dioxino[2',3':4,5]pyrano[3,2-d]thiazol-5-yl) methyl 4-methylbenzenesulfonate (0.15 g, 0.25 mmol) was added and reaction heated to reflux at 75° C. for 4 h. The mixture was then diluted with DCM (50 mL), washed with saturated aqueous NaHCO$_3$ (30 mL) and dried over anhydrous Na$_2$SO$_4$. After filtration the solvent was evaporated under reduced pressure and the crude residue was re-dissolved in DCM (8 mL). Boc anhydride (0.1 g, 0.5 mmol) and triethylamine (0.14 mL, 1 mmol) was added and mixture stirred at RT overnight. Solvent was evaporated under reduced pressure and the residue was purified on silica gel by automatic flash column chromatography (EtOAc/hexanes, 3:7) to yield tert-butyl ((3aR5S,5aS,7S,8S,9aR,9bR)-5-((benzylthio)methyl)-7,8-dimethoxy-7,8-dimethyl-5,5a,7,8,9a, 9b-hexahydro-3aH-[1,4]dioxino[2',3':4,5]pyrano[3,2-d]thiazol-2-yl)methyl)carbamate as a white solid (0.105 g, 75.6%). $^1$H NMR (400 MHz, CDCl$_3$) δ 7.35-7.24 (m, 5H), 6.12 (d, J=6.8 Hz, 1H), 4.19-4.14 (m, 1H), 4.13 (dd, J=8.4, 6.8 Hz, 1H), 3.88-3.72 (m, 4H), 3.33 (s, 3H), 3.26 (s, 3H), 3.24 (s, 3H), 2.81 (dd, J=14.4, 3.2 Hz, 1H), 2.67 (dd, J=14.4, 6.8 Hz, 1H), 1.55 (s, 9H), 1.34 (s, 3H), 1.28 (s, 3H).

(3aR,5S,6S,7R,7aR)-5-((benzylthio)methyl)-2-(methylamino)-5,6,7,7a-tetrahydro-3aH-pyrano[3,2-d]thiazole-6,7-diol

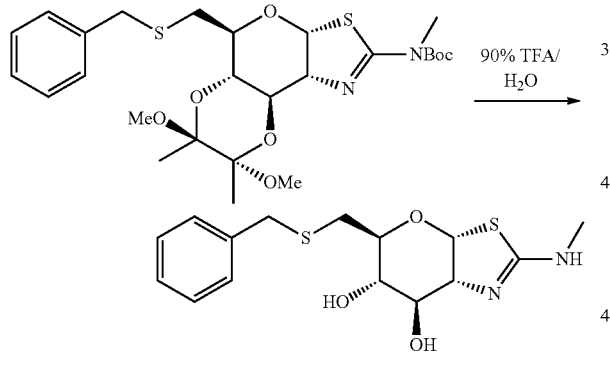

Example 61

At 0° C., to tert-butyl ((3aR,5S,5aS,7S,8S,9aR,9bR)-5-((benzylthio)methyl)-7,8-dimethoxy-7,8-dimethyl-5,5a,7,8,9a,9b-hexahydro-3aH-[1,4]dioxino[2',3':4,5]pyrano[3,2-d]thiazol-2-yl) (methyl)carbamate (0.094 g, 0.17 mmol) was added a solution of 90% TFA/H$_2$O (10 mL) and stirred at this temperature for 10 mins. Ice-bath was removed and reaction stirred for 5 h at RT. The reaction mixture was evaporated to dryness. The residue was neutralized with 1.5 M NH$_3$/MeOH solution (10 mL) and concentrated. The crude residue was purified by silica gel column chromatography (DCM/MeOH, 9:1) to provide (3aR,5S,6S,7R,7aR)-5-((benzylthio)methyl)-2-(methylamino)-5,6,7,7a-tetrahydro-3aH-pyrano[3,2-d]thiazole-6,7-diol as a white solid (0.051 g, 79.3%). $^1$H NMR (400 MHz, CD$_3$OD) δ 7.32-7.19 (m, 5H), 6.48 (d, J=6.4 Hz, 1H), 4.09 (t, J=6.4 Hz, 1H), 3.84 (t, J=6.4 Hz, 1H), 3.77 (s, 2H), 3.74 (m, 1H), 3.46 (dd, J=9.2, 6.4 Hz, 1H), 2.96 (s, 3H), 2.87 (dd, J=14.4, 2.4 Hz, 1H), 2.62 (dd, J=14.4, 8.0 Hz, 1H). $^{13}$C NMR (100 MHz, CD$_3$OD) δ 169.99, 140.88, 130.98, 130.25, 128.77, 90.50, 77.98, 75.85, 73.83, 69.77, 55.64, 38.72, 34.88, 32.15. MS, (ES, m/z) [M+H]$^+$ 341.1.

Example 62

(3aR,5S,6S,7R,7aR)-5-((benzylsulfonyl)methyl)-2-(methylamino)-5,6,7,7a-tetrahydro-3aH-pyrano[3,2-d]thiazole-6,7-diol

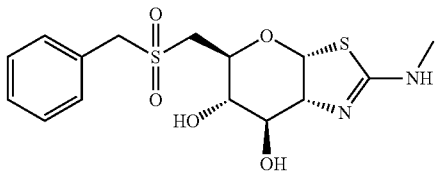

Example 62 tert-butyl((3aR,5 S,5aS,7S,8S,9aR,9bR)-5-((benzylsulfonyl)methyl)-7,8-dimethoxy-7,8-dimethyl-5,5a,7,8,9a,9b-hexahydro-3aH-[1,4]dioxino[2',3':4,5]pyrano[3,2-d]thiazol-2-yl)methyl)carbamate

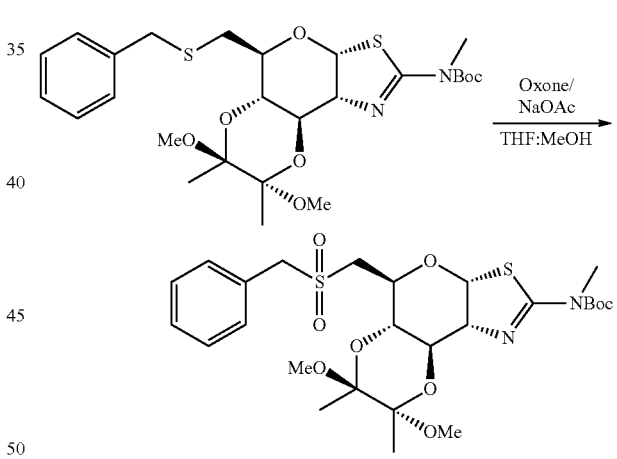

To a solution of tert-butyl ((3aR,5S,5aS,7S,8S,9aR,9bR)-5-((benzylthio)methyl)-7,8-dimethoxy-7,8-dimethyl-5,5a,7,8,9a,9b-hexahydro-3aH-[1,4]dioxino[2',3':4,5]pyrano[3,2-d]thiazol-2-yl) (methyl)carbamate (0.105 g, 0.19 mmol) in THF: MeOH (1:4, 10 mL) was added aq. sodium acetate (0.318/0.6 mL H$_2$O, 3.8 mmol) and oxone (0.58 g, 0.95 mmol). The turbid reaction mixture was stirred at RT for 2.5 h and diluted with DCM (30 mL). DCM layer was washed with aq. sodium thiosulfate (1M, 30 mL), dried over anhydrous sodium sulfate. After filtration the solvent was evaporated under reduced pressure, and the residue was purified on silica gel by automatic flash column chromatography (EtOAc/hexanes, 1:1) affording tert-butyl((3aR,5S,5aS,7S,8S,9aR,9bR)-5-((benzylsulfonyl)methyl)-7,8-dimethoxy-7,8-dimethyl-5,5a,7,8,9a,9b-hexahydro-3aH-[1,4]dioxino[2', 3':4,5]pyrano[3,2-d]thiazol-2-yl)(methyl) carbamate as a white solid (0.077 g, 68.9%). $^1$H NMR (400 MHz, CDCl$_3$) δ 7.42-7.35 (m, 5H), 6.13 (d, J=7.2 Hz, 1H), 4.56 (td, J=7.6, 1.6 Hz, 1H), 4.29-4.21 (m, 2H), 4.18-4.08 (m, 2H), 3.83 (t, J=10.4 Hz, 1H), 3.55 (t, J=10.0 Hz, 1H), 3.32 (s, 3H), 3.23 (s, 3H), 3.16 (s, 3H), 3.12 (dd, J=15.2, 9.2 Hz, 1H), 1.53 (s, 9H), 1.31 (s, 3H), 1.25 (s, 3H).

(3aR,5S,6S,7R,7aR)-5-((benzylsulfonyl)methyl)-2-(methylamino)-5,6,7,7a-tetrahydro-3aH-pyrano[3,2-d]thiazole-6,7-diol

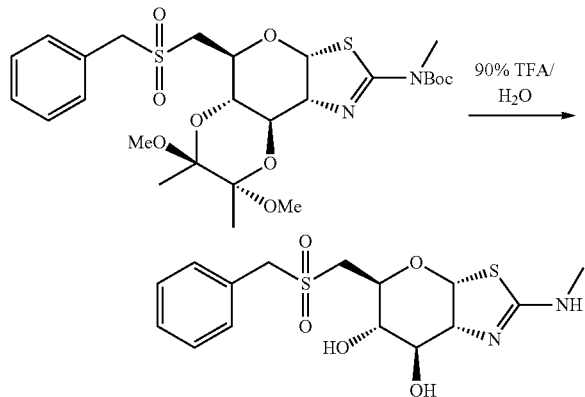

At 0° C., to tert-butyl((3aR,5S,5aS,7S,8S,9aR,9bR)-5-((benzylsulfonyl)methyl)-7,8-dimethoxy-7,8-dimethyl-5,5a,7,8,9a,9b-hexahydro-3aH-[1,4]dioxino[2',3':4,5]pyrano[3,2-d]thiazol-2-yl)(methyl) carbamate (0.077 g, 0.13 mmol) was added a solution of 90% TFA/H$_2$O (10 mL) and stirred at this temperature for 10 mins. Ice-bath was removed and reaction stirred for 5 h at RT. The reaction mixture was evaporated to dryness. The residue was neutralized with 1.5 M NH$_3$/MeOH solution (10 mL) and concentrated. The crude residue was purified by silica gel column chromatography (DCM/MeOH, 9:1) to provide (3aR,5S,6S,7R,7aR)-5-((benzylsulfonyl)methyl)-2-(methylamino)-5,6,7,7a-tetrahydro-3aH-pyrano[3,2-d]thiazole-6,7-diol as a white solid (0.023 g, 46.9%). $^1$H NMR (400 MHz, CD$_3$OD) δ 7.43-7.36 (m, 5H), 6.39 (d, J=6.0 Hz, 1H), 4.43 (d, J=13.6 Hz, 1H), 4.37 (d, J=14.0 Hz, 1H), 4.17-4.12 (m, 2H), 3.98 (t, J=5.2 Hz, 1H), 3.40 (dd, J=9.6, 5.2 Hz, 1H), 3.33-3.29 (m, 2H), 2.89 (s, 3H), $^{13}$C NMR (100 MHz, CD$_3$OD) δ 166.09, 133.35, 130.66, 130.52, 130.22, 90.88, 76.12, 74.42, 74.97, 72.20, 62.34, 55.96, 31.63. MS, (ES, m/z) [M+H]$^+$ 373.1.

Biological Activity

Assay for Determination of K$_1$ Values for Inhibition of O-GlcNAcase Activity

Experimental procedure for kinetic analyses: Enzymatic reactions were carried out in a reaction containing 50 mM NaH$_2$PO$_4$, 100 mM NaCl and 0.1% BSA (pH 7.0) using 2 mM 4-Methylumbelliferyl N-acetyl-β-D-glucosaminide dihydrate (Sigma M2133) dissolved in ddH$_2$O, as a substrate. The amount of purified human O-GlcNAcase enzyme used in the reaction was 0.7 nM. Test compound of varying concentrations was added to the enzyme prior to initiation of the reaction. The reaction was performed at room temperature in a 96-well plate and was initiated with the addition of substrate. The production of fluorescent product was measured every 60 sec for 45 min with a Tecan Infinite M200 plate-reader with excitation at 355 nM and emission detected at 460 nM, with 4-Methylumbelliferone (Sigma M1381) used to produce a standard curve. The slope of product production was determined for each concentration of compound tested and plotted, using standard curve fitting algorithms for sigmoidal dose response curves. The values for a four parameter logistic curve fit of the data were determined.

K$_I$ values were determined using the Cheng-Prusoff equation; the K$_m$ of O-GlcNAcase for substrate was 0.2 mM.

Many compounds of the invention exhibit K$_I$ values for inhibition of O-GlcNAcase in the range 0.1 nM-10 μM. The K$_1$ values for compounds 1-62 are shown in Table 3 below.

Assay for Determination of Apparent Permeability (P$_{app}$)

Bi-directional transport was evaluated in LLC-PK1 cells in order to determine apparent permeability (P$_{app}$). LLC-PK1 cells can form a tight monolayer and therefore can be used to assess vectorial transport of compounds from basolateral to apical (B→A) and from apical to basolateral (A→B).

To determine P$_{app}$ LLC-PK1 cells were cultured in 96-well transwell culture plates (Millipore). Solutions containing the test compounds (1 μM) were prepared in Hank's Balanced Salt Solution with 10 mM HEPES. Substrate solution (150 μL) was added to either the apical (A) or the basolateral (B) compartment of the culture plate, and buffer (150 μL) was added to the compartment opposite to that containing the compound. At t=3 h, 50 μL samples were removed from both sides of monolayers dosed with test compound and placed in 96 well plates, scintillant (200 μL) or internal standard (100 μL labetolol 1 μM) was added to the samples and concentration was determined by liquid scintillation counting in a MicroBeta Wallac Trilux scintillation counter (Perkin Elmer Life Sciences, Boston, Mass.) or by LCMS/MS (Applied Biosystems SCIEX API 5000 triple quadruple mass spectrometer). [$^3$H]Verapamil (1 μM) was used as the positive control. The experiment was performed in triplicate.

The apparent permeability, P$_{app}$, was calculated by the following formula for samples taken at t=3 h:

$$P_{app} = \frac{\text{Volume of Receptor Chamber(mL)}}{[\text{Area of membrane(cm}^2)][\text{Initial Concentration(μM)}]} \times \frac{\Delta \text{ in Concentration(μM)}}{\Delta \text{ in time(s)}}$$

Where: Volume of Receptor Chamber was 0.15 mL; Area of membrane was 0.11 cm$^2$; the Initial Concentration is the sum of the concentration measured in the donor plus concentration measured in receiver compartments at t=3 h; Δ in Concentration is concentration in the receiver compartment at 3 h; and Δ in Time is the incubation time (3×60×60=10800 s). P$_{app}$ was expressed as 10$^{-6}$ cm/s. The P$_{app}$ (LLC-PK1 cells) are the average of the P$_{app}$ for transport from A to B and P$_{app}$ for transport from B to A at t=3 h:

$$P_{app}(LLC-PK1 \text{ Cells}) = \frac{P_{app}(A \to B) + P_{app}(B \to A)}{2}$$

Representative data from the binding, cell-based, and permeability assays described above are shown in the following table. Certain compounds of the invention exhibit superior potency or permeability in one or more of these assays as shown in Table 3.

The $P_{app}$ B→A/A→B ratios were calculated by dividing the $P_{app}$ from B to A by the $P_{app}$ from A to B at t=3 hr:

$$P_{app}\ B \to A / A \to B\ Ratio = \frac{P_{app}(B \to A)}{P_{app}(A \to B)}$$

TABLE 3

| Example | Ki (nM) | Papp (X10-6 cm/sec) | hPgp efflux ratio |
| --- | --- | --- | --- |
| 1 | 109 | | |
| 2 | 1.6 | | |
| 3 | 9.5 | | |
| 4 | 16.2 | | |
| 5 | 72 | | |
| 6 | 139 | | |
| 7 | 1.2 | | |
| 8 | 0.95 | 18.8 | 21 |
| 9 | 24 | 25.7 | 25.6 |
| 10 | 69 | | |
| 11 | 5.9 | 5.3 | 1.1 |
| 12 | 22 | | |
| 13 | 100 | | |
| 14 | 10.1 | 10 | 2.8 |
| 15 | 63 | | |
| 16 | 21 | | |
| 17 | 139 | | |
| 18 | 1.1 | | |
| 19 | 20 | | |
| 20 | 736 | 7.4 | 1.0 |
| 21 | 25.6 | 4.1 | 3.4 |
| 22 | 505 | | |
| 23 | 6.4 | 11 | 6 |
| 24 | 15 | | |
| 25 | 338 | | |
| 26 | 66 | | |
| 27 | 0.92 | 25 | 1.3 |
| 28 | 316 | 32 | 1.4 |
| 29 | 1.1 | 28 | 3.5 |
| 30 | 142.5 | | |
| 31 | 1.082 | | |
| 32 | 130 | | |
| 33 | 311 | | |
| 34 | 11.1 | 25 | 3.4 |
| 35 | 845 | | |
| 36 | 5.5 | | |
| 37 | 68 | | |
| 38 | 79 | | |
| 39 | 0.075 | | |
| 40 | 24 | | |
| 41 | 8.4 | | |
| 42 | 987 | | |
| 43 | 588 | | |
| 44 | 1432 | | |
| 45 | 2500 | | |
| 46 | 1961 | | |
| 47 | 3323 | | |
| 48 | 370 | | |
| 49 | 142 | | |
| 50 | 2881 | | |
| 51 | 1880 | | |
| 52 | 27 | | |
| 53 | 480 | | |
| 54 | 2.3 | | |
| 55 | 9.3 | | |
| 56 | 207 | | |
| 57 | 837 | 7.8 | 3.4 |
| 58 | 601 | | |
| 59 | 1.9 | 17.4 | 1.2 |
| 60 | 75 | | |
| 61 | 4.1 | 20.1 | 2.6 |
| 62 | 352 | 1.3 | 1.1 |

The present invention has been described with regard to one or more embodiments. However, it will be apparent to persons skilled in the art that a number of variations and modifications can be made without departing from the scope of the invention as defined in the claims.

REFERENCES

1. C. R. Torres, G. W. Hart, J Biol Chem 1984, 259, 3308-17.
2. R. S. Haltiwanger, G. D. Holt, and G. W. Hart, J Biol Chem 1990, 265, 2563-8.
3. L. K. Kreppel, M. A. Blomberg, and G. W. Hart, J Biol Chem 1997, 272, 9308-15.
4. W. A. Lubas, et al., J Biol Chem 1997, 272, 9316-24.
5. W. A. Lubas, J. A. Hanover, J Biol Chem 2000, 275, 10983-8.
6. D. L. Dong, G. W. Hart, J Biol Chem 1994, 269, 19321-30.
7. Y. Gao, et al., J Biol Chem 2001, 276, 9838-45.
8. E. P. Roquemore, et al., Biochemistry 1996, 35, 3578-86.
9. S. P. Jackson, R. Tjian, Cell 1988, 55, 125-33.
10. W. G. Kelly, M. E. Dahmus, and G. W. Hart, J Biol Chem 1993, 268, 10416-24.
11. M. D. Roos, et al., Mol Cell Biol 1997, 17, 6472-80.
12. N. Lamarre-Vincent, L. C. Hsieh-Wilson, J Am Chem Soc 2003, 125, 6612-3.
13. F. Zhang, et al., Cell 2003, 115, 715-25.
14. K. Vosseller, et al., Proc Natl Acad Sci USA 2002, 99, 5313-8.
15. W. A. Lubas, et al., Biochemistry 1995, 34, 1686-94.
16. L. S. Griffith, B. Schmitz, Biochem Biophys Res Commun 1995, 213, 424-31.
17. R. N. Cole, G. W. Hart, J Neurochem 1999, 73, 418-28.
18. I. Braidman, et al., Biochem J 1974, 143, 295-301.
19. R. Ueno, C. S. Yuan, Biochim Biophys Acta 1991, 1074, 79-84.
20. C. Toleman, et al., J Biol Chem 2004, 279, 53665-73.
21. F. Liu, et al., Proc Natl Acad Sci USA 2004, 101, 10804-9.
22. T. Y. Chou, G. W. Hart, Adv Exp Med Biol 2001, 491, 413-8.
23. M. Goedert, et al., Neuron 1992, 8, 159-68.
24. M. Goedert, et al., Neuron 1989, 3, 519-26.
25. E. Kopke, et al., J Biol Chem 1993, 268, 24374-84.
26. H. Ksiezak-Reding, W. K. Liu, and S. H. Yen, Brain Res 1992, 597, 209-19.
27. P. V. Arriagada, et al., Neurology 1992, 42, 631-9.
28. K. P. Riley, D. A. Snowdon, and W. R. Markesbery, Ann Neurol 2002, 51, 567-77.
29. I. Alafuzoff, et al., Acta Neuropathol (Berl) 1987, 74, 209-25.
30. C. X. Gong, et al., J Neural Transm 2005, 112, 813-38.
31. K. Iqbal, et al., J Neural Transm Suppl 2002, 309-19.
32. K. Iqbal, et al., J Mol Neurosci 2003, 20, 425-9.
33. W. Noble, et al., Proc Natl Acad Sci USA 2005, 102, 6990-5.
34. S. Le Corre, et al., Proc Natl Acad Sci USA 2006, 103, 9673-8.
35. S. J. Liu, et al., J Biol Chem 2004, 279, 50078-88.

36. G. Li, H. Yin, and J. Kuret, J Biol Chem 2004, 279, 15938-45.
37. T. Y. Chou, G. W. Hart, and C. V. Dang, J Biol Chem 1995, 270, 18961-5.
38. X. Cheng, G. W. Hart, J Biol Chem 2001, 276, 10570-5.
39. X. Cheng, et al., Biochemistry 2000, 39, 11609-20.
40. L. S. Griffith, B. Schmitz, Eur J Biochem 1999, 262, 824-31.
41. K. Kamemura, G. W. Hart, Prog Nucleic Acid Res Mol Biol 2003, 73, 107-36.
42. L. Wells, et al., J Biol Chem 2004, 279, 38466-70.
43. L. Bertram, et al., Science 2000, 290, 2302-3.
44. S. Hoyer, et al., Journal of Neural Transmission 1998, 105, 423-438.
45. C. X. Gong, et al., Journal of Alzheimers Disease 2006, 9, 1-12.
46. W. J. Jagust, et al., Journal of Cerebral Blood Flow and Metabolism 1991, 11, 323-330.
47. S. Hoyer, Experimental Gerontology 2000, 35, 1363-1372.
48. S. Hoyer, in Frontiers in Clinical Neuroscience: Neurodegeneration and Neuroprotection, Vol. 541, 2004, 135-152.
49. R. N. Kalaria, S. I. Harik, Journal of Neurochemistry 1989, 53, 1083-1088.
50. I. A. Simpson, et al., Annals of Neurology 1994, 35, 546-551.
51. S. M. de la Monte, J. R. Wands, Journal of Alzheimers Disease 2005, 7, 45-61.
52. X. W. Zhu, G. Perry, and M. A. Smith, Journal of Alzheimers Disease 2005, 7, 81-84.
53. J. C. de la Torre, Neurological Research 2004, 26, 517-524.
54. S. Marshall, W. T. Garvey, and R. R. Traxinger, Faseb J 1991, 5, 3031-6.
55. S. P. Iyer, Y. Akimoto, and G. W. Hart, J Biol Chem 2003, 278, 5399-409.
56. K. Brickley, et al., J Biol Chem 2005, 280, 14723-32.
57. S. Knapp, C. H. Yang, and T. Haimowitz, Tetrahedron Letters 2002, 43, 7101-7104.
58. S. P. Iyer, G. W. Hart, J Biol Chem 2003, 278, 24608-16.
59. M. Jinek, et al., Nat Struct Mol Biol 2004, 11, 1001-7.
60. K. Kamemura, et al., J Biol Chem 2002, 277, 19229-35.
61. Y. Deng, et al., FASEB J. 2007, fj.07-8309com.
62. L. F. Lau, et al., Curr Top Med Chem 2002, 2, 395-415.
63. M. P. Mazanetz, P. M. Fischer, Nature Reviews Drug Discovery 2007, 6, 464-479.
64. S. A. Yuzwa, et al., Nat Chem Biol 2008, 4, 483-490.
65. P. Bounelis, et al., Shock 2004, 21 170 Suppl. 2, 58-58.
66. N. Fulop, et al., Circulation Research 2005, 97, E28-E28.
67. J. Liu, R. B. Marchase, and J. C. Chatham, Faseb Journal 2006, 20, A317-A317.
68. R. Marchase, et al., PCT Int. Appl. WO 2006016904 2006.
69. N. Fulop, et al., Journal of Molecular and Cellular Cardiology 2004, 37, 286-287.
70. N. Fulop, at al., Faseb Journal 2005, 19, A689-A690.
71. J. Liu, R. B. Marchase, and J. C. Chatham, Journal of Molecular and Cellular Cardiology 2007, 42, 177-185.
72. L. G. Not, et al., Faseb Journal 2006, 20, A1471-A1471.
73. S. L. Yang, et al., Shock 2006, 25, 600-607.
74. L. Y. Zou, et al., Faseb Journal 2005, 19, A1224-A1224.
75. R. B. Marchase, et al., Circulation 2004, 110, 1099-1099.
76. J. Liu, et al., Journal of Molecular and Cellular Cardiology 2006, 40, 303-312.
77. J. Liu, J. C. Chatham, and R. B. Marchase, Faseb Journal 2005, 19, A691-A691.
78. T. Nagy, et al., American Journal of Physiology-Cell Physiology 2006, 290, C57-C65.
79. N. Fulop, R. B. Marchase, and J. C. Chatham, Cardiovascular Research 2007, 73, 288-297.
80. T. Lefebvre, et al., Expert Review of Proteomics 2005, 2, 265-275.
81. B. Henrissat, A. Bairoch, Biochem J 1993, 293 (Pt 3), 781-8.
82. B. Henrissat, A. Bairoch, Biochem J 1996, 316 (Pt 2), 695-6.
83. L. Wells, K. Vosseller, and G. W. Hart, Science 2001, 291, 2376-8.
84. J. A. Hanover, FASEB J 2001, 15, 1865-76.
85. D. A. McClain, et al., Proc Natl Acad Sci USA 2002, 99, 10695-9.
86. P. J. Yao, P. D. Coleman, J Neurosci 1998, 18, 2399-411.
87. W. H. Yang, et al., Nature Cell Biology 2006, 8, 1074-U53.
88. B. Triggs-Raine, D J. Mahuran, and R. A. Gravel, Adv Genet 2001, 44, 199-224.
89. D. Zhou, et al., Science 2004, 1786-89.
90. G. Legler, et al., Biochim Biophys Acta 1991, 1080, 89-95.
91. M. Horsch, et al., Eur J Biochem 1991, 197, 815-8.
92. J. Liu, et al., Chem Biol 2001, 8, 701-11.
93. S. Knapp, et al., J. Am. Chem. Soc. 1996, 118, 6804-6805.
94. V. H. Lillelund, et al., Chem Rev 2002, 102, 515-53.
95. R. J. Konrad, et al., Biochem J 2001, 356, 31-41.
96. K. Liu, et al., J Neurochem 2004, 89, 1044-55.
97. G. Parker, et al., J Biol Chem 2004, 279, 20636-42.
98. E. B. Arias, J. Kim, and G. D. Cartee, Diabetes 2004, 53, 921-30.
99. A. Junod, et al., Proc Soc Exp Biol Mod 1967, 126, 201-5.
100. R. A. Bennett, A. E. Pegg, Cancer Res 1981, 41, 2786-90.
101. K. D. Kroncke, et al., Biol Chem Hoppe Seyler 1995, 376, 179-85.
102. H. Yamamoto, Y. Uchigata, and H. Okamoto, Nature 1981, 294, 284-6.
103. K. Yamada, et al., Diabetes 1982, 31, 749-53.
104. V. Burkart, et al., Nat Med 1999, 5, 314-9.
105. M. D. Roos, et al., Proc Assoc Am Physicians 1998, 110, 422-32.
106. Y. Gao, G. J. Parker, and G. W. Hart, Arch Biochem Biophys 2000, 383, 296-302.
107. R. Okuyama, M. Yachi, Biochem Biophys Res Commun 2001, 287, 366-71.
108. N. E. Zachara, et al., J Biol Chem 2004, 279, 30133-42.
109. J. A. Hanover, et al., Arch Biochem Biophys 1999, 362, 38-45.
110. K. Liu, et al., Mol Cell Endocrinol 2002, 194, 135-46.
111. M. S. Macauley, et al., J Biol Chem 2005, 280, 25313-22.
112. B. L. Mark, et al., J Biol Chem 2001, 276, 10330-7.
113. R. S. Haltiwanger, K. Grove, and G. A. Philipsberg, J Biol Chem 1998, 273, 3611-7.
114. D. J. Miller, X. Gong, and B. D. Shur, Development 1993, 118, 1279-89.
115. L. Y. Zou, et al., Shock 2007, 27, 402-408.
116. J. B. Huang, A. J. Clark, and H. R. Petty, Cellular Immunology 2007, 245, 1-6.

117. N. E. Zachara, et al., Abstract 418 in Joint Meeting of the Society for Glycobiology and the Japanese Society of Carbohydrate Research. Honolulu, Hi., 2004.
118. L. Y. Zou, et al., Faseb Journal 2006, 20, A1471-A1471.
119. V. Champattanachai, R. B. Marchase, and J. C. Chatham, American Journal of Physiology-Cell Physiology 2007, 292, C178-C187.
120. V. Champattanachai, R. B. Marchase, and J. C. Chatham, American Journal of Physiology-Cell Physiology 2008, 294, C1509-C1520.
121. I. Khlistunova, et al., Current Alzheimer Research 2007, 4, 544-546.
122. P. Friedhoff, et al., Biochemistry 1998, 37, 10223-10230.
123. M. Pickhardt, et al., Journal of Biological Chemistry 2005, 280, 3628-3635.

What is claimed:

1. A compound of Formula (I)

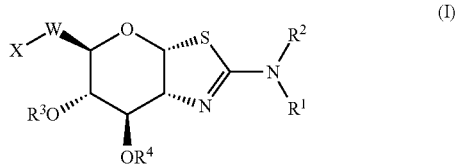

or a pharmaceutically acceptable salt thereof, wherein:
$R^1$ and $R^2$ are each independently hydrogen, C1-6alkyl, C2-6alkenyl or C2-6alkynyl wherein the alkyl, alkenyl or alkynyl are optionally substituted with one up to the maximum number of substituents with one or more of fluoro, —OH, or methyl;
$R^3$ and $R^4$ are each independently hydrogen, or C1-6acyl;
W is
  (1) —$(CH_2)_m$—$C(R^5R^6)$—* wherein m is 1-3, $R^5$ and $R^6$ are each independently hydrogen, C1-3alkyl, —OH, halo, or —$CF_3$, and the * represents the point of attachment to the tetrahydropyran ring;
  (2) —$(CH_2)_n$—CH=$C(R^7)$—* wherein n is 0-3, $R^7$ is hydrogen or —$CF_3$, and the * represents the point of attachment to the tetrahydropyran ring;
  (3) —$(CH_2)_p$—$S(O)_2$—$CH_2$—* wherein p is 0-1, and the * represents the point of attachment to the tetrahydropyran ring; or
  (4) —$(CH_2)_q$—S—$CH_2$—* wherein q is 0-1 and the * represents the point of attachment to the tetrahydropyran ring; and
X is
  (1)

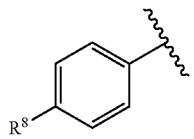

wherein $R^8$ is hydrogen or C1-3alkoxy,
  (2) —C(O)—O—$R^9$ wherein $R^9$ is hydrogen, C1-3alkyl, C2-3alkenyl or C2-3alkynyl; or
  (3) —C(O)—$NR^{10}R^{11}$ wherein $R^{10}$ and $R^{11}$ are each independently hydrogen, C1-3alkyl, C2-3alkenyl or C2-3alkynyl;

with the proviso that if W is —$(CH_2)_m$—$C(R^5R^6)$—*, then X is (2) —C(O)—O—$R^9$, or (3) —C(O)—$NR^{10}R^{11}$.

2. The compound according to claim 1 or a pharmaceutically acceptable salt thereof, wherein $R^1$ and $R^2$ are each hydrogen or methyl.

3. The compound according to claim 1 or a pharmaceutically acceptable salt thereof, wherein $R^3$ and $R^4$ are hydrogen.

4. The compound according to claim 1 or a pharmaceutically acceptable salt thereof, wherein W is —$(CH_2)_m$—$C(R^5R^6)$—* wherein m is 1-3, $R^5$ and $R^6$ are each independently hydrogen, C1-3alkyl, —OH, halo, or —$CF_3$, and the * represents the point of attachment to the tetrahydropyran ring.

5. The compound according to claim 1 or a pharmaceutically acceptable salt thereof, wherein W is —$(CH_2)_n$—CH=$C(R^7)$—* wherein n is 0-3, $R^7$ is hydrogen or —$CF_3$, and the * represents the point of attachment to the tetrahydropyran ring.

6. The compound according to claim 1 or a pharmaceutically acceptable salt thereof wherein W is —$(CH_2)_p$—$S(O)_2$—$CH_2$—*, wherein p is 0-1 and the * represents the point of attachment to the tetrahydropyran ring, or W is —$(CH_2)_q$—S—$CH_2$—*, wherein q is 0-1 and the * represents the point of attachment to the tetrahydropyran ring.

7. The compound according to claim 1 wherein X is:

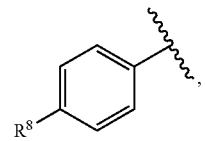

wherein $R^8$ is hydrogen or C1-3alkoxy.

8. The compound according to claim 1 or a pharmaceutically acceptable salt thereof wherein X is —C(O)—O—$R^9$ wherein $R^9$ is hydrogen or C1-3alkyl.

9. The compound according to claim 1 or a pharmaceutically acceptable salt thereof wherein X is —C(O)—$NR^{10}R^{11}$ wherein $R^{10}$ and $R^{11}$ are each independently hydrogen or C1-3alkyl.

10. The compound according to claim 1 or a pharmaceutically acceptable salt thereof wherein
  $R^1$ is hydrogen and $R^2$ is methyl, or $R^1$ is methyl and $R^2$ is hydrogen, or $R^1$ and $R^2$ are both methyl;
  $R^3$ and $R^4$ are hydrogen;
  W is —$(CH_2)_m$—$C(R^5R^6)$—* wherein m is 1-2, $R^5$ and $R^6$ are each independently hydrogen, —OH, fluoro, or —$CF_3$, and the * represents the point of attachment to the tetrahydropyran ring; and
  X is —C(O)—O—$R^9$ wherein $R^9$ is hydrogen or C1-3alkyl.

11. The compound according to claim 1 or a pharmaceutically acceptable salt thereof wherein
  $R^1$ is hydrogen and $R^2$ is methyl, or $R^1$ is methyl and $R^2$ is hydrogen, or $R^1$ and $R^2$ are both methyl;
  $R^3$ and $R^4$ are hydrogen;
  W is $(CH_2)_m$—$C(R^5R^6)$—* wherein m is 1-3, $R^5$ and $R^6$ are each independently hydrogen, —OH, fluoro, or —$CF_3$, and the * represents the point of attachment to the tetrahydropyran ring; and
  X is —C(O)—$NR^{10}R^{11}$ wherein $R^{10}$ and $R^{11}$ are each independently hydrogen or C1-3alkyl.

12. The compound according to claim 1 or a pharmaceutically acceptable salt thereof wherein R¹ is hydrogen and R² is methyl, or R¹ is methyl and R² is hydrogen, or R¹ and R² are both methyl;

W is —(CH₂)ₙ—CH=C(R⁷)—* wherein n is 0-1, R⁷ is hydrogen or —CF₃, and the * represents the point of attachment to the tetrahydropyran ring; and X is (1)

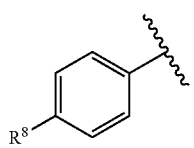

wherein R⁸ is hydrogen or C1-3alkoxy, or (2) —C(O)—O—R⁹ wherein R⁹ is hydrogen or C1-3alkyl.

13. A compound which is selected from the group consisting of:

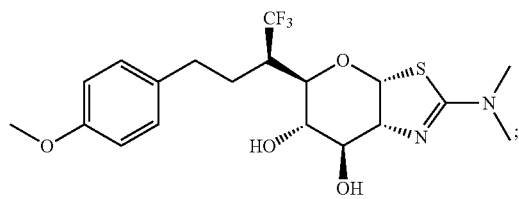

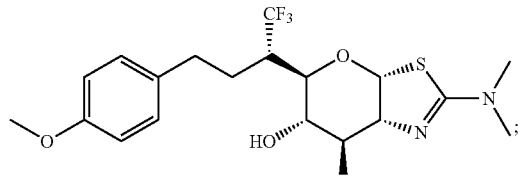

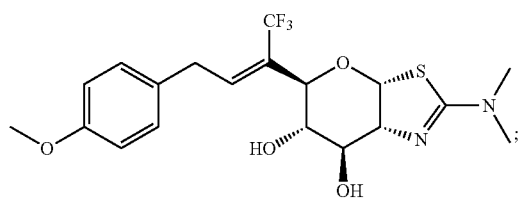

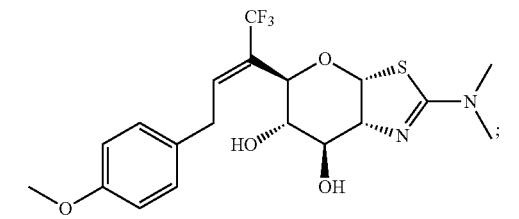

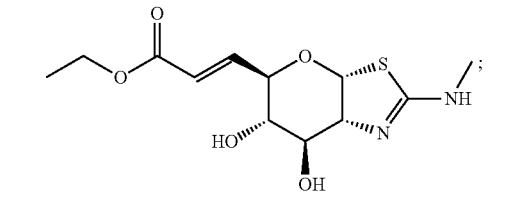

-continued

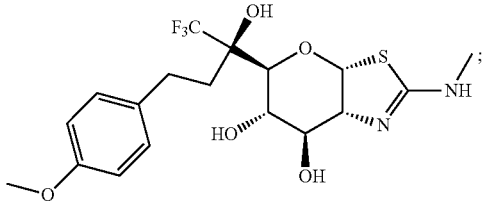

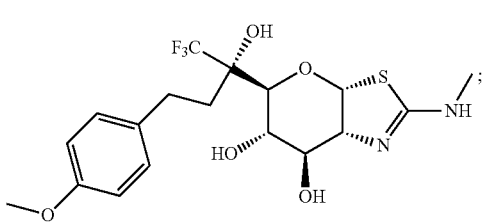

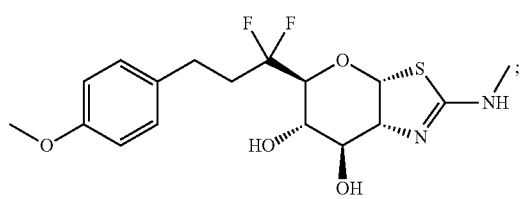

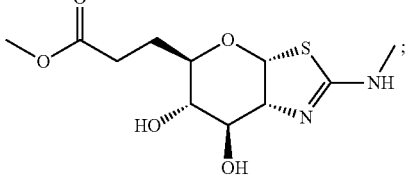

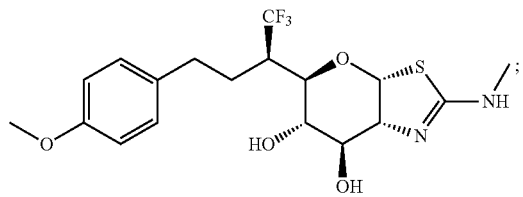

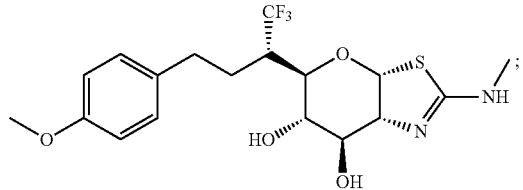

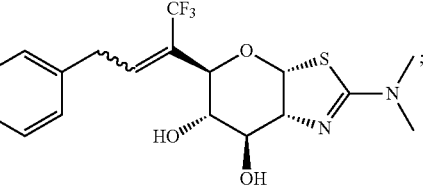

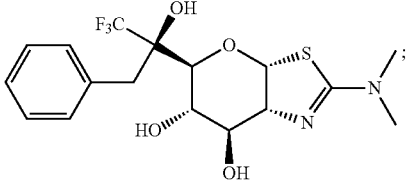

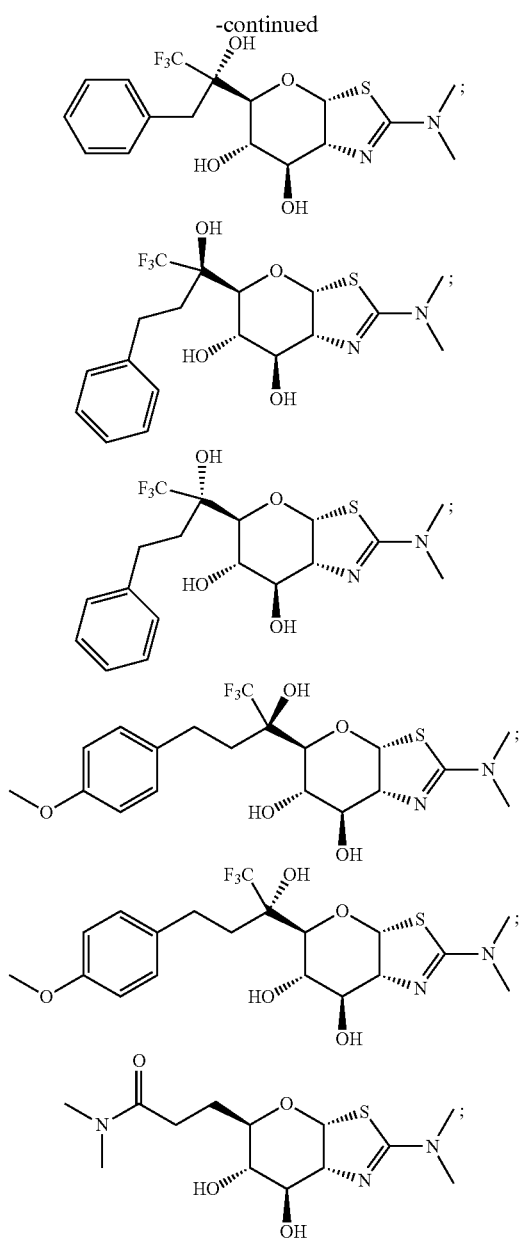

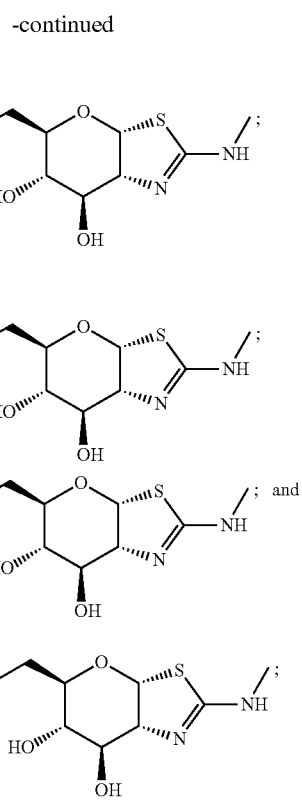

or a pharmaceutically acceptable salt thereof.

14. A pharmaceutical composition comprising the compound of claim 1 or a pharmaceutically acceptable salt thereof, and a pharmaceutically acceptable carrier.

15. A method for treating a disease or disorder selected from the group consisting of consisting of Alzheimer's disease, Amyotrophic lateral sclerosis, glaucoma, schizophrenia, Huntington's disease, Parkinson's disease, Schizophrenia, Mild Cognitive Impairment (MCI) and Neuropathy, the method comprising administering to a subject in need thereof a therapeutically effective amount of a compound according to claim 1 or a pharmaceutically acceptable salt thereof.

* * * * *